(12) United States Patent
Bi et al.

(10) Patent No.: US 8,946,415 B2
(45) Date of Patent: Feb. 3, 2015

(54) PYRAZOLO[1,5-A]PYRIMIDINE-BASED COMPOUNDS, COMPOSITIONS COMPRISING THEM, AND METHODS OF THEIR USE

(71) Applicants: Yingzhi Bi, Plainsboro, NJ (US); Kenneth Gordon Carson, Princeton, NJ (US); Giovanni Cianchetta, Waltham, MA (US); Michael Alan Green, Easton, PA (US); Godwin Kumi, Belle Mead, NJ (US); Alan Main, Far Hills, NJ (US); Yulian Zhang, Acton, MA (US); Gregory Glenn Zipp, Robbinsville, NJ (US)

(72) Inventors: Yingzhi Bi, Plainsboro, NJ (US); Kenneth Gordon Carson, Princeton, NJ (US); Giovanni Cianchetta, Waltham, MA (US); Michael Alan Green, Easton, PA (US); Godwin Kumi, Belle Mead, NJ (US); Alan Main, Far Hills, NJ (US); Yulian Zhang, Acton, MA (US); Gregory Glenn Zipp, Robbinsville, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 13/785,355

(22) Filed: Mar. 5, 2013

(65) Prior Publication Data

US 2013/0253194 A1 Sep. 26, 2013

Related U.S. Application Data

(60) Provisional application No. 61/608,765, filed on Mar. 9, 2012.

(51) Int. Cl.
*C07D 487/04* (2006.01)
*A61K 31/519* (2006.01)

(52) U.S. Cl.
CPC ............ *C07D 487/04* (2013.01); *A61K 31/519* (2013.01)
USPC ......................................................... 544/281

(58) Field of Classification Search
CPC ..................................................... C07D 487/04
See application file for complete search history.

(56) References Cited

U.S. PATENT DOCUMENTS

| | | |
|---|---|---|
| 6,194,410 B1 | 2/2001 | Boes |
| 2009/0286779 A1 | 11/2009 | Imbach |
| 2012/0178715 A1 | 7/2012 | Andrews |
| 2013/0245021 A1 | 9/2013 | Bi |

FOREIGN PATENT DOCUMENTS

| | | |
|---|---|---|
| WO | WO 2011/087999 A1 | 7/2011 |
| WO | WO 2013/134336 | 9/2013 |
| WO | WO2013134336 A2 * | 9/2013 |

OTHER PUBLICATIONS

International Search Report for Patent Application No. PCT/US2013/029056, dated Apr. 15, 2013.
Brecher, J., "Graphical Representation Standards for Chemical Structure Drawing," Pure Appl. Chem. 80(2):277-410, 2008.

* cited by examiner

*Primary Examiner* — Noble Jarrell
*Assistant Examiner* — John S Kenyon
(74) *Attorney, Agent, or Firm* — Max Bachrach

(57) ABSTRACT

Pyrazolo[1,5-a]pyrimidine-based compounds of the formula:

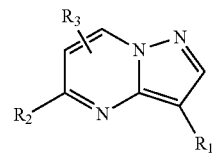

are disclosed, wherein $R_1$, $R_2$ and $R_3$ are defined herein. Compositions comprising the compounds and methods of their use to treat, manage and/or prevent diseases and disorders mediated by adaptor associated kinase 1 activity are also disclosed.

15 Claims, 1 Drawing Sheet

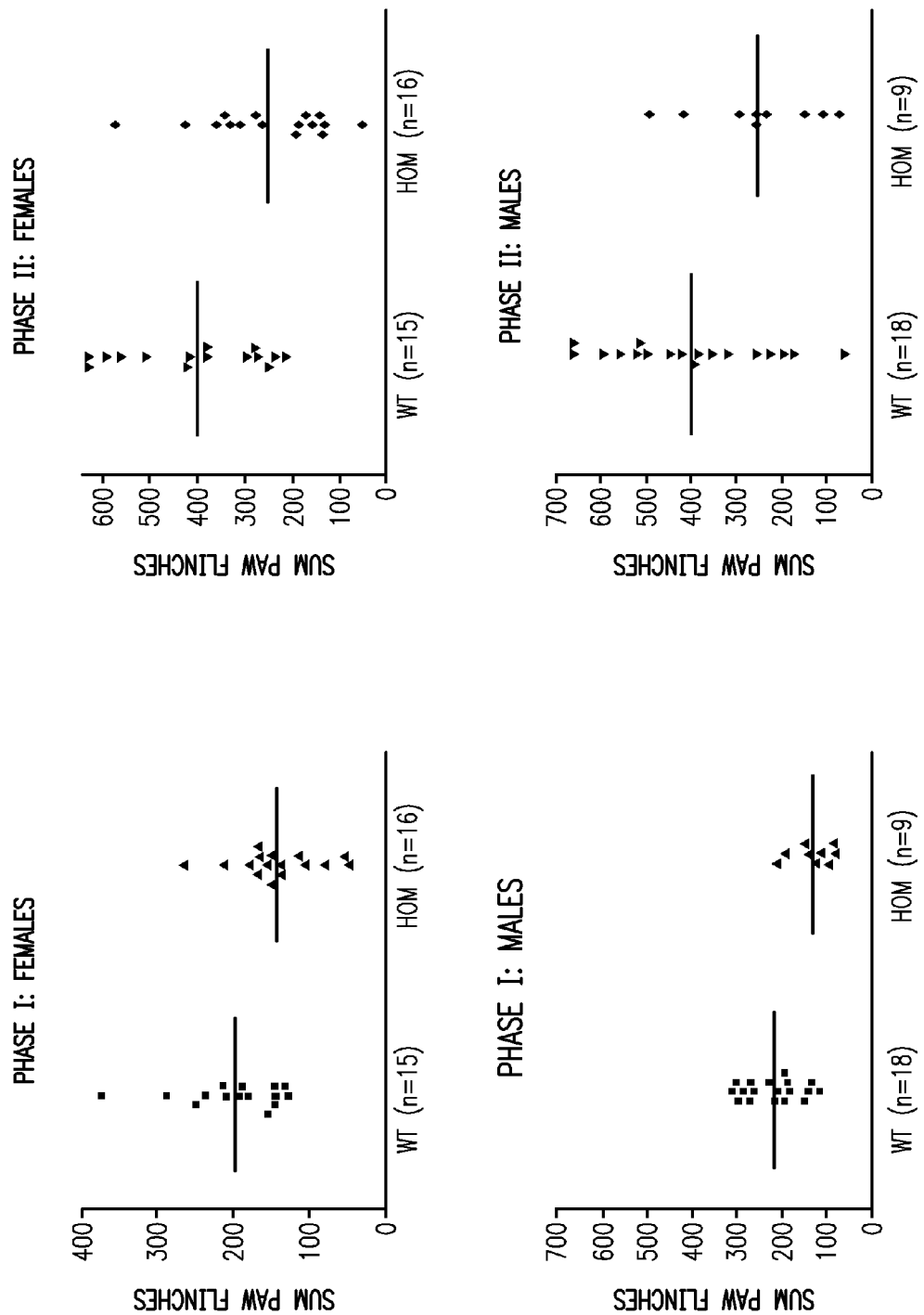

PYRAZOLO[1,5-A]PYRIMIDINE-BASED COMPOUNDS, COMPOSITIONS COMPRISING THEM, AND METHODS OF THEIR USE

This application claims priority to U.S. provisional patent application No. 61/608,765, filed Mar. 9, 2012, the entirety of which is incorporated herein by reference.

1. FIELD OF THE INVENTION

This invention is directed to pyrazolo[1,5-a]pyrimidine-based compounds useful as inhibitors of adaptor associated kinase 1 (AAK1), compositions comprising them, and methods of their use.

2. BACKGROUND OF THE INVENTION

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., *Proc. Natl. Acad. Sci. USA.* 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, bipolar disorder, and Alzheimer's disease.

3. SUMMARY OF THE INVENTION

This invention is directed, in part, to AAK1 inhibitors of the formula:

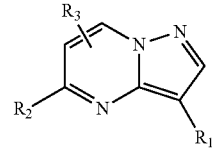

and pharmaceutically acceptable salt thereof, wherein: $R_1$ is $R_{1A}$ or optionally substituted $C_{1-12}$ hydrocarbyl or 2-12-membered heterocarbyl, which optional substitution is with one or more $R_{1A}$; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; $R_2$ is —$NR_{2A}R_{2B}$, wherein $R_{2A}$ is hydrogen and $R_{2B}$ is optionally substituted $C_{1-12}$ hydrocarbyl or 2-12-membered heterocarbyl, which optional substitution is with one or more $R_{2C}$; or $R_{2A}$ and $R_{2B}$ are taken together to form a 4-7-membered heterocycle optionally substituted with one or more $R_{2C}$; each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, or optionally substituted $C_{1-12}$ hydrocarbyl or 2-12-membered heterocarbyl, which optional substitution is with one or more with one or more $R_{2D}$; each $R_{2D}$ is independently hydrogen or optionally substituted $C_{1-12}$ hydrocarbyl or 2-12-membered heterocarbyl, which optional substitution is with one or more of cyano, halo or hydroxyl; and $R_3$ is hydrogen or $C_{1-6}$ alkyl optionally substituted with one or more of cyano, halo or hydroxyl.

One embodiment of the invention encompasses pharmaceutical compositions and dosage forms comprising a compound disclosed herein (i.e., a compound of the invention).

Another embodiment of this invention encompasses methods of inhibiting adaptor associated kinase 1 (AAK1), both in vitro and in vivo, which comprise contacting AAK1 with a compound of the invention.

Another embodiment encompasses methods of treating and managing diseases and disorders mediated by AAK1 activity. Examples of such diseases and disorders are believed to include Alzheimer's disease, bipolar disorder, pain, Parkinson's disease, and schizophrenia (including cognitive deficits in schizophrenia).

4. BRIEF DESCRIPTION OF THE FIGURES

Aspects of the invention are illustrated in FIG. 1, which shows results obtained from a formalin pain model using AAK1 homozygous (−/−) knockout mice and their wild-type (+/+) littermates. The AAK1 homozygous (−/−) knockout mice show a clear reduction in both acute and tonic pain response as compared to their wild-type (+/+) littermates.

5. DETAILED DESCRIPTION OF THE INVENTION

This invention is based, in part, on the discovery that AAK1 knockout mice exhibit a high resistance to pain. That discovery prompted research that ultimately led to the discovery of AAK1 inhibitors, compositions comprising them, and methods of their use.

5.1. Definitions

Unless otherwise indicated, the phrases "compounds of the invention," "compounds of the present disclosure," and the like refer to the compounds disclosed herein.

Unless otherwise indicated, the term "hydrocarbyl" means an aliphatic or alicyclic moiety having an all-carbon backbone and consisting of carbon and hydrogen atoms. Examples of hydrocarbyl groups include those having 1-20, 1-12, 1-6, and 1-4 carbon atoms (referred to as $C_{1-20}$ hydrocarbyl, $C_{1-12}$ hydrocarbyl, $C_{1-6}$ hydrocarbyl, and $C_{1-4}$ hydrocarbyl, respectively). Particular examples include alkyl, alkenyl, alkynyl, aryl, benzyl, cycloalkyl, cycloalkenyl, cycloalkylalkyl, cycloalkenylalkyl, napthyl, phenyl, and phenylethyl.

Examples of alkyl moieties include straight-chain and branched moieties having 1-20, 1-12, 1-6, 1-4 and 1-3 carbon atoms (referred to as $C_{1-20}$ alkyl, $C_{1-12}$ alkyl, $C_{1-6}$ alkyl, $C_{1-4}$ alkyl and $C_{1-3}$ alkyl, respectively). Particular examples include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl.

Examples of alkenyl moieties include straight-chain and branched $C_{2-20}$, $C_{2-12}$ and $C_{2-6}$ alkenyl. Particular examples include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Examples of alkynyl moieties include straight-chain and branched $C_{2-20}$, $C_{2-12}$ and $C_{2-6}$ alkynyl. Particular examples include ethynyl and 2-propynyl (propargyl).

Examples of aryl moieties include anthracenyl, azulenyl, fluorenyl, indan, indenyl, naphthyl, phenyl and phenanthrenyl.

Examples of cycloalkyl moieties include $C_{3-12}$, $C_{3-7}$, $C_{4-6}$ and $C_6$ cycloalkyl. Particular examples include cyclopropyl, cyclobutyl, cyclopentyl, cyclohexyl and adamantyl.

Unless otherwise indicated, the term "halo" encompass fluoro, chloro, bromo, and iodo.

Unless otherwise indicated, the term "heterocarbyl" refers to a moiety having a backbone made up of one or more carbon atoms and one or more heteroatoms. Particular heteroatoms are nitrogen, oxygen and sulfur. A heterocarbyl moieties can be thought of as a hydrocarbyl moiety wherein at least one carbon atom, CH, $CH_2$, or $CH_3$ group is replaced with one or more heteroatoms and the requisite number of hydrogen atoms to satisy valencies. Examples of heterocarbyl include 2-20, 2-12, 2-8, 2-6 and 2-4 membered heterocarbyl moieties, wherein the number range refers to the sum total of carbon, nitrogen, oxygen, and/or sulfur atoms in the moiety. The term "2-12 membered heterocarbyl" thus refers to a heterocarbyl moiety having a total of 2-12 carbon, nitrogen, oxygen, and/ or sulfur atoms. Particular heterocarbyl moieties include straight chain and branched heteroalkyl, heteroalkenyl, and heteroalkynyl, as well as heterocycle and heteroaryl.

Examples of heteroalkyl moieties include 2-8-membered, 2-6-membered and 2-4-membered heteroalkyl moieties. Particular examples include alkoxyl, acyl (e.g., formyl, acetyl, benzoyl), alkylamino (e.g., di-(Cl_3-alkyl)amino), arylamino, aryloxime, carbamates, carbamides, alkylcarbonyl, arylcarbonyl, aminocarbonyl, alkylaminocarbonyl, alkylsulfanyl, arylsulfanyl, alkylsulfinyl, arylsulfinyl, alkylsulfonyl, arylsulfonyl, alkylsulfonylamino, and arylsulfonylamino.

Unless otherwise indicated, the term "heterocycle" refers to a cyclic (monocyclic or polycyclic) heterocarbyl moieity which may be aromatic, partially aromatic or non-aromatic. Heterocycles include heteroaryls. Examples include 4-10-membered, 4-7-membered, 6-membered, and 5-membered heterocycles. Particular examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl. Because the term "heterocycle" refers to a ring, standing alone it does not encompass moieities such as oxazolidinone and imidazolidinone: such moieties are considered substituted heterocycles, viz. heterocycles substituted with oxo.

Examples of heteroaryl moieties include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

5.2. Compounds

This invention encompasses compounds of the formula:

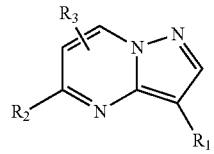

and pharmaceutically acceptable salt thereof, wherein: $R_1$ is $R_{1A}$ or optionally substituted $C_{1-12}$ hydrocarbyl or 2-12-membered heterocarbyl, which optional substitution is with one or more $R_{1A}$; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; $R_2$ is —$NR_{2A}R_{2B}$, wherein $R_{2A}$ is hydrogen and $R_{2B}$ is optionally substituted $C_{1-12}$ hydrocarbyl or 2-12-membered heterocarbyl, which optional substitution is with one or more $R_{2C}$; or $R_{2A}$ and $R_{2B}$ are taken together to form a 4-7-membered heterocycle optionally substituted with one or more $R_{2C}$; each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, or optionally substituted $C_{1-12}$ hydrocarbyl or 2-12-membered heterocarbyl, which optional substitution is with one or more with one or more $R_{2D}$; each $R_{2D}$ is independently hydrogen or optionally substituted $C_{1-12}$ hydrocarbyl or 2-12-membered heterocarbyl, which optional substitution is with one or more of cyano, halo or hydroxyl; and $R_3$ is hydrogen or $C_{1-6}$ alkyl optionally substituted with one or more of cyano, halo or hydroxyl.

In particular compounds, $R_1$ is $R_{1A}$. In some, $R_1$ is optionally substituted $C_{1-12}$ hydrocarbyl. In some, $R_1$ is optionally substituted phenyl. In some, $R_1$ is optionally substituted 2-12-membered heterocarbyl (e.g., 2-8 membered heterocarbyl, 2-6 membered heterocarbyl, 2-6 membered heterocarbyl). In some, $R_1$ is optionally substituted pyridinyl, thiophen, or imidazol.

In particular compounds, $R_{1A}$ is halo. In some, $R_{1A}$ is —$OR_{1C}$, —$N(R_{1C})_2$, —$C(O)R_{1C}$, —$C(O)OR_{1C}$, or —$C(O)N(R_{1C})_2$. In some, $R_{1A}$ is —$OR_{1C}$.

In particular compounds, $R_{1B}$ is —$N(R_{1C})_2$, —$OR_{1C}$, halo.

In particular compounds, $R_{2A}$ and $R_{2B}$ are taken together to form a 4-7-membered heterocycle optionally substituted with one or more $R_{2C}$.

In particular compounds, $R_{1C}$ is hydrogen. In some, $R_{1C}$ is $C_{1-12}$ hydrocarbyl (e.g., $C_{1-6}$ hydrocarbyl, $C_{1-4}$ hydrocarbyl such as methyl, ethyl, propyl). In some, $R_{2C}$ is —$C(O)OR_{2D}$, —$C(O)N(R_{2D})_2$, or —$N(R_{2D})C(O)OR_{2D}$.

In particular compounds, $R_{2D}$ is hydrogen.

In particular compounds, $R_{2D}$ is $C_{1-12}$ hydrocarbyl (e.g., $C_{1-6}$ hydrocarbyl, $C_{1-4}$ hydrocarbyl such as methyl, ethyl, propyl).

In particular compounds, $R_3$ is hydrogen.

One embodiment of the invention encompasses compounds of the formula:

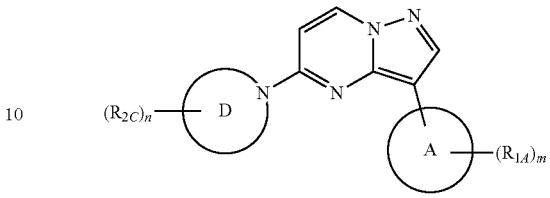

and pharmaceutically acceptable salt thereof, wherein: A is cyclic $C_{1-12}$ hydrocarbyl or 4-7-membered heterocycle; D is 4-7-membered heterocycle; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, or optionally substituted $C_{1-12}$ hydrocarbyl or 2-12-membered heterocarbyl, which optional substitution is with one or more with one or more $R_{2D}$; each $R_{2D}$ is independently hydrogen or optionally substituted $C_{1-12}$ hydrocarbyl or 2-12-membered heterocarbyl, which optional substitution is with one or more of cyano, halo or hydroxyl; n is 1-3; and m is 0-3.

In particular compounds, D is not piperidinyl.

In particular compounds, $R_{2C}$ is not —$N(R_{2D})_2$.

In particular compounds, A is not phenyl.

In particular compounds, m is 1.

In particular compounds, m is 2.

In particular compounds, $R_{2D}$ is not ethyl.

In particular compounds, when D is piperidinyl, A is phenyl, and $R_{2C}$ is —$N(R_{2D})_2$, $R_{2D}$ is not ethyl.

In particular compounds, D is piperazin or pyrrolidin.

In particular compounds, n is 1.

In particular compounds, A is pyridinyl, thiophen, or imidazol.

Particular compounds are of the formula:

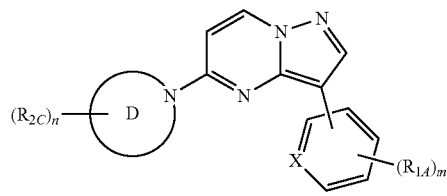

wherein X is CH or N.

Another embodiment of the invention encompasses compounds of the formula:

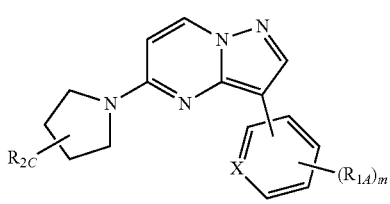

and pharmaceutically acceptable salt thereof, wherein: X is CH or N; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, or optionally substituted $C_{1-12}$ hydrocarbyl or 2-12-membered heterocarbyl, which optional substitution is with one or more with one or more $R_{2D}$; each $R_{2D}$ is independently hydrogen or optionally substituted $C_{1-12}$ hydrocarbyl or 2-12-membered heterocarbyl, which optional substitution is with one or more of cyano, halo or hydroxyl; and m is 0-3.

In particular compounds, $R_{2C}$ is not optionally substituted phenyl or pyridinyl.

In particular compounds, X is N and m is 1 or 2.

Particular compounds are of the formula:

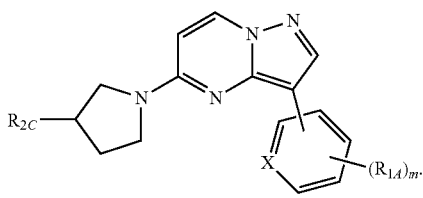

Particular compounds are of the formula:

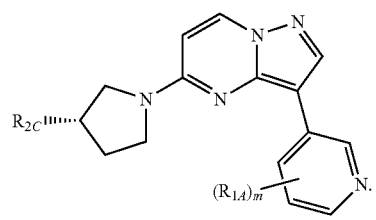

Particular compounds are of the formula:

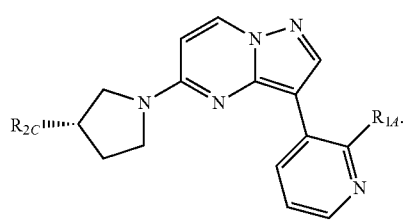

Others are of the formula:

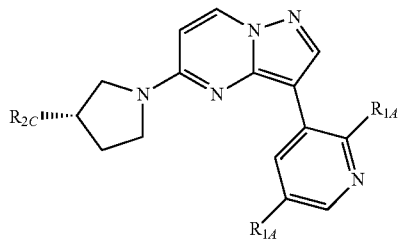

Another embodiment of the invention encompasses compounds of the formula:

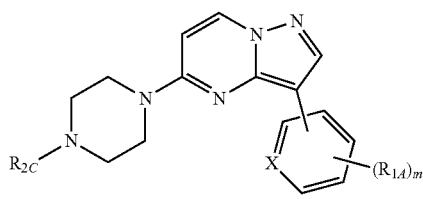

and pharmaceutically acceptable salt thereof, wherein: X is CH or N; each $R_{1A}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano, halo, or optionally substituted $C_{1-12}$ hydrocarbyl or 2-12-membered heterocarbyl, which optional substitution is with one or more $R_{1B}$; each $R_{1B}$ is independently —$OR_{1C}$, —$N(R_{1C})_2$, —$C(O)R_{1C}$, —$C(O)OR_{1C}$, —$C(O)N(R_{1C})_2$, —$N(R_{1C})C(O)OR_{1C}$, cyano or halo; each $R_{1C}$ is independently hydrogen or optionally substituted $C_{1-12}$ hydrocarbyl or 2-12-membered heterocarbyl, which optional substitution is with one or more of cyano, halo or hydroxyl; each $R_{2C}$ is independently —$OR_{2D}$, —$N(R_{2D})_2$, —$C(O)R_{2D}$, —$C(O)OR_{2D}$, —$C(O)N(R_{2D})_2$, —$N(R_{2D})C(O)OR_{2D}$, cyano, halo, or optionally substituted $C_{1-12}$ hydrocarbyl or 2-12-membered heterocarbyl, which optional substitution is with one or more with one or more $R_{2D}$; each $R_{2D}$ is independently hydrogen or optionally substituted $C_{1-12}$ hydrocarbyl or 2-12-membered heterocarbyl, which optional substitution is with one or more of cyano, halo or hydroxyl; and m is 0-3.

Particular compounds are of the formula:

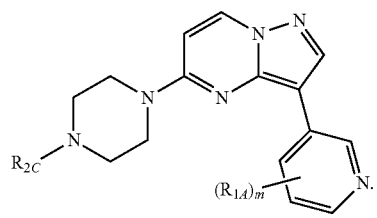

Particular compounds are of the formula:

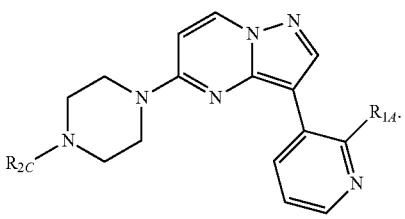

Others are of the formula:

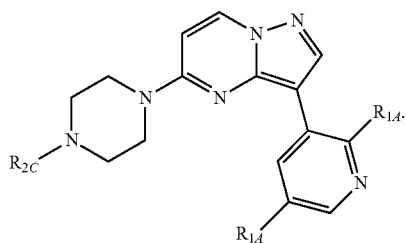

In particular compounds, $R_{1A}$ is halo. In some, $R_{1A}$ is —$OR_{1C}$.

In particular compounds, $R_{1C}$ is optionally substituted $C_{1-12}$ hydrocarbyl (e.g., $C_{1-6}$ hydrocarbyl, $C_{1-4}$ hydrocarbyl).

In particular compounds, $R_{2C}$ is —C(O)$OR_{2D}$, —C(O)N($R_{2D}$)$_2$, or —N($R_{2D}$)C(O)$OR_{2D}$. In some, $R_{2C}$ is —C(O)$R_{2D}$.

In particular compounds, $R_{2D}$ is independently hydrogen or $C_{1-12}$ hydrocarbyl (e.g., $C_{1-6}$ hydrocarbyl, $C_{1-4}$ hydrocarbyl). In some, $R_{2D}$ is optionally substituted $C_{1-12}$ hydrocarbyl, which optional substitution is with one or more of amino, cyano, halo, hydroxyl.

Compounds of the invention can have one or more asymmetric centers. Unless otherwise indicated, this invention encompasses all stereoisomers of the compounds, as well as mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

Particular compounds of the invention inhibit AAK1 with an $IC_{50}$ of less than 0.1, 0.01 or 0.001 µM as measured in the P81 filter plate assay described below in the Examples. Particular compounds of the invention inhibit AAK1 with an $IC_{50}$ of less than 0.1, 0.01 or 0.001 µM as measured in the HEK281 cell-based assay described described below in the Examples.

5.3. Methods of Synthesis

Compounds of the present invention (i.e., compounds disclosed herein) can be prepared using the methods described below and using methods known to those skilled in the art of organic chemistry. Particular compounds are of the general formula:

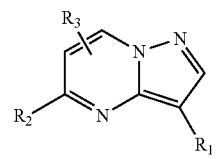

wherein $R_1$, $R_2$ and $R_3$ are defined herein, and include salts thereof. These compounds can prepared by the methods outlined below.

Compounds of formula shown above can be prepared by the methods outlined below. In Scheme 1, the chlorine of a compound of formula I is displaced with an amine to produce 2. Bromination of 2 provides 3. Alternatively 1 can be bromanated first to afford 4 then amine displacement to give 3. Suzuki coupling of 3 with an appropriate boronic acid [$R_{1B}$(OH)$_2$] affords compounds of formula 5.

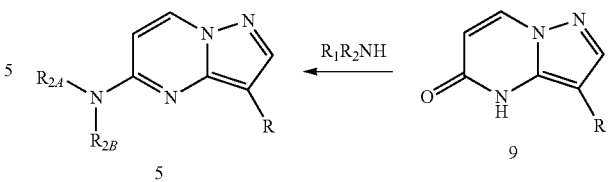

Scheme 1

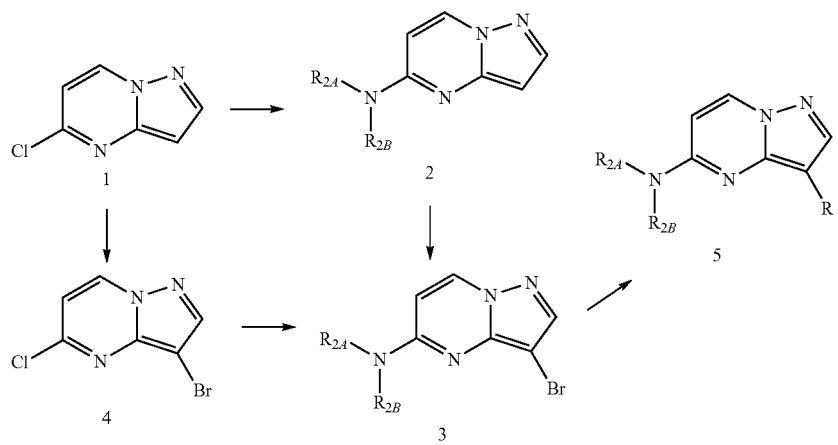

In Scheme 2, the substituted acetonitrile 6 is reacted with ethyl formate to provide 7. Condensation of 7 with hydrazine hydrate affords 8. Reaction of 8 with 1,3-dimethylpyrimidine-2,4(1H,3H)-dione provides 9. Further reaction of 9 with amine gives compounds with formula 5.

In Scheme 3, compound with formula 10 can be prepared by reacting 2 with NIS. Reaction of 10 with methyl 2,2-difluoro-2-(fluorosulfonyl)acetate provides compounds with formula 11.

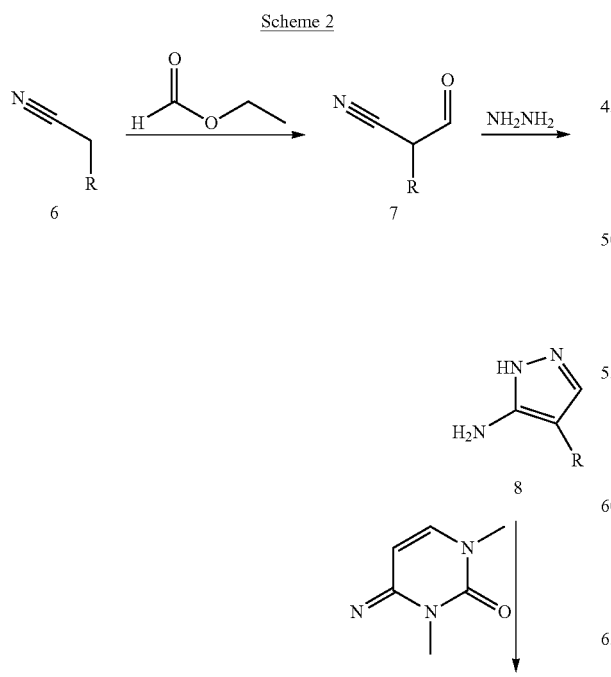

Scheme 2

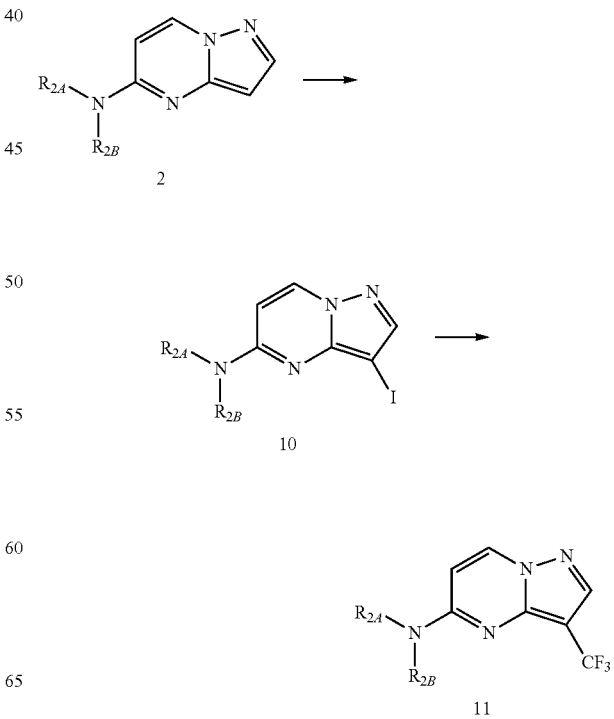

Scheme 3

5.4. Methods of Use

One embodiment of this invention encompasses methods of inhibiting adaptor associated kinase 1 (AAK1), both in vitro and in vivo, which comprise contacting AAK1 with a compound of the invention.

Another embodiment encompasses methods of treating and managing diseases and disorders mediated by AAK1 activity. Diseases and disorders mediated by AAK1 activity are diseases and disorders that have at least one symptom, the severity or manifestation of which is affected by AAK1 activity. Examples of such diseases and disorders are believed to include Alzheimer's disease, bipolar disorder, pain, Parkinson's disease, and schizophrenia (including cognitive deficits in schizophrenia). Particular methods comprise administering to a patient (a human or other mammal) in need thereof a therapeutically or prophylactically effective amount of an AAK1 inhibitor (e.g., a compound disclosed herein).

Another embodiment of this invention encompasses a method of treating or managing a disease or disorder, which comprises administering to a patient in need thereof a therapeutically or prophylactically effective amount of an AAK1 inhibitor, wherein the disease or disorder is Alzheimer's disease, bipolar disorder, pain, Parkinson's disease, or schizophrenia (including cognitive deficits in schizophrenia). Particular types of pain include chronic pain, acute pain, and neuropathic pain. Particular types of neuropathic pain include fibromyalgia and peripheral neuropathy (e.g., diabetic neuropathy).

When used to treat or manage a disease or disorder, compounds of the invention are preferably administered as part of a pharmaceutical composition comprising one or more pharmaceutically acceptable carriers, diluents or excipients.

Pharmaceutical compositions, or formulations, may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

Compounds of the invention may be administered in combination with one or more additional therapeutic or prophylactic agents. For example, when used for the treatment of pain, possible additional agents include immunosuppressive and anti-inflammatory agents.

Immunosuppressants suitable for use in the methods and compositions of this invention include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Additional examples include inosine monophosphate dehydrogenase inhibitors, such as mycophenolate mofetil (CellCept®) and mycophenolic acid (Myfortic®).

Anti-inflammatory drugs suitable for use in the methods and compositions of this invention include those known in the art. Examples include glucocorticoids and NSAIDs.

Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the invention may be administered in combination with one or more additional therapeutic or prophylactic agents directed at the underlying disease or condition. For example, when used to treat diabetic neuropathy, compounds of the invention may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

5.5. Pharmaceutical Compositions

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like.

Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

5.6. Examples

Certain aspects of the invention can be understood from the following examples.

5.6.1. AAK1 Knockout Mice

Mice homozygous (−/−) for the disruption of the AAK1 gene were prepared by two methods; gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789,215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day post-partum (lactating), 3 day post-weaning (early involution), and 7 day post-weaning (late involution)).

AAK1 homozygous (−/−) and their wild-type (+/+) littermates were tested using the formalin paw test in order to assess their acute and tonic nociceptive responses. For these tests, Automatic Nociception Analyzers (purchased from the Ozaki lab at University of California, San Diego) were used. A metal band was placed around the left hind paw of each mouse 30 minutes prior to testing. After the 30-minute acclimation period, 20 μl of 5% formalin is subcutaneously injected in the dorsal surface of the left hind paw. Mice were individually housed in cylindrical chambers for 45 minutes. A computer recorded flinches per minute, total flinches for phase I (acute phase=first 8 minutes), and total flinches for phase II (tonic phase=time between minutes 20-40) through an electromagnetic field. See Yaksh T L, Ozaki G, McCumber D, Rathbun M, Svensson C, Malkmus S, Yaksh M C. *An automated flinch detecting system for use in the formalin nociceptive bioassay. J Appl Physiol.*, 2001; 90:2386-402.

As shown in FIG. 1, phase 1 and phase 2 data were obtained using homozygous (−/−) mice females (n=16), wild-type females (n=15), homozygous (−/−) mice males (n=9), and wild-type males (n=18). In all groups and in both phases, the AAK1 homozygous (−/−) mice exhibited significantly less recorded paw flinching than their wild-type (+/+) littermates.

5.6.2. Synthesis of [3-(4-Aminomethyl-phenyl)-pyrazolo[1,5-a]pyrimidin-5-yl]-butyl-amine

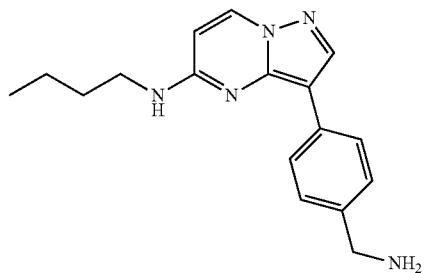 [SMILES: CCCCNc1ccn2ncc(-c3ccc(CN)cc3)c2n1]

Part A. Butyl-pyrazolo[1,5-a]pyrimidin-5-yl-amine

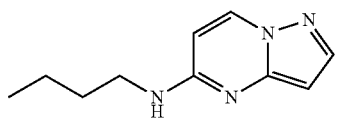

A solution of 5-chloro-pyrazolo[1,5-a]pyrimidine [29274-24-] (955.4 mg, 6.2 mmol) in butylamine [109-73-9] (6.2 mL, 62.7 mmol), under $N_2$ blanket, was magnetically stirred at 65° C. for 17 h then partitioned between brine (pH adjusted to 10 with saturated aqueous sodium bicarbonate) and ethyl acetate. The phase separated extract was dried ($MgSO_4$) and diluted with heptane to precipitate butyl-pyrazolo[1,5-a]pyrimidin-5-yl-amine as 1.2 g of yellow powder, mp. 75-76° C. $^1$H NMR (400 MHz, DMSO-$d_6$) δ ppm 0.91 (t, J=7.33 Hz, 3 H) 1.37 (dq, J=15.00, 7.29 Hz, 2 H) 1.47-1.59 (m, 2 H) 3.24-3.34 (m, 2 H) 5.94 (d, J=1.52 Hz, 1 H) 6.22 (d, J=7.58 Hz, 1 H) 7.35 (br. s., 1 H) 7.74 (d, J=2.27 Hz, 1 H) 8.40 (d, J=7.58 Hz, 1 H). $^{13}$C NMR (100 MHz, DMSO-$d_6$) δ ppm 13.69, 19.71, 30.65, 91.00, 99.95, 134.70, 143.45, 148.37, 155.43. LRMS (ESI) m/z 191.1 [(M+H)]$^+$, calc'd for $C_{10}H_{14}N_4$: 190.25

Part B. (3-Bromo-pyrazolo[1,5-a]pyrimidin-5-yl)-butyl-amine

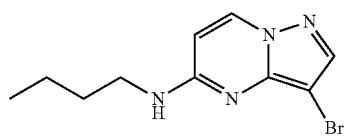

Sodium acetate [127-09-3] (0.7 g, 8.9 mmol) was added to a solution of butyl-pyrazolo[1,5-a]pyrimidin-5-yl-amine (1.1 g, 5.9 mmol) in glacial acetic acid (100 mL) and allowed to stir at ambient temperature until all of the solid had dissolved. Bromine [7726-95-6] (0.3 mL, 6.4 mmol) was added drop by drop into the ambient temperature, buffered, acetic acid reaction solution over 5 minutes. Upon completion of the bromine addition, the suspension was allowed to stir for a further 15 minutes then was slowly poured into 500 mL of stirred water. Saturated aqueous sodium bicarbonate was added to the stirred suspension until pH of the supernatant was determined to be approximately 8 by pH paper, then the suspension was extracted with ethyl acetate. The extract was dried ($MgSO_4$) and flash chromatographed (silica gel eluted with 60% (v/v) ethyl acetate/heptane) to provide 1.2 g of off white solid, mp. 94-95° C. $^1$H NMR (400 MHz, DMSO-$d_6$) δ ppm 0.93 (t, J=7.33 Hz, 3 H) 1.31-1.44 (m, 2 H) 1.56 (quin, J=7.20 Hz, 2 H) 3.31-3.38 (m, 2 H) 6.28 (d, J=7.58 Hz, 1 H) 7.61 (t, J=5.05 Hz, 1 H) 7.85 (s, 1 H) 8.42 (d, J=7.58 Hz, 1 H). $^{13}$C NMR (100 MHz, DMSO-$d_6$) δ ppm 13.67, 19.64, 30.53, 76.99, 100.87, 135.14, 143.03, 145.13, 156.09. LRMS (ESI) m/z 269.0/271.0 [(M+H)]$^+$, calc'd for $C_{10}H_{13}BrN_4$: 269.15.

Part C. [3-(4-Aminomethyl-phenyl)-pyrazolo[1,5-a]pyrimidin-5-yl]-butyl-amine

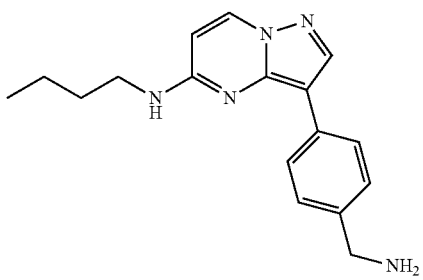 [SMILES: CCCCNc1ccn2ncc(-c3ccc(CN)cc3)c2n1]

To a mixture of (3-bromo-pyrazolo[1,5-a]pyrimidin-5-yl)-butyl-amine (350.3 mg, 1.3 mmol), 4-aminomethylphenylboronic acid, hydrochloride [75705-21-4] (337.1 mg, 1.8 mmol), potassium phosphate tribasic monohydrate [27176-10-9] (601.6 mg, 2.6 mmol), and [1,1'-bis(diphenylphosphino)ferrocene]dichloropalladium(II), complex with dichloromethane [95464-05-4] (117.2 mg, 0.1 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/$N_2$ blanket cycles while being rapidly stirred. The rapidly stirred, $N_2$ blanketed, reaction was heated to an oil bath temperature of 85° C. for 17 h then cooled and partitioned between brine and ethyl acetate. The phase separated extract was dried ($MgSO_2$) and evaporated to afford a brown oil which was purified by preparative RP-HPLC to yield 71.9 mg of [3-(4-Aminomethyl-phenyl)-pyrazolo[1,5-a]pyrimidin-5-yl]-butyl-amine monoacetate salt as a white solid, mp. 171-172° C. $^1$H NMR (400 MHz, DMSO-$d_6$) δ ppm 0.97 (t, J=7.39 Hz, 3 H) 1.43 (sxt, J=7.36 Hz, 2 H) 1.64 (quin, J=7.17 Hz, 2 H) 3.43 (q, J=6.47 Hz, 2 H) 3.71-3.84 (m, 2 H) 6.29 (d, J=7.50 Hz, 1 H) 7.34 (m, J=8.16 Hz, 2 H) 7.62-7.71 (m, 1 H) 8.05 (m, J=7.94 Hz, 2 H) 8.32 (s, 1 H) 8.46 (d, J=7.50 Hz, 1 H). $^{13}$C NMR (100 MHz, DMSO-$d_6$) δ ppm 13.03, 14.11, 19.63, 29.11, 30.33, 44.34, 45.62, 103.75, 124.02, 124.14, 126.95, 127.86, 131.85, 135.07, 137.50, 141.15, 141.36, 144.46, 155.50, 172.52. LRMS (ESI) m/z 296.1 [(M+H)]$^+$, calc'd for $C_{17}H_{21}N_5$: 295.39.

5.6.3. Synthesis of (2-Methoxy-ethyl)-{3-[4-(1H-tetrazol-5-yl)-phenyl]-pyrazolo[1,5-a]pyrimidin-5-yl}-amine

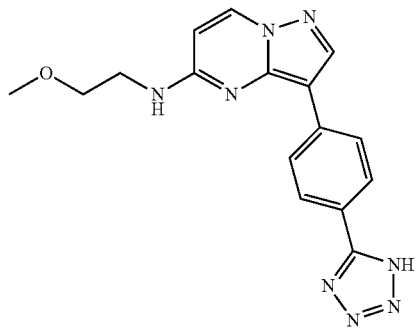 [SMILES: COCCNc1ccn2ncc(-c3ccc(-c4nnn[nH]4)cc3)c2n1]

Part A.
N-(2-methoxyethyl)pyrazolo[1,5-a]pyrimidin-5-amine

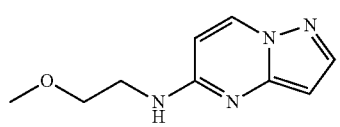

A stirred mixture of 5-chloro-pyrazolo[1,5-a]pyrimidine [29274-24-6], (525.5 mg, 3.4 mmol) and 2-methoxy-ethylamine (3.0 mL, 34.5 mmol) was heated to 65° C. for 17 h, cooled and partitioned between brine (pH adjusted to 8 with saturated aqueous sodium bicarbonate) and ethyl acetate. Extract was dried ($MgSO_4$) and evaporated to yield 706.4 mg of light yellow solid. LRMS (ESI) m/z 193.1 [(M+H)]$^+$, calc'd for $C_9H_{12}N_4O$: 192.22.

Part B. (3-Bromo-pyrazolo[1,5-a]pyrimidin-5-yl)-(2-methoxy-ethyl)-amine

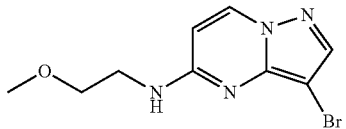

Sodium acetate [127-09-3] (457.6 mg, 5.6 mmol) was added to a solution of N-(2-methoxyethyl)pyrazolo[1,5-a]pyrimidin-5-amine (706.4 mg, 3.7 mmol) in glacial acetic acid (40 mL) and allowed to stir at ambient temperature until all of the solid had dissolved. Bromine [7726-95-6] (0.2 mL, 3.7 mmol) was added into the ambient temperature, buffered acetic acid reaction solution over 2 minutes, then the reaction solution was slowly poured into stirring water (1 L). The pH was increased by the addition of solid sodium bicarbonate until the pH of the supernatant was determined to be approximately 8 by pH paper. Precipitated product was isolated by filtration, the filter cake washed with water, and allowed to dry to afford 819.6 mg of white powder. LRMS (ESI) m/z 271.0/273.0 [(M+H)]$^+$, calc'd for $C_9H_{11}BrN_4O$: 271.12.

Part C. (2-Methoxy-ethyl)-{3-[4-(1H-tetrazol-5-yl)-phenyl]-pyrazolo[1,5-a]pyrimidin-5-yl}-amine

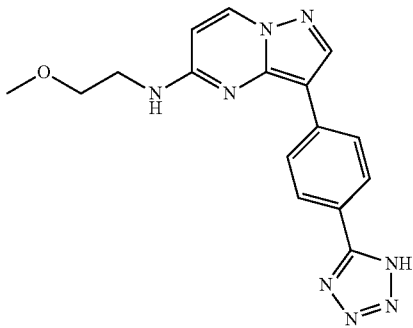 [SMILES: COCCNc1ccn2ncc(-c3ccc(-c4nnn[nH]4)cc3)c2n1]

To a mixture of (3-bromo-pyrazolo[1,5-a]pyrimidin-5-yl)-(2-methoxy-ethyl)-amine (307.7 mg, 1.1 mmol), (4-(1H-tetrazol-5-yl)phenyl)boronic acid [179942-55-3] (259.6 mg, 1.4 mmol), potassium phosphate tribasic monohydrate [27176-10-9] (522.4 mg, 2.3 mmol), and [1,1'-bis(diphenylphosphino)ferrocene]dichloro-palladium(II), complex with dichloromethane [95464-05-4] (106.3 mg, 0.1 mmol) contained in a 50 mL round bottomed flask was added a solution of 30% (v/v) water in 1,2-dimethoxyethane (12 mL) and a magnetic stir bar. The reaction pot was fitted to a reflux condenser, lowered into an ambient temperature oil bath, and the system taken through 10 evacuation/N$_2$ blanket cycles while being rapidly stirred. The rapidly stirred, N$_2$ blanketed, reaction was heated to an oil bath temperature of 85° C. for 4 h then cooled, diluted with methanol, and gravity filtered. The filtrate was preabsorbed on silica gel and flash chromatographed (silica gel eluted with 1% NH$_4$OH in 10% (v/v) methanol/ethyl acetate). Desired chromatography fractions were combined, evaporated, redissolved in 2-propanol and gravity filtered into stirring heptane to precipitate purified product. (2-Methoxy-ethyl)-{3-[4-(1H-tetrazol-5-yl)-phenyl]-pyrazolo[1,5-a]pyrimidin-5-yl}-amine was isolated by filtration as 96.3 mg of solid material, mp. 264-265° C. (dec.). $^1$H NMR (400 MHz, DMSO-d$_6$) δ ppm 3.63 (t, J=4.29 Hz, 5 H) 6.41 (d, J=7.58 Hz, 1 H) 7.88 (br. s., 1 H) 8.04 (m, J=8.59 Hz, 2 H) 8.31 (m, J=8.34 Hz, 2 H) 8.47 (s, 1 H) 8.53 (d, J=7.58 Hz, 1 H). $^{13}$C NMR (100 MHz, DMSO-d$_6$) δ ppm 40.69, 58.48, 70.48, 100.86, 103.75, 119.86, 125.23, 127.61, 135.97, 137.08, 142.42, 145.63, 156.60, LRMS (ESI) m/z 337.2 [(M+H)]$^+$, calc'd for $C_{16}H_{16}N_8O$: 336.36.

5.6.4. Synthesis of Methyl-[2-(3-thiophen-2-yl-pyrazolo[1,5-a]pyrimidin-5-ylamino)-ethyl]-carbamic acid tert-butyl ester

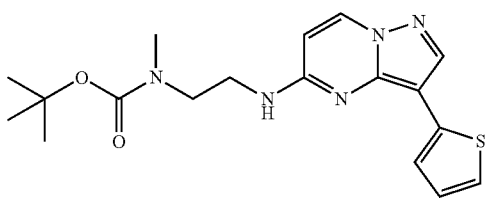 [SMILES: CN(CCNc1ccn2ncc(-c3cccs3)c2n1)C(=O)OC(C)(C)C]

Part A. 3-Oxo-2-thiophen-2-yl-propionitrile

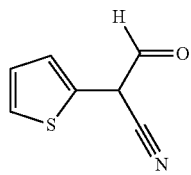

Thiophen-2-yl-acetonitrile [20893-30-5] (6.7 mL, 62.6 mmol) was added to a N$_2$ blanketed, 0° C., stirred solution of 21 wt % sodium ethoxide (25.7 mL, 68.9 mmol) in ethanol (100 mL). After 5 minutes, ethyl formate [109-94-4] (12.6 mL, 156.7 mmol) was added and the resultant solution was stirred for 20 minutes. The ice bath was then removed and replaced with a heating mantle. The reaction was heated to reflux for 2 h, cooled, and evaporated to provide a yellow solid. Crude product was dissolved in water, the solution chilled to 0° C. and acidified with aqueous hydrochloric acid to precipitate an off white powder. Product was isolated by filtration, washed with water, and dried to afford 7.4 g. LRMS (ESI) m/z 152.0 [(M+H)]$^+$, calc'd for $C_7H_6NOS$: 151.19

Part B. 4-Thiophen-2-yl-2H-pyrazol-3-ylamine

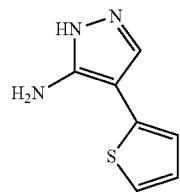 [SMILES: Nc1[nH]ncc1-c1cccs1]

Hydrazine hydrate [7803-57-8] (4.8 mL, 99.0 mmol) then acetic acid [64-19-7] (5.6 mL, 97.8 mmol) were added to a solution of 3-oxo-2-thiophen-2-yl-propionitrile (7.4 g, 49.0 mmol) in ethanol (100 mL). The solution was then heated to reflux for 2 h. The cooled reaction was evaporated to dryness and the resultant solid triturated in water. Product was isolated by filtration, washed with water, and dried to provide 4-thiophen-2-yl-2H-pyrazol-3-ylamine as 7.1 g of fine off white powder, mp. 183-1840° C. $^1$H NMR (400 MHz, DMSO-d$_6$) δ ppm 2.51 (s, 1 H) 7.01-7.10 (m, 2 H) 7.27 (dd, J=5.05, 1.01 Hz, 1 H). $^{13}$C NMR (100 MHz, DMSO-d$_6$) δ ppm 121.07, 121.47, 127.58, 135.85. LRMS (ESI) m/z 166.0 [(M+H)]$^+$, calc'd for C$_7$H$_7$N$_3$S: 165.22.

Part C.
3-Thiophen-2-yl-4H-pyrazolo[1,5-a]pyrimidin-5-one

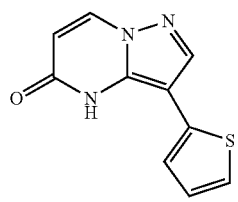 [SMILES: O=c1ccn2ncc(-c3cccs3)c2[nH]1]

A 21 wt % solution of sodium ethoxide in ethanol (32.7 mL, 87.6 mmol) was slowly added to an ambient temperature, stirred suspension of 4-thiophen-2-yl-2H-pyrazol-3-ylamine (4.1 g, 25.0 mmol) and 1,3-dimethylpyrimidine-2,4(1H,3H)-dione [874-14-6] (3.9 g, 27.5 mmol) in ethanol (217 mL). As addition progressed the solid dissolved to give a clear brown solution. The solution was heated to reflux for 2 d, cooled, then poured into 5% (w/v) aqueous ammonium chloride. Ethanol was evaporated out and the reduced volume product solution chilled, with stirring, in an ice bath to precipitate 3-thiophen-2-yl-4H-pyrazolo[1,5-a]pyrimidin-5-one as 3.2 g of red-brown fine crystalline powder, mp. 231-232° C. $^1$H NMR (400 MHz, DMSO-d$_6$) δ ppm 6.13 (br. s., 1 H) 7.10 (dd, J=5.05, 3.54 Hz, 1 H) 7.38-7.46 (m, 2 H) 8.07 (br. s., 1 H) 8.51-8.73 (m, 1 H) 12.06 (br. s., 1 H). $^{13}$C NMR (100 MHz, DMSO-d$_6$) δ ppm 123.66, 127.71, 138.70, 142.47. LRMS (ESI) m/z 218.0 [(M+H)]$^+$, calc'd for C$_{10}$H$_7$N$_3$OS: 217.25.

Part D. Methyl-[2-(3-thiophen-2-yl-pyrazolo[1,5-a]pyrimidin-5-ylamino)-ethyl]-carbamic acid tert-butyl ester

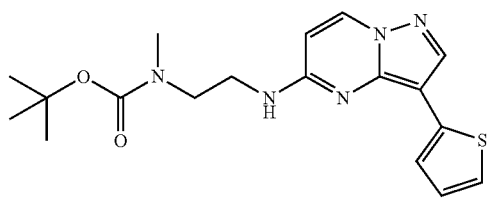 [SMILES: CN(CCNc1ccn2ncc(-c3cccs3)c2n1)C(=O)OC(C)(C)C]

1,8-Diazabicycloundec-7-ene (DBU) [6674-22-2] (0.4 mL, 2.5 mmol) was added to an ambient temperature, stirred, turbid solution of 3-thiophen-2-yl-4H-pyrazolo[1,5-a]pyrimidin-5-one (354.3 mg, 1.6 mmol), (2-amino-ethyl)-methyl-carbamic acid tert-butyl ester [121492-06-6] (852.2 mg, 4.9 mmol), and (benzotriazol-1-yloxy)tris(dimethylamino)phosphonium hexafluorophosphate (BOP) [56602-33-6] (937.7 mg, 2.1 mmol) in acetonitrile (16 mL). Upon addition of the DBU the turbidity clears and the solution was permitted to stir for 2 d then partitioned between brine and ethyl acetate. The extract was dried (MgSO$_4$) and flash chromatographed (silica gel, eluted with 10% (v/v) methanol/ethyl acetate). Evaporation of product fractions yielded an oil which was crystallized from heptane to provide methyl-[2-(3-thiophen-2-yl-pyrazolo[1,5-a]pyrimidin-5-ylamino)-ethyl]-carbamic acid tert-butyl ester as 333.6 mg of yellow, fine crystalline powder, mp. 140-141° C. $^1$H NMR (400 MHz, DMSO-d$_6$) δ ppm (rotomers present) 1.16-1.28 (m, 5 H) 1.37 (br. s., 3 H) 2.51 (s, 1 H) 2.85 (br. s., 3 H) 3.47 (br. s., 1 H) 3.55 (br. s., 3 H) 6.28 (d, J=6.82 Hz, 1 H) 7.04 (dd, J=5.05, 3.54 Hz, 1 H) 7.30 (dd, J=5.05, 1.01 Hz, 1H) 7.41 (br. s., 1 H) 7.80 (br. s., 1 H) 8.19 (s, 1 H) 8.48 (d, J=7.07 Hz, 1 H). $^{13}$C NMR (100 MHz, DMSO-d$_6$) δ ppm 27.81, 27.96, 33.75, 38.41, 46.32, 78.13, 100.28, 100.76, 120.16, 121.75, 126.90, 135.01, 135.20, 140.78, 143.74, 154.91, 155.81. LRMS (ESI) m/z 374.1 [(M+H)]$^+$, calc'd for C$_{18}$H$_{23}$N$_5$O$_2$S: 373.48.

5.6.5. Synthesis of Isopropyl (2-((3-(3-methoxypyridin-4-yl)pyrazolo[1,5-a]pyrimidin-5-yl)amino)ethyl) (methyl)-carbamate

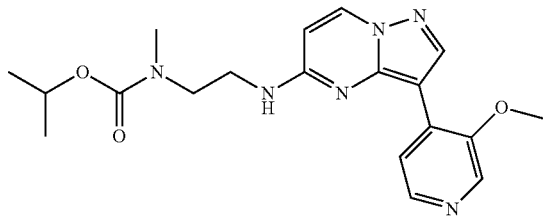 [SMILES: COc1cnccc1-c1cnn2ccc(NCCN(C)C(=O)OC(C)C)nc12]

Part A. 3-Bromo-5-chloro-pyrazolo[1,5-a]pyrimidine

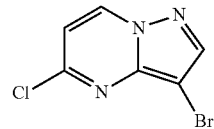 [SMILES: Clc1ccn2ncc(Br)c2n1]

Sodium acetate [127-09-3] (24.1 g, 293.9 mmol) was added to a solution of 5-chloro-pyrazolo[1,5-a]pyrimidine [29274-24-6], (30.1 g, 195.7 mmol) in glacial acetic acid (395 mL) and allowed to stir at ambient temperature until all of the solid had dissolved. An ice bath was then put in place, and the solution chilled to 0° C. Bromine [7726-95-6] (11.0 mL, 214.7 mmol) was added drop by drop into the 0° C. buffered acetic acid reaction solution over 35 minutes which gradually became a thick stirred suspension. Upon completion of the bromine addition, the suspension was allowed to stir for a further 15 minutes then was slowly poured into an aqueous (5% w/v) solution (1 L) of sodium metabisulfite [7681-57-4] stirred in an ice bath. Solid sodium hydroxide [1310-73-2] pellets were added to the stirred suspension, at a rate to maintain an internal temperature of less than 40° C., until pH of the supernatant was determined to be approximately 8 by pH paper. Precipitated product was isolated by filtration, the filter cake washed with water, and allowed to dry to afford 39.8 g of light yellow powder, mp. 173-174° C. $^1$H NMR (400 MHz, DMSO-d$_6$) δ ppm 7.22 (d, J=7.33 Hz, 1 H) 8.44 (s, 1 H) 9.21 (d, J=7.07 Hz, 1 H). $^{13}$C NMR (100 MHz, DMSO-d$_6$) δ ppm 82.84, 109.99, 138.94, 143.76, 145.61, 151.18. LRMS (ESI) m/z 231.8/233.8/235.8 [(M+H)]⁺, calc'd for $C_6H_3BrClN_3$: 232.47.

Part B. tert-butyl (2-((3-bromopyrazolo[1,5-a]pyrimidin-5-yl)amino)ethyl)(methyl)carbamate

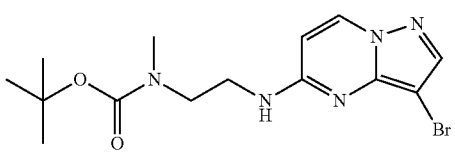 [SMILES: CN(CCNc1ccn2ncc(Br)c2n1)C(=O)OC(C)(C)C]

To 465 mg (2.00 mmol) of 3-bromo-5-chloropyrazolo[1,5-a]pyrimidine was added tert-butyl (2-aminoethyl)(methyl)carbamate (522 mg, 3.00 mmol), 4 mL of isopropanol, and triethylamine (0.56 mL, 4.00 mmol). The resulting mixture is heated at 140° C. for 0.5 hr in the microwave. It was diluted with EtOAc, and washed with water and brine. The organic layer was dried over MgSO₄, concentrated and purified on the silica gel column eluting with 20-100% EtOAc/Hex to obtain 607 mg (82%) of the desired product.

Part C. N1-(3-bromopyrazolo[1,5-a]pyrimidin-5-yl)-N2-methylethane-1,2-diamine

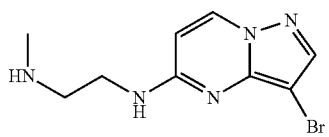

The tert-butoxycarbonyl was removed by dissolving 600 mg (1.62 mmol) of tert-butyl (2-((3-bromopyrazolo[1,5-a]pyrimidin-5-yl)amino)ethyl)(methyl)carbamate in 4 mL of DCM, and then adding 4 mL TFA, stirring for 0.5 hr at rt, and concentrating the mixture to afford the TFA-salt of the desired product in 100% yield (622 mg).

Part D. Isopropyl (2-((3-bromopyrazolo[1,5-a]pyrimidin-5-yl)amino)ethyl)(methyl)carbamate

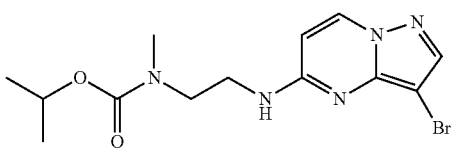 [SMILES: CC(C)OC(=O)N(C)CCNc1ccn2ncc(Br)c2n1]

To 1.0 equivalent (384 mg, 1.000 mmol) of the amine (TFA salt) dissolved 20 mL of DCM was added 3.0 equivalents (368 mg, 3.000 mmol) of isopropylchloroformate, 4.0 equivalents triethylamine (404 mg, 4.000 mmol). The resulting mixture was stirred at rt for 0.5 hr, and then diluted with DCM (30 mL) washed with water and brine, dried over MgSO₄, and concentrated. The crude residue was purified in the silica gel (ISCO) eluting with 1-10% MeOH/DCM to obtain the desired product (87% yield).

Part E. Isopropyl (2-((3-(3-methoxypyridin-4-yl)pyrazolo[1,5-a]pyrimidin-5-yl)amino)ethyl)(methyl)-carbamate

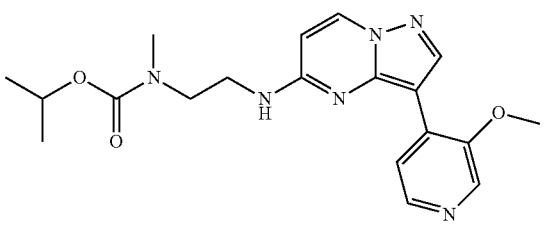 [SMILES: COc1cnccc1-c1cnn2ccc(NCCN(C)C(=O)OC(C)C)nc12]

To 80 mg (0.22 mmol) of isopropyl (2-((3-bromopyrazolo[1,5-a]pyrimidin-5-yl)amino)ethyl)(methyl)-carbamate was added (3-methoxypyridin-4-yl)boronic acid dihydrate (56 mg, 0.27 mmol), K₃PO₄ (143 mg, 0.67 mmol), PdCl₂(PPh₃)₂ (16.8 mg, 0.022 mmol), 3 mL of DME and 1 mL of water. This mixture was microwaved at 140° C. for 0.5 hr. After cooling, it was diluted with EtOAc, and washed with water and brine. The organic layer was dried over MgSO₄, concentrated, and purified on the PREP HPLC to afford the desired product in 77% yield (66.4 mg). ¹H NMR (400 MHz, Acetone) δ ppm 2.87 (br. s., 3 H) 2.99 (br. s., 3 H) 3.58-3.71 (m, 2 H) 3.73-3.82 (m, 2 H) 4.09 (s, 3 H) 4.82 (td, J=6.25, 2.91 Hz, 1 H) 6.45 (br. s., 1 H) 8.21 (br. s., 1 H) 8.35 (s, 1 H) 8.43 (d, J=6.06 Hz, 1 H) 8.58 (s, 1 H) 8.77 (br. s., 1 H); LRMS (ESI) m/e 385.0 [(M+H)⁺, calcd for $C_{19}H_{24}N_6O_3$ 384.0].

5.6.6. Synthesis of (5)-tert-butyl 2-(((3-(4-(aminomethyl)phenyl)pyrazolo[1,5-a]pyrimidin-5-yl)amino)methyl)pyrrolidine-1-carboxylate Part A. (S)-tert-butyl 2-(((3-bromopyrazolo[1,5-a]pyrimidin-5-yl)amino)methyl)pyrrolidine-1-carboxylate

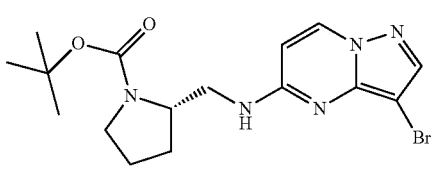 [SMILES: CC(C)(C)OC(=O)N1CCC[C@H]1CNc1ccn2ncc(Br)c2n1]

The reaction of 3-bromo-5-chloropyrazolo[1,5-a]pyrimidine and (S)-tert-butyl 2-(aminomethyl)pyrrol-idine-1-carboxylate under the amine displacement conditions described in example 5.6.5 afforded 74% product.

Part B. (S)-tert-butyl 2-(((3-(4-(aminomethyl)phenyl) pyrazolo[1,5-a]pyrimidin-5-yl)amino)methyl)-pyrrolidine-1-carboxylate

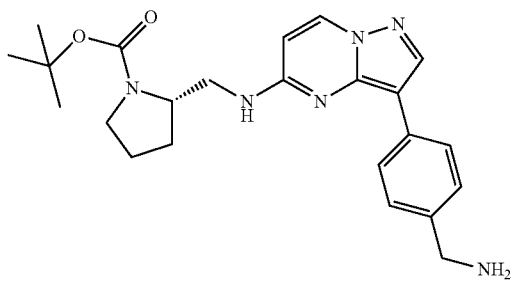 [SMILES: CC(C)(C)OC(=O)N1CCC[C@H]1CNc1ccn2ncc(-c3ccc(CN)cc3)c2n1]

The Suzuki coupling of (5)-tert-butyl 2-(((3-bromopyrazolo[1,5-a]pyrimidin-5-yl)amino)methyl)pyrrolidine-1-carboxylate with (4-(aminomethyl)phenyl)boronic acid under the same conditions as described in example 5.6.5 to give 73% of the titled compound. $^1$H NMR (400 MHz, METHANOL-$d_4$) δ ppm 1.44 (br. s., 9 H) 1.90 (dd, J=9.92, 5.51 Hz, 1 H) 1.96-2.11 (m, 3 H) 3.35-3.45 (m, 4 H) 4.07-4.21 (m, 3 H) 6.33 (br. s., 1 H) 7.46 (d, J=8.38 Hz, 2 H) 8.19 (br. s., 2 H) 8.25-8.36 (m, 2 H); LRMS (ESI) m/e 423.0 [(M+H)$^+$, calcd for $C_{23}H_{30}N_6O_2$ 422.0].

5.6.7. Synthesis of (5)-tert-butyl 2-(((3-(2-methoxyphenyl)pyrazolo[1,5-a]pyrimidin-5-yl)amino)methyl)pyrrolidine-1-carboxylate

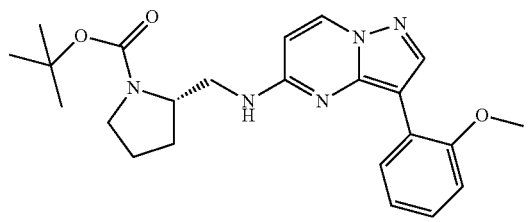 [SMILES: COc1ccccc1-c1cnn2ccc(NC[C@@H]3CCCN3C(=O)OC(C)(C)C)nc12]

The Suzuki coupling of (5)-tert-butyl 2-(((3-bromopyrazolo[1,5-a]pyrimidin-5-yl)amino)methyl)pyrrolidine-1-carboxylate with (2-methoxyphenyl)boronic acid under the same conditions as described in example 5.6.5 to give 68% of the titled compound. $^1$H NMR (400 MHz, CHLOROFORM-d) δ ppm 1.50 (s, 9 H) 1.85-2.12 (m, 4 H) 3.40 (dd, J=7.58, 4.04 Hz, 2 H) 3.46-3.59 (m, 1 H) 3.59-3.67 (m, 1 H) 3.94 (s, 3 H) 4.19 (br. s., 1 H) 6.07 (d, J=7.07 Hz, 1 H) 6.99 (d, J=7.58 Hz, 1 H) 7.06 (td, J=7.45, 1.01 Hz, 1 H) 7.15-7.22 (m, 1 H) 8.14-8.28 (m, 1 H) 8.45 (d, J=6.82 Hz, 1 H) 8.51 (s, 1 H); LRMS (ESI) m/e 424.0 [(M+H)$^+$, calcd for $C_{23}H_{29}N_5O_3$ 423.0].

5.6.8. Synthesis of (5)-tert-butyl 2-(((3-(trifluoromethyl)pyrazolo[1,5-a]pyrimidin-5-yl)amino)methyl) pyrrolidine-1-carboxylate

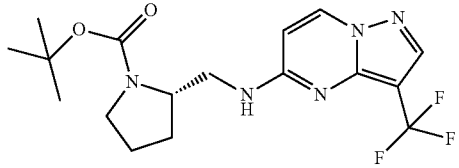

Part A. (S)-tert-butyl 2-((pyrazolo[1,5-a]pyrimidin-5-ylamino)methyl)pyrrolidine-1-carboxylate

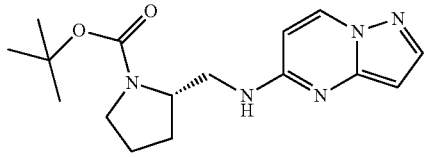 [SMILES: CC(C)(C)OC(=O)N1CCC[C@H]1CNc1ccn2nccc2n1]

The commercially available 5-chloropyrazolo[1,5-a]pyrimidine is reacted with (S)-tert-butyl 2-(aminomethyl)pyrrolidine-1-carboxylate under the amine displacement conditions described in example 5.6.5 to give 96% product.

Part B. (S)-tert-butyl 2-(((3-iodopyrazolo[1,5-a]pyrimidin-5-yl)amino)methyl)pyrrolidine-1-carboxylate

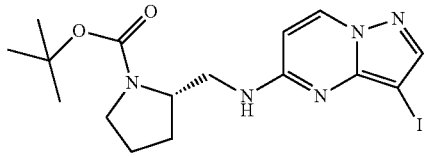 [SMILES: CC(C)(C)OC(=O)N1CCC[C@H]1CNc1ccn2ncc(I)c2n1]

The (S)-tert-butyl 2-((pyrazolo[1,5-a]pyrimidin-5-ylamino)methyl)pyrrolidine-1-carboxylate (790 mg, 2.490 mmol) was dissolved in 10 mL of DMF, was added NIS (617 mg, 2.740 mmol). This mixture is stirred for 4 hr at rt, and then quenched with 10 mL of water. It was then diluted with 50 mL EtOAc and the organic layer was separated, washed twice with brine, and dried over MgSO$_4$. It was concentrated and purified on the silica gel eluting with 20-100% EtOAc/hex to obtain 1.03 g (93%) an off-white solid.

Part C. (S)-isopropyl 2-(((3-(trifluoromethyl)pyrazolo[1,5-a]pyrimidin-5-yl)amino)methyl)pyrrolidine-1-carboxylate

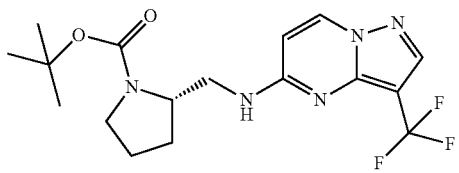 [SMILES: CC(C)(C)OC(=O)N1CCC[C@H]1CNc1ccn2ncc(C(F)(F)F)c2n1]

To 221.5 mg (0.50 mmol) of the aryl iodide dissolved in 2 mL DMF was added methyl 2,2-difluoro-2-(fluorosulfonyl)acetate (0.77 g, 4.00 mmol), CuI (762 mg, 2.00 mmol), HMPA (0.41 mL, 3.50 mmol). This mixture was stirred on an oil bath preheated to 90° C. for 0.75 hr. The reaction was cooled to rt, and quenched with NH$_4$Cl saturated aqueous solution. Extracted with 30 mL of EtOAc, washed with brine and dry over MgSO$_4$. It was concentrated and purified on the PREP HPLC to obtain 81 mg (42%) of the desired product. $^1$H NMR (400 MHz, METHANOL-d$_4$) δ ppm 1.44 (s, 9 H) 1.86-1.99 (m, 3 H) 1.99-2.07 (m, 1 H) 3.40 (br. s., 3 H) 3.61 (br. s., 1 H) 4.11 (br. s., 1 H) 6.37 (br. s., 1 H) 7.98 (s, 1 H) 8.33 (br. s., 1 H); LRMS (ESI) m/e 386.0 [(M+H)$^+$, calcd for C$_{17}$H$_{22}$F$_3$N$_5$O$_2$ 385.0].

5.6.9. Synthesis of 4-[3-(3-Methoxy-pyridin-4-yl)-pyrazolo[1,5-a]pyrimidin-5-yl]-piperazine-1-carboxylic acid isopropyl ester

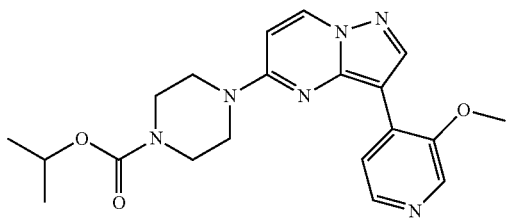 [SMILES: COc1cnccc1-c1cnn2ccc(N3CCN(C(=O)OC(C)C)CC3)nc12]

Part A.
3-Bromo-5-piperazin-1-yl-pyrazolo[1,5-a]pyrimidine

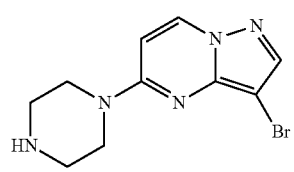 [SMILES: Brc1cnn2ccc(N3CCNCC3)nc12]

3-Bromo-5-chloro-pyrazolo[1,5-a]pyrimidine (15.4 g, 66.2 mmol) and piperazine [110-85-0] (56.8 g, 659.5 mmol) were ground together in a mortar to an intimate mixture and transferred to a 250 mL round bottomed flask containing a magnetic stir bar. The flask was fitted to a reflux condenser, N$_2$ blanketed, and the reaction pot immersed in an ambient temperature oil bath. While the neat solid mixture stirred, the bath was heated to 120° C. over 0.5 h and held at nominal temperature for a total of 2 h. The bath was removed and the molten reaction allowed to cool to approximately 75° C. Ethyl acetate was cautiously added down the condenser to dissolve the reaction product to prevent its setting up into a solid mass. The reaction solution was transferred to a separatory funnel, further diluted with ethyl acetate, and washed with water. The ethyl acetate extract was dried (MgSO$_4$) and evaporated to obtain 16.1 g of clear yellow oil. The oil was crystallized from methanol to provide 15.8 g of light yellow crystalline powder in two crops, mp. 108-109° C. $^1$H NMR (400 MHz, DMSO-d$_6$) δ ppm 2.51 (s, 1 H) 3.16-3.24 (m, 3 H) 3.38 (s, 1 H) 3.93-4.00 (m, 3 H) 6.85 (d, J=7.83 Hz, 1 H) 8.03 (s, 1 H) 8.78 (d, J=8.08 Hz, 1 H) 9.61 (br. s., 1 H). $^{13}$C NMR (100 MHz, DMSO-d$_6$) δ ppm 41.25, 42.16, 77.73, 97.78, 136.77, 144.01, 144.18, 155.53. LRMS (ESI) m/z 282.0/284.0 [(M+H)]$^+$, calc'd for C$_{10}$H$_{12}$BrN$_5$: 282.14.

Part B. 4-(3-Bromo-pyrazolo[1,5-a]pyrimidin-5-yl)-piperazine-1-carboxylic acid isopropyl ester

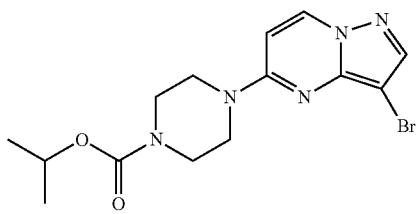 [SMILES: CC(C)OC(=O)N1CCN(c2ccn3ncc(Br)c3n2)CC1]

To a rapidly stirred, 0° C., N$_2$ blanketed, solution of 3-bromo-5-piperazin-1-yl-pyrazolo[1,5-a]pyrimidine (15.8 g, 56.0 mmol) and Hunig's base [7087-68-5] (20.0 mL, 114.8 mmol) in ethyl acetate (280 mL) was steadily added a 1.0M solution of isopropyl chloroformate in toluene (67.0 mL) over the course of 10 minutes. The reaction was allowed to stir and warm to ambient temperature over night at which time it was washed with brine, dried (MgSO$_4$), preloaded onto silica gel, chromatographed (Silica gel, eluted with 100% ethyl acetate) and crystallized from ethyl acetate/heptane to afford 13.2 g of white powder, mp. 78-79° C. $^1$H NMR (400 MHz, DMSO-d$_6$) δ ppm 1.22 (d, J=6.32 Hz, 6 H) 3.44-3.54 (m, 4 H) 3.67-3.79 (m, 4 H) 4.82 (spt, J=6.23 Hz, 1 H) 6.77 (d, J=7.83 Hz, 1 H) 7.97 (s, 1 H) 8.69 (d, J=7.83 Hz, 1 H). $^{13}$C NMR (100 MHz, DMSO-d$_6$) δ ppm 21.94, 42.80, 43.87, 68.17, 77.32, 97.66, 136.47, 143.87, 144.40, 154.29, 155.64. LRMS (ESI) m/z 368.0/370.0 [(M+H)]$^+$, calc'd for C$_{14}$H$_{18}$BrN$_5$O$_2$: 368.24.

Part C. 4-[3-(3-Methoxy-pyridin-4-yl)-pyrazolo[1,5-a]pyrimidin-5-yl]-piperazine-1-carboxylic acid isopropyl ester

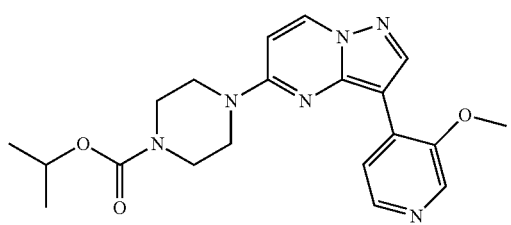 [SMILES: COc1cnccc1-c1cnn2ccc(N3CCN(C(=O)OC(C)C)CC3)nc12]

To a mixture of 4-(3-bromo-pyrazolo[1,5-a]pyrimidin-5-yl)-piperazine-1-carboxylic acid isopropyl ester (385.0 mg, 1.1 mmol), 3-methoxypyridine-4-boronic acid hydrate [1072952-50-1] (229.7 mg, 1.34 mmol), potassium phosphate tribasic monohydrate [27176-10-9] (516.3 mg, 2.2 mmol), and [1,1'-bis(diphenylphosphino)ferrocene]dichloropalladium(II), complex with dichloromethane [95464-05-4] (102.4 mg, 0.1 mmol) contained in a 50 mL round bottomed flask was added a solution of 30% (v/v) water in 1,2-dimethoxyethane (25 mL) and a magnetic stir bar. The reaction pot was fitted to a reflux condenser, lowered into an ambient temperature oil bath, and the system taken through 10 evacuation/$N_2$ blanket cycles while being rapidly stirred. The rapidly stirred, $N_2$ blanketed, reaction was heated to an oil bath temperature of 85° C. for 17 h then cooled and partitioned between brine (pH adjusted to 10 with 3N aqueous sodium hydroxide) and ethyl acetate. The phase separated extract was dried ($MgSO_4$) and evaporated to afford an orange oil which was purified by preparative RP-HPLC. Isolated product was dissolved in methanol, diluted with concentrated hydrochloric acid, evaporated to dryness, redissolved in methanol and precipitated by the addition of diethyl ether. Filtration of the precipitate yielded 100.5 mg of the product monohydrochloride salt as a yellow powder. mp. 206-207° C. (dec.) $^1$H NMR (400 MHz, DMSO-$d_6$) δ ppm 1.23 (d, J=6.39 Hz, 6 H) 2.51 (s, 2 H) 3.53-3.59 (m, 4 H) 3.85 (br. s., 3 H) 4.13 (s, 3 H) 4.84 (spt, J=6.25 Hz, 1 H) 6.96 (d, J=7.94 Hz, 1 H) 8.42 (d, J=6.39 Hz, 1 H) 8.48 (s, 1 H) 8.76 (s, 1 H) 8.86 (d, J=7.94 Hz, 1H) 9.06 (d, J=6.17 Hz, 1H). $^{13}$C NMR (100 MHz, DMSO-$d_6$) δ ppm 21.97, 42.79, 44.23, 57.17, 68.25, 97.56, 98.39, 120.03, 123.90, 137.27, 137.05, 137.95, 146.48, 147.00, 151.80, 154.26, 156.66. LRMS (ESI) m/z 397.1 [(M+H)]$^+$, calc'd for $C_{20}H_{24}N_6O_3$: 396.45.

5.6.10. Synthesis of 4-[3-(2-Methoxy-phenyl)-pyrazolo[1,5-a]pyrimidin-5-yl]-piperazine-1-carboxylic acid isopropyl ester

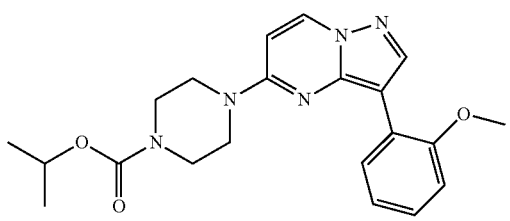 [SMILES: COc1ccccc1-c1cnn2ccc(N3CCN(C(=O)OC(C)C)CC3)nc12]

Prepared similarly to the preparation of example 5.6.9 from 4-(3-bromo-pyrazolo[1,5-a]pyrimidin-5-yl)-piperazine-1-carboxylic acid isopropyl ester (385.0 mg, 1.1 mmol) and 2-methoxyphenylboronic acid [5720-06-9] (191.8 mg, 1.3 mmol) to afford 76.4 mg of yellow powder as a free base, mp. 57-59° C. $^1$H NMR (400 MHz, DMSO-$d_6$) δ ppm 1.22 (d, J=6.32 Hz, 6 H) 3.48-3.54 (m, 4 H) 3.68-3.77 (m, 4 H) 3.87 (s, 3 H) 4.77-4.85 (m, 1 H) 6.76 (d, J=7.83 Hz, 1 H) 6.94-7.07 (m, 2 H) 7.10-7.18 (m, 1 H) 8.38 (dd, J=7.71, 1.64 Hz, 1 H) 8.43 (s, 1 H) 8.71 (d, J=8.08 Hz, 1 H). $^{13}$C NMR (100 MHz, DMSO-$d_6$) δ ppm 21.95, 44.07, 55.32, 68.14, 96.93, 101.10, 111.29, 120.48, 121.64, 125.83, 127.67, 136.28, 145.00, 154.31, 155.25, 155.51. LRMS (ESI) m/z 396.1 [(M+H)]$^+$, calc'd for $C_{21}H_{26}N_6O_3$: 395.47.

5.6.11. Synthesis of (5)-tert-butyl 2-(((3-(2-ethylphenyl)pyrazolo[1,5-a]pyrimidin-5-yl)amino)methyl)pyrrolidine-1-carboxylate

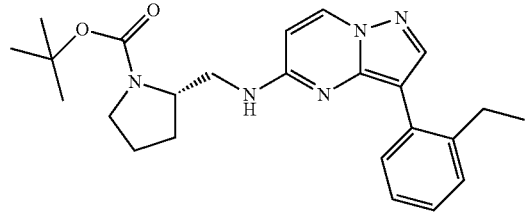 [SMILES: CCc1ccccc1-c1cnn2ccc(NC[C@@H]3CCCN3C(=O)OC(C)(C)C)nc12]

The Suzuki coupling of (5)-tert-butyl 2-(((3-bromopyrazolo[1,5-a]pyrimidin-5-yl)amino)methyl)pyrrolidine-1-carboxylate with (2-ethylphenyl)boronic acid under the same conditions as described in example 5.6.5 to give 77% of the titled compound. $^1$H NMR (400 MHz, CHLOROFORM-d) δ ppm 1.20 (t, J=7.58 Hz, 3 H) 1.49 (s, 9 H) 1.79-1.95 (m, 3 H) 1.95-2.05 (m, 1 H) 2.82 (q, J=7.58 Hz, 2 H) 3.34-3.44 (m, 3 H) 3.44-3.53 (m, 1 H) 4.15 (br. s., 1 H) 6.08 (d, J=6.82 Hz, 1 H) 7.23-7.31 (m, 3 H) 7.32-7.38 (m, 1 H) 7.51 (dd, J=7.20, 1.39 Hz, 1 H) 7.91 (s, 1 H) 8.20 (d, J=6.32 Hz, 1 H); LRMS (ESI) m/e 422.0 [(M+H)]$^+$, calcd for $C_{24}H_{31}N_5O_2$ 421.0].

5.6.12. Synthesis of (5)-tert-butyl 2-(((3-(2-[D3]methoxy phenyl)pyrazolo[1,5-a]pyrimidin-5-yl)amino)methyl)pyrrolidine-1-carboxylate

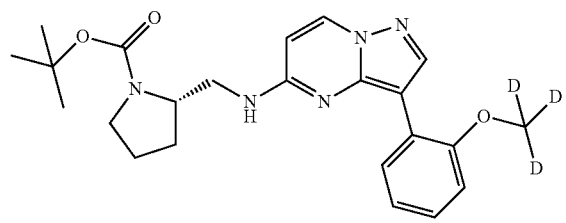 [SMILES: [2H]C([2H])([2H])Oc1ccccc1-c1cnn2ccc(NC[C@@H]3CCCN3C(=O)OC(C)(C)C)nc12]

Part A. 2-(2-[D3]methoxyphenyl)-4,4,5,5-tetramethyl-1,3,2-dioxaborolane

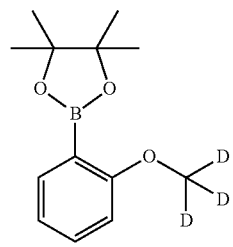 [SMILES: [2H]C([2H])([2H])Oc1ccccc1B1OC(C)(C)C(C)(C)O1]

To the 2-(4,4,5,5-tetramethyl-1,3,2-dioxaborolan-2-yl) phenol (100 mg, 0.455 mmol) dissolved in 6 mL of DMSO was added deuterated methyl iodine (132 mg, 0.909 mmol) followed by 60% NaH (22 mg, 0.909 mmol). The resulting mixture was stirred overnight at rt. Dilute with 25 mL EtOAc, and wash with water and brine. Dry over MgSO4 and concentrate to give 108 mg (100%) of the ether product.

Part B. (S)-tert-butyl 2-(((3-(2-[D3]methoxy phenyl) pyrazolo[1,5-a]pyrimidin-5-yl)amino)methyl)-pyrrolidine-1-carboxylate

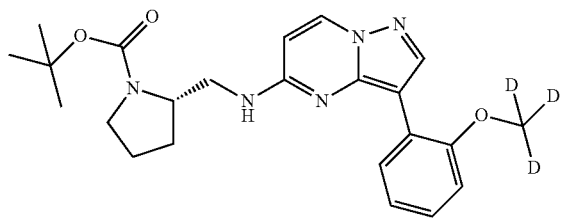 [SMILES: [2H]C([2H])([2H])Oc1ccccc1-c1cnn2ccc(NC[C@@H]3CCCN3C(=O)OC(C)(C)C)nc12]

The reaction of the 2-(2-[D3]methoxy phenyl)-4,4,5,5-tetramethyl-1,3,2-dioxaborolane with (S)-tert-butyl 2-(((3-bromopyrazolo[1,5-a]pyrimidin-5-yl)amino)methyl)pyrrolidine-1-carboxylate under Suzuki conditions described in example 5.6.5 afforded the titled compound in 70% yield. $^1$H NMR (400 MHz, CHLOROFORM-d) δ ppm 1.51 (s, 9 H) 1.83-2.11 (m, 4 H) 3.40 (dd, J=7.45, 3.92 Hz, 2 H) 3.47-3.59 (m, 1 H) 3.59-3.66 (m, 1 H) 4.20 (br. s., 1 H) 6.07 (d, J=7.07 Hz, 1 H) 6.96-7.02 (m, 1 H) 7.06 (td, J=7.52, 1.14 Hz, 1 H) 7.15-7.24 (m, 1 H) 8.19 (d, J=6.32 Hz, 1 H) 8.46 (d, J=6.82 Hz, 1 H) 8.51 (s, 1H); LRMS (ESI) m/e 427.0 [(M+H)$^+$, calcd for C$_{23}$H$_{26}$D3N$_5$O$_3$ 426.0].

5.6.13. Synthesis of 4-[3-(2-Methoxy-pyridin-3-yl)-pyrazolo[1,5-a]pyrimidin-5-yl]-piperazine-1-carboxylic acid isopropyl ester

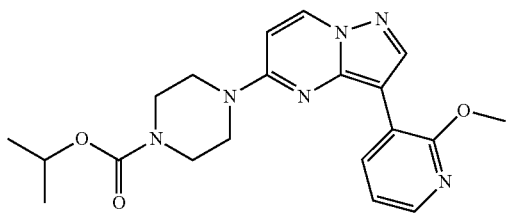 [SMILES: COc1ncccc1-c1cnn2ccc(N3CCN(C(=O)OC(C)C)CC3)nc12]

Prepared similarly to the preparation of example 5.6.9 from 4-(3-bromo-pyrazolo[1,5-a]pyrimidin-5-yl)-piperazine-1-carboxylic acid isopropyl ester (338.7 mg, 0.9 mmol) and 2-methoxy-3-pyridineboronic acid [163105-90-6] (169.4 mg, 1.1 mmol) to afford 76.0 mg of yellow powder as a free base, mp. 131-132° C. $^1$H NMR (400 MHz, DMSO-d$_6$) δ ppm 1.22 (d, J=6.06 Hz, 6 H) 3.47-3.56 (m, 4 H) 3.71-3.80 (m, 4 H) 4.00 (s, 3 H) 4.82 (spt, J=6.23 Hz, 1 H) 6.81 (d, J=8.08 Hz, 1 H) 7.08 (dd, J=7.45, 4.93 Hz, 1 H) 7.98 (dd, J=4.93, 1.89 Hz, 1 H) 8.51 (s, 1 H) 8.76 (d, J=7.83 Hz, 1 H) 8.82 (dd, J=7.58, 2.02 Hz, 1H). $^{13}$C NMR (100 MHz, DMSO-d$_6$) δ ppm 21.95, 42.85, 44.06, 53.10, 68.16, 97.21, 98.90, 116.40, 117.17, 134.55, 136.43, 141.99, 144.65, 144.71, 154.26, 155.46, 158.89. LRMS (ESI) m/z 397.1 [(M+H)]$^+$, calc'd for C$_{20}$H$_{24}$N$_6$O$_3$: 396.45.

5.6.14. Synthesis of 4-[3-(1-Methyl-2-oxo-1,2-dihydro-pyridin-3-yl)-pyrazolo[1,5-a]pyrimidin-5-yl]-piperazine-1-carboxylic acid isopropyl ester

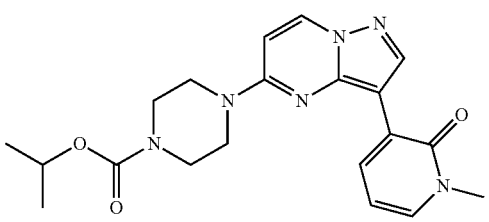 [SMILES: CC(C)OC(=O)N1CCN(c2ccn3ncc(-c4cccn(C)c4=O)c3n2)CC1]

Prepared similarly to the preparation of example 5.6.9 from 4-(3-bromo-pyrazolo[1,5-a]pyrimidin-5-yl)-piperazine-1-carboxylic acid isopropyl ester and (1-methyl-2-oxo-1,2-dihydropyridin-3-yl)boronic acid to provide a yellow powder as a free base, mp. 206-207° C. $^1$H NMR (400 MHz, DMSO-d$_6$) δ ppm 1.23 (d, J=6.32 Hz, 6 H) 3.53 (s, 7 H) 3.70-3.82 (m, 4 H) 4.83 (spt, J=6.23 Hz, 1 H) 6.37 (t, J=6.82 Hz, 1 H) 6.78 (d, J=7.83 Hz, 1 H) 7.55 (dd, J=6.57, 1.26 Hz, 1 H) 8.64 (dd, J=7.20, 1.14 Hz, 1 H) 8.72 (d, J=7.83 Hz, 1 H) 8.96 (s, 1 H). $^{13}$C NMR (100 MHz, DMSO-d$_6$) δ ppm 21.97, 37.39, 42.84, 44.11, 68.16, 96.94, 100.56, 105.49, 122.80, 132.49, 135.00, 136.42, 144.40, 144.56, 154.29, 155.46, 160.29. LRMS (ESI) m/z 397.1 [(M+H)]$^+$, calc'd for C$_{20}$H$_{24}$N$_6$O$_3$: 396.45.

5.6.15. Synthesis of 4-[3-(3-Fluoro-2-methoxy-phenyl)-pyrazolo[1,5-a]pyrimidin-5-yl]-piperazine-1-carboxylic acid isopropyl ester

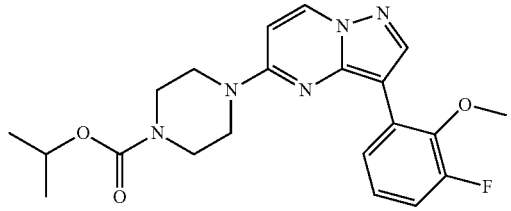 [SMILES: COc1c(F)cccc1-c1cnn2ccc(N3CCN(C(=O)OC(C)C)CC3)nc12]

Prepared similarly to the preparation of example 5.6.9 from 4-(3-bromo-pyrazolo[1,5-a]pyrimidin-5-yl)-piperazine-1-carboxylic acid isopropyl ester (389.9 mg, 1.1 mmol) and 3-fluoro-2-methoxyphenylboronic acid [762287-59-2] (216.2 mg, 1.3 mmol) to afford 153.8 mg of light yellow powder as a free base, mp. 52-53° C. $^1$H NMR (400 MHz, DMSO-d$_6$) δ ppm 1.22 (d, J=6.32 Hz, 6 H) 3.49-3.56 (m, 4 H) 3.75 (dd, J=6.44, 4.17 Hz, 4 H) 3.83 (d, J=1.01 Hz, 3H) 4.82 (spt, J=6.23 Hz, 1 H) 6.81 (d, J=8.08 Hz, 1 H) 7.06 (ddd, J=11.37, 8.08, 1.52 Hz, 1 H) 7.16 (td, J=8.08, 5.81 Hz, 1 H) 8.23 (dt, J=7.89, 1.36 Hz, 1 H) 8.42 (s, 1 H). $^{19}$F NMR (377 MHz, DMSO-d$_6$) δ ppm −131.42. $^{13}$C NMR (100 MHz, DMSO-d$_6$) δ ppm 21.95, 42.83, 44.05, 60.38, 68.16, 97.24, 99.94, 99.98, 112.72, 112.90, 123.22, 124.06, 127.98, 136.39, 143.40, 143.51, 144.25, 144.49, 154.28, 154.63, 155.53, 157.04. LRMS (ESI) m/z 414.1 [(M+H)]$^+$, calc'd for $C_{21}H_{24}FN_5O_3$: 413.46.

5.6.16. Synthesis of Isopropyl 4-(3-(2-fluoropyridin-3-yl)pyrazolo[1,5-a]pyrimidin-5-yl)piperazine-1-carboxylate

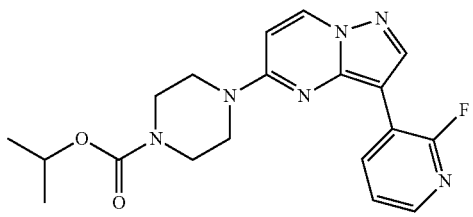 [SMILES: CC(C)OC(=O)N1CCN(c2ccn3ncc(-c4cccnc4F)c3n2)CC1]

Isopropyl 4-(3-bromopyrazolo[1,5-a]pyrimidin-5-yl)piperazine-1-carboxylate (4 g, 10.86 mmol), 2-fluoropyridine-3-boronic acid hydrate (3.44 g, 21.7 mmol), potassium carbonate (4.5 g, 32.6 mmol), Pd(OAc)$_2$ (24 mg, 0.1086 mmol), and x-Phos (146 mg, 0.217 mmol) were taken up in dioxane and water under nitrogen and stirred at 80° C. for 2 hours. Reaction then cooled to room temperature, filtered through celited plug with ethyl acetate. Reduced in vacuo and run through an isco silica column with hexane:ethyl acetate 75-100%. Product plus desbromo co elute, reduced in vacuo. Product recrystallized 3 times from IPAC, washed with heptanes dried to get 889 mg product. $^1$H NMR (400 MHz, DMSO-d6) δ 8.95 (t, J=2.15 Hz, 1 H), 8.78 (d, J=7.83 Hz, 1 H), 8.29 (d, J=4.29 Hz, 1 H), 8.00 (d, J=4.80 Hz, 1 H), 7.43 (dt, J=2.40, 4.99 Hz, 1 H), 6.85 (d, J=7.83 Hz, 1 H), 4.78-4.87 (m, 1 H), 3.73-3.83 (m, 4 H), 3.48-3.58 (m, 4 H), 3.31 (s, 1 H), 1.22 (d, J=6.06 Hz, 6 H) LRMS (ESI) m/z 385 [(M+H)]$^+$, calc'd for $C_{19}H_{21}FN_6O_2$: 384.42.

5.6.17. Synthesis of Isopropyl 4-(3-(5-fluoro-2-methoxypyridin-3-yl)pyrazolo[1,5-a]pyrimidin-5-yl)piperazine-1-carboxylate

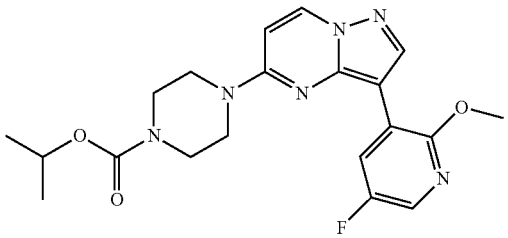

To a 200 mL round bottom flask was added 4.00 g (10.87 mmol) of isopropyl 4-(3-bromopyrazolo[1,5-a]pyrimidin-5-yl)piperazine-1-carboxylate, 2.89 g (11.41 mmol) of (5-fluoro-2-methoxypyridin-3-yl)boronic acid, 0.38 g (0.33 mmol) of Pd(PPh$_3$)$_4$, and a stirring rod. After adding all the solids, 60 ml of 2% TPGS-750-M solution was added, followed by the addition of 7.56 mL (54.35 mmol) triethylamine.

The reaction flask was plunged into an oil bath pre-heated to 90° C., and stirred vigorously. It took about 0.25 hr of stirring for all the suspended solids to dissolve completely. Several color changes were observed, the last color that remained through the rest of the reaction was a very dark brown color.

After 1.5 hr, LCMS showed that reaction was complete. It was allowed to cool to RT, and diluted with 100 mL EtOAc. The organic layer was separated, and the aqueous layer was extracted twice with 40 mL EtOAc portions. The combined organic layers was washed with brine, dried over MgSO$_4$, and concentrated. A small volume of DCM was used to dissolve the crude mixture, and then loaded directly onto a 120 g silica gel column for separation on the ISCO. A gradient of 40% EtOAc/hex to 100% EtOAc was run for the first 25 minutes. The desired product did not elute, only some impurities eluted. However, about 10 minutes into running with 100% EtOAc, the desbromo side product started eluting together with the desired product. Even though the desbromo compound is spread through all the fractions containing the desired product, the percentage of the desbromo compound seem to drastically decrease with time. Therefore, the initial fractions containing the highest percentages of the desbromo were discarded, and the remaining fractions were concentrated to obtain 3.4 g of about 87% purity at 254 nm. (with about 13% desbromo compound). [Base on $^1$H NMR, the desbromo is over-estimated at the 254 nm on the UV, and under estimated on the UV at 220 nm]. The material was recrystallized twice using IPAC and heptanes to obtain 3.16 g (70% yield) of the desired product with purity over 99% on the UV at 254 nm. $^1$H NMR (400 MHz, CHLOROFORM-d) δ ppm 1.31 (d, J=6.32 Hz, 6 H) 3.61-3.70 (m, 4 H) 3.77 (br. s., 4 H) 4.08 (s, 3 H) 5.00 (quin, J=6.19 Hz, 1 H) 6.41 (d, J=7.83 Hz, 1 H) 7.83 (d, J=3.03 Hz, 1 H) 8.37 (d, J=7.83 Hz, 1 H) 8.63-8.71 (m, 2 H). LRMS (ESI) m/e 415 [(M+H)$^+$, calcd for $C_{20}H_{23}FN_6O_3$ 414].

5.6.18. Synthesis of Isopropyl 4-(3-(2-ethoxypyridin-3-yl)pyrazolo[1,5-a]pyrimidin-5-yl)piperazine-1-carboxylate

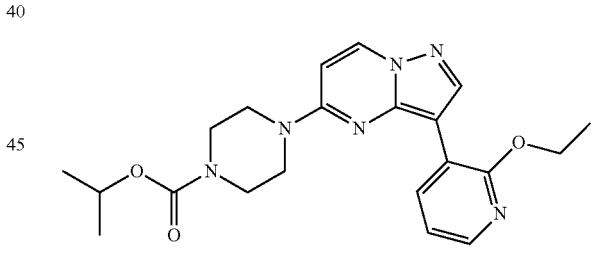

To a 1 liter round bottom flask was added 15.00 g (40.76 mmol) of isopropyl 4-(3-bromopyrazolo[1,5-a]pyrimidin-5-yl)piperazine-1-carboxylate, 8.85 g (52.99 mmol) of (2-ethoxypyridin-3-yl)boronic acid, 14.06 g (101.90 mmol) of K$_2$CO$_3$, 1.41 g (1.22 mmol) of P(PPh$_3$)$_4$, and a stirring rod. After adding all the solids, 200 ml of MeCN was added, followed by the addition of 100 mL of water. The reaction flask was plunged into an oil bath pre-heated to 85° C., and stirred vigorously. This reaction was setup to reflux. After stirring at 85° C. for about 16 hr, it was allowed to cool to RT and diluted with 200 mL of EtOAc. The organic layer was separated, and the aqueous layer was extracted twice with 80 mL portions of EtOAc. The combined organic layers was washed with brine, dried over MgSO$_4$, and concentrated. A small volume of DCM was used to dissolve the crude mixture, and then loaded directly onto a 750 g silica gel column for separation on the ISCO-XL. A gradient of 50% EtOAc/hex to 100% EtOAc was run for the first 35 minutes. The desired product did not elute, only some impurities eluted. However, about 10 minutes into running with 100% EtOAc, the desbromo side product starts eluting together with the desired product. Even though the desbromo compound is spread through all the fractions containing the desired product, the percentage of the desbromo compound seem to decrease with time. Therefore, the initial fractions containing the highest percentages of the desbromo were discarded, and the remaining fractions were concentrated to obtain 13.46 g of about 86% purity at 254 nm. (with about 14% desbromo compound). This material was recrystallized twice, using IPAC and heptanes, to obtain 11.4 g (68%) of the desired product. $^1$H NMR (400 MHz, CHLOROFORM-d) δ ppm 1.30 (d, J=6.32 Hz, 6 H) 1.53 (t, J=7.07 Hz, 3 H) 3.59-3.70 (m, 4 H) 3.70-3.81 (m, 4 H) 4.53 (q, J=7.07 Hz, 2 H) 5.00 (dt, J=12.44, 6.28 Hz, 1 H) 6.38 (d, J=7.83 Hz, 1 H) 6.98 (dd, J=7.45, 4.93 Hz, 1 H) 8.01 (dd, J=4.93, 1.89 Hz, 1 H) 8.37 (d, J=7.83 Hz, 1 H) 8.70 (s, 1 H) 8.76 (dd, J=7.45, 1.89 Hz, 1 H). LRMS (ESI) m/e 411 [(M+H)$^+$, calcd for $C_{21}H_{26}N_6O_3$ 410].

5.6.19. Synthesis of 2-Methoxyethyl 4-(3-(2-methoxypyridin-3-yl)pyrazolo[1,5-a]pyrimidin-5-yl)piperazine-1-carboxylate

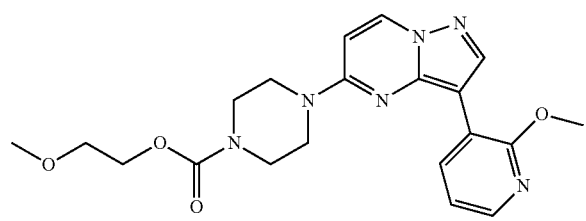

Part A. 2-methoxyethyl 4-(3-bromopyrazolo[1,5-a]pyrimidin-5-yl)piperazine-1-carboxylate

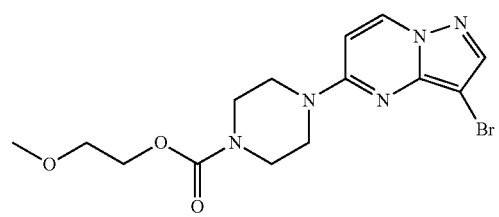 [SMILES: COCCOC(=O)N1CCN(c2ccn3ncc(Br)c3n2)CC1]

To 10.00 g (35.44 mmol) of 3-bromo-5-(piperazin-1-yl)pyrazolo[1,5-a]pyrimidine dissolved in 120 mL of EtOAc, at 0° C. was added 5.40 g (38.99 mmol) of 2-methoxyethyl carbonochloridate, followed by 9.86 mL (70.88 mmol) of TEA. After 5 minutes, the ice bath was removed, and the reaction mixture stirred at RT. After 5 hr, LCMS showed that the reaction was complete. It was diluted with EtOAc, quenched with brine, and the organic layer dried over MgSO$_4$. It was concentrated and purified on the ISCO with a 330 g column eluting with 0-9% MeOH/DCM to obtain the desired product, 12.63 g (93%). $^1$H NMR (400 MHz, CHLOROFORM-d) δ ppm 3.42 (s, 3 H) 3.62-3.69 (m, 6 H) 3.73-3.82 (m, 4 H) 4.26-4.35 (m, 2 H) 6.36 (d, J=7.83 Hz, 1 H) 7.86 (s, 1 H) 8.27 (d, J=7.83 Hz, 1 H). LRMS (ESI) m/e 384 [(M+H)$^+$, (doublet), calcd for $C_{14}H_{15}BrN_5O_3$ 383].

Part B. 2-methoxyethyl 4-(3-(2-methoxypyridin-3-yl)pyrazolo[1,5-a]pyrimidin-5-yl)piperazine-1-carboxylate

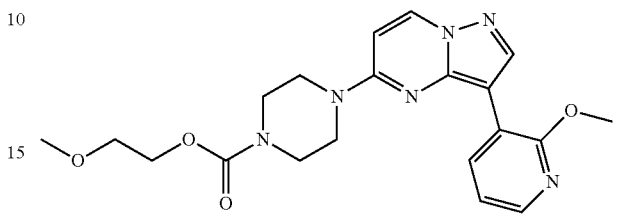

To a 100 mL round bottom flask was added 15.00 g (39.06 mmol) of 2-methoxyethyl 4-(3-bromopyrazolo[1,5-a]pyrimidin-5-yl)piperazine-1-carboxylate, 7.17 g (46.88 mmol) of (2-methoxypyridin-3-yl)boronic acid, 38 mL (273.44 mmol) of TEA, 200 ml of MeCN was added, 100 mL of water, followed by the addition of 0.21 g (0.29 mmol) of Pd-132. The reaction flask was plunged into an oil bath pre-heated to 85° C., and stirred. After 1 hr, the reaction was complete, and it was allowed to cool to RT, and then diluted with 200 mL of EtOAc. The organic layer was separated, and the aqueous layer was extracted twice with 150 mL portions of EtOAc. The combined organic layers was washed with brine, dried over MgSO$_4$, and filtered through a thin pad of silica gel, and the filtrate was concentrated to obtain 14 g solid product, [90% desired product and 10% desbromo side product, based on uv absorption at 254 nm].

The resulting solid was subjected to charcoal treatment, by dissolving all 14 g in 100 mL DCE and adding 500 mg of Darco. It was heated and stirred for about 1.5 hr, cooled and then filtered through celite, and concentrated. The product obtained appeared to be clean enough to be recrystallized without subjecting it to silica gel chromatography. The recrystallization was carried out by dissolving it in a small volume of IPAC at about 75° C. (a few milliliters MeOH was used to aid the dissolution of the solids). After complete dissolution, heptane was added and precipitates begun forming, and allowed to cool at 0° C. for 1 hr. It was then filtered and dried 13.1 g product with purity of about 97%. This material was recrystallized again, to obtain a pale yellow solid 12.45 g (77% yield, purity to over 99%) of the desired product. $^1$H NMR (400 MHz, CHLOROFORM-d) δ ppm 3.42 (s, 3 H) 3.61-3.71 (m, 6 H) 3.72-3.80 (m, 4 H) 4.10 (s, 3 H) 4.29-4.34 (m, 2 H) 6.38 (d, J=7.83 Hz, 1 H) 7.00 (dd, J=7.45, 4.93 Hz, 1 H) 8.04 (dd, J=4.93, 1.89 Hz, 1 H) 8.37 (d, J=7.83 Hz, 1 H) 8.64 (s, 1 H) 8.74 (dd, J=7.45, 1.89 Hz, 1 H). $^{13}$C NMR (101 MHz, CHLOROFORM-d) δ ppm 43.49, 44.87, 53.51, 59.15, 64.96, 71.07, 76.92, 77.24, 77.56, 96.37, 100.99, 116.93, 117.05, 135.42, 136.16, 142.79, 145.37, 146.26, 155.46, 155.52, 160.08. LRMS (ESI) m/e 413 [(M+H)+, calcd for C20H24N6O4 412].

5.6.20. Synthesis of tert-butyl 4-(3-(2-methoxypyridin-3-yl)pyrazolo[1,5-a]pyrimidin-5-yl)piperazine-1-carboxylate

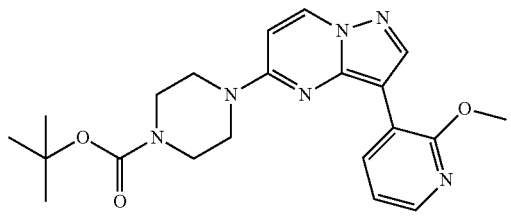 [SMILES: COc1ncccc1-c1cnn2ccc(N3CCN(C(=O)OC(C)(C)C)CC3)nc12]

Part A. tert-butyl 4-(3-bromopyrazolo[1,5-a]pyrimidin-5-yl)piperazine-1-carboxylate

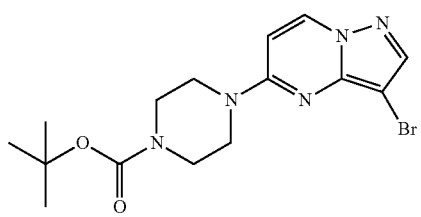 [SMILES: CC(C)(C)OC(=O)N1CCN(c2ccn3ncc(Br)c3n2)CC1]

3-bromo-5-chloropyrazolo[1,5-a]pyrimidine (10 g, 43 mmol) taken up in isopropanol. T-butylpiperazine carboxylate (9.61 g, 51.6 mmol), diisopropylethylamine (22.4 mL, 129 mmol) added and stirred at 65° C. overnight. Reaction was cooled to room temperature, diluted with water and solid product filtered off. The solid was washed with water, dried to obtain 15.84 g crude product for further reaction, as is. LRMS (ESI) m/z 382/384 [(M+H)+], calc'd for C15H20BrN5O2: 382.2.

Part B. tert-butyl 4-(3-(2-methoxypyridin-3-yl)pyrazolo[1,5-a]pyrimidin-5-yl)piperazine-1-carboxylate

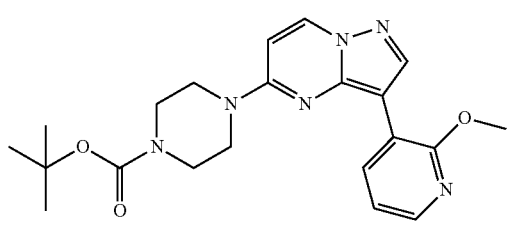 [SMILES: COc1ncccc1-c1cnn2ccc(N3CCN(C(=O)OC(C)(C)C)CC3)nc12]

Tert-butyl 4-(3-bromopyrazolo[1,5-a]pyrimidin-5-yl)piperazine-1-carboxylate (15.84 g, 41.5 mmol), 2-methoxypyridine-3-boronic acid (12.68 g, 82.9 mmol), potassium carbonate (17.16 g, 124.5 mmol), Pd(OAc)2 (92 mg, 4.15 mmol), and x-Phos (394 mg, 8.3 mmol) were taken up in 60 mL dioxane and 30 mL water under nitrogen and stirred at 75° C. for 2 hours. Reaction then cooled to room temperature, diluted with toluene washed with brine. The organic layer filtered through magnesium sulfate and celite plug. Reduced in vacuo and run through an ISCO silica column with hexane:ethyl acetate 0-100%. The product plus some desbromo co elute, Concentrated in vacuo. Product recrystallized 2 times from IPAC:Heptane 30:70, washed with heptanes dried to get 12 g product. 1H NMR (400 MHz, DMSO-d6) δ 8.78-8.85 (m, 1H), 8.74 (d, J=8.08 Hz, 1H), 8.50 (s, 1H), 7.92-8.02 (m, 1H), 7.04-7.13 (m, 1H), 6.80 (d, J=8.08 Hz, 1H), 4.00 (s, 3H), 3.70-3.78 (m, 4H), 3.49 (d, J=5.31 Hz, 4H), 1.44 (s, 9H). LRMS (ESI) m/z 411 [(M+H)+], calc'd for C21H26N6O3: 410.48.

5.6.21. Synthesis of Isopropyl 4-(3-(5-fluoro-2-methoxyphenyl)pyrazolo[1,5-a]pyrimidin-5-yl)piperazine-1-carboxylate

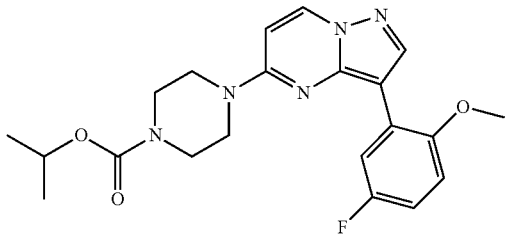 [SMILES: COc1ccc(F)cc1-c1cnn2ccc(N3CCN(C(=O)OC(C)C)CC3)nc12]

Part A. isopropyl 4-(3-bromopyrazolo[1,5-a]pyrimidin-5-yl)piperazine-1-carboxylate

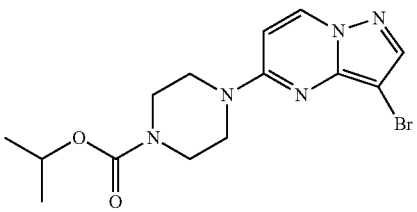 [SMILES: CC(C)OC(=O)N1CCN(c2ccn3ncc(Br)c3n2)CC1]

3-bromo-5-(piperazin-1-yl)pyrazolo[1,5-a]pyrimidine (2.5 g, 8.87 mmol) taken up in DCM. Isopropylchloroformate 1M in toluene (13.3 mL, 13.3 mmol), and triethylamine (2.47 mL, 17.7 mmol) added and stirred at room temperature 30 minutes. Reaction washed with water, DCM layer dried over magnesium sulfate filtered reduced in vacuo. Run on an Isco silica column with DCM:MeOH 0-5%. Product fractions were combined and reduced in vacuo to obtain 2.86 g crude product for further reaction as is. LRMS (ESI) m/z 368/370 [(M+H)+], calc'd for C14H18BrN5O: 368.24.

Part B. isopropyl 4-(3-(5-fluoro-2-methoxyphenyl)pyrazolo[1,5-a]pyrimidin-5-yl)piperazine-1-carboxylate

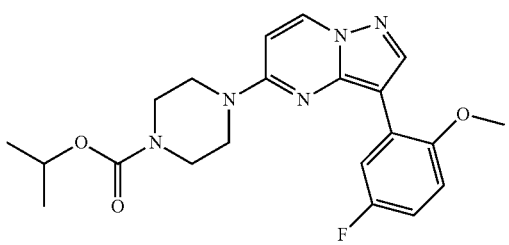 [SMILES: COc1ccc(F)cc1-c1cnn2ccc(N3CCN(C(=O)OC(C)C)CC3)nc12]

Isopropyl 4-(3-bromopyrazolo[1,5-a]pyrimidin-5-yl)piperazine-1-carboxylate (2.86 g, 7.8 mmol), 5-fluoro-2-methoxyphenyl boronic acid (2.64 g, 15.5 mmol), potassium carbonate (3.22 g, 23.3 mmol), Pd(OAc)$_2$ (35 mg, 0.155 mmol), and x-Phos (146 mg, 0.31 mmol) were taken up in 15 mL dioxane and 7 mL water under nitrogen and stirred at 80° C. for 2 hours. Reaction then cooled to room temperature, filtered through celited plug with ethyl acetate. Reduced in vacuo and run through an isco silica column with hexane: ethyl acetate 75-100%. Product plus desbromo co-elute, reduced in Vacuo. Product recrystallized 2 times from ethyl acetate:Hexane, washed with heptanes dried to get 12 g product. $^1$H NMR (400 MHz, DMSO-d6) δ 8.73 (d, J=7.78 Hz, 1H), 8.50 (s, 1H), 8.29 (dd, J=3.14, 11.17 Hz, 1H), 7.04 (dd, J=5.02, 9.03 Hz, 1H), 6.95 (dd, J=3.26, 7.78 Hz, 1H), 6.79 (d, J=8.03 Hz, 1H), 4.77-4.85 (m, 1H), 3.87 (s, 3H), 3.70-3.78 (m, 4H), 3.48-3.56 (m, 4H), 1.21 (d, J=6.27 Hz, 6H). LRMS (ESI) m/z 414 [(M+H)$^+$, calc'd for C$_{21}$H$_{24}$N$_5$O$_3$: 413.4.

5.6.22. Synthesis of Isopropyl 4-(3-(2-methoxy-6-methylpyridin-3-yl)pyrazolo[1,5-a]pyrimidin-5-yl)piperazine-1-carboxylate

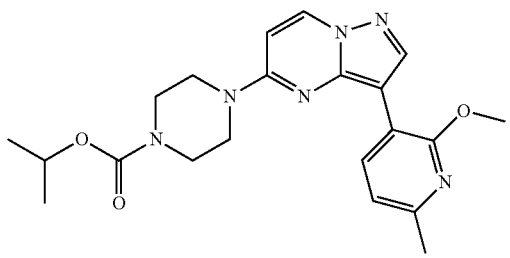 [SMILES: COc1nc(C)ccc1-c1cnn2ccc(N3CCN(C(=O)OC(C)C)CC3)nc12]

To a 100 mL liter round bottom flask was added 2.00 g (5.43 mmol) of isopropyl 4-(3-bromopyrazolo[1,5-a]pyrimidin-5-yl)piperazine-1-carboxylate, 1.00 g (5.98 mmol) of (2-methoxy-6-methylpyridin-3-yl)boronic acid, 0.19 g (0.16 mmol) of Pd(PPh$_3$)$_4$, and a stirring rod.

After adding all the solids, 30 ml of 2% TPGS-750-M solution was added, followed by the addition of 3.80 mL (27.15 mmol) triethylamine. The reaction flask was plunged into an oil bath pre-heated to 85° C., and stirred vigorously. It took about 0.25 hr of stirring for all the suspended solids to dissolve completely. After stirring at 85° C. for about 2 hr, LCMS showed that the reaction was complete. It was allowed to cool to RT, dilute with 40 mL EtOAc. The organic layer was separated, and the aqueous layer was extracted twice with 30 mL portions EtOAc. The combined organic layers was washed with brine, dried over MgSO$_4$, and concentrated. A small volume of DCM was used to dissolve the crude mixture, and then loaded directly onto a 80 g silica gel column for separation on the ISCO. A gradient of 50% EtOAc/hex to 100% EtOAc was run for the first 15 minutes, and then the column was run with only EtOAc. The desired product begun eluting about 8 minutes into running with only EtOAc. The desbromo side product elutes together with the desired product. Even though the desbromo compound is spread through all the fractions containing the desired product, the percentage of the desbromo compound seem to decrease with time. Therefore, the first few tubes containing the highest percentages of the desbromo were discarded, and the remaining fractions were concentrated to obtain 1.73 g of about 84% purity at 254 nm (with about 16% desbromo compound).

[Base on $^1$H nmr, the desbromo is over-estimated at the 254 nm on the UV, and under estimated on the UV at 220 nm].

The material was recrystallized twice using IPAC and heptanes, to afford 1.45 g (65% yield) of the desired product. $^1$H NMR (400 MHz, CHLOROFORM-d) δ ppm 1.30 (d, J=6.32 Hz, 6 H) 2.49 (s, 3 H) 3.59-3.68 (m, 4 H) 3.73 (dd, J=6.19, 3.66 Hz, 4 H) 4.07 (s, 3 H) 4.99 (dt, J=12.44, 6.28 Hz, 1 H) 6.36 (d, J=7.83 Hz, 1 H) 6.85 (d, J=7.58 Hz, 1 H) 8.35 (d, J=7.83 Hz, 1 H) 8.55-8.63 (m, 2 H); $^{13}$C NMR (101 MHz, CHLOROFORM-d) δ ppm 22.48, 24.10, 43.39, 44.94, 53.38, 69.37, 96.32, 101.34, 113.40, 116.03, 135.94, 136.12, 145.14, 146.15, 152.13, 155.35, 155.45, 159.49. LRMS (ESI) m/e 411 [(M+H)$^+$, calcd for C$_{21}$H$_{26}$N$_6$O$_3$ 410].

5.6.23. Synthesis of Isopropyl 4-(3-(6-methoxypyridin-2-yl)pyrazolo[1,5-a]pyrimidin-5-yl)piperazine-1-carboxylate

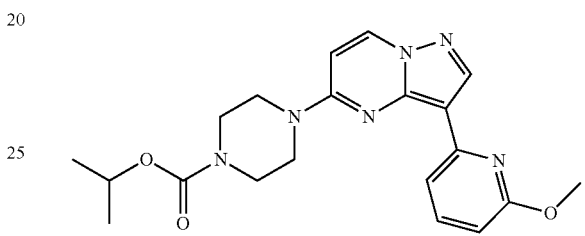

Part A. isopropyl 4-(3-(4,4,5,5-tetramethyl-1,3,2-dioxaborolan-2-yl)pyrazolo[1,5-a]pyrimidin-5-yl)piperazine-1-carboxylate

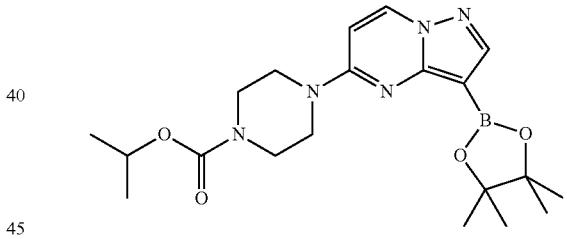

To 184 mg (0.50 mmol) of isopropyl 4-(3-bromopyrazolo[1,5-a]pyrimidin-5-yl)piperazine-1-carboxylate in a 50 mL round bottom flask was added 191 mg (0.75 mmol) of 4,4,4',4',5,5,5',5'-octamethyl-2,2'-bi(1,3,2-dioxaborolane), 147 mg (1.50 mmol) of KOAc, 8 mL of DMSO followed by 41 mg (0.05 mmol) of PdCl$_2$(dppf)$_2$.DCM. The air was replaced with N$_2$, and the mixture heated to 80° C. with stirring. Next morning LCMS shows reaction had gone to completion. It was cooled to RT, diluted with EtOAc, washed with brine, and the organic layer dried over MgSO$_4$. It was concentrated and purified in the ISCO using a 12 g column, and eluting with 25-100% EtOAc/hex to obtain 107 mg of the desired product [Purity was only about 85%, about 15% was hydrolyzed to the corresponding boronic acid].

Part B. Isopropyl 4-(3-(6-methoxypyridin-2-yl)pyrazolo[1,5-a]pyrimidin-5-yl)piperazine-1-carboxylate To 65 mg (0.157 mmol) of isopropyl 4-(3-(4,4,5,5-tetramethyl-1,3,2-dioxaborolan-2-yl)pyrazolo[1,5-a]pyrimidin-5-yl)piperazine-1-carboxylate in a microwave vial was added, 29 mg (0.157 mmol) of 2-bromo-6-methoxypyridine, 43 mg (0.313 mmol) of K$_2$CO$_3$, 18 mg (0.016 mmol) Pd(PPh$_3$)$_4$, 3 mL of DME and then 1 mL water. The resulting mixture was microwaved at 125° C. for 0.33 hr. It was diluted with EtOAc, washed with brine, and the organic layer dried over MgSO$_4$. It was concentrated and purified on the neutral PREP HPLC to obtain 42 mg of the desired product. $^1$H NMR (400 MHz, CHLOROFORM-d) δ ppm 1.30 (d, J=6.32 Hz, 6 H) 3.60-3.74 (m, 4 H) 3.81 (br. s., 4 H) 4.04 (s, 3 H) 5.00 (quin, J=6.25 Hz, 1 H) 6.39 (d, J=7.83 Hz, 1 H) 6.55 (dd, J=8.08, 0.76 Hz, 1 H) 7.62 (dd, J=8.08, 7.58 Hz, 1 H) 7.83-7.93 (m, 1 H) 8.37 (d, J=7.83 Hz, 1 H) 8.66 (s, 1 H). LRMS (ESI) m/e 397 [(M+H)$^+$, calcd for C$_{20}$H$_{24}$N$_6$O$_3$ 396 ].

5.6.24. Synthesis of 5-isopropyl-3-(4-(3-(2-methoxypyridin-3-yl)pyrazolo[1,5-a]pyrimidin-5-yl)piperazin-1-yl)-1,2,4-oxadiazole

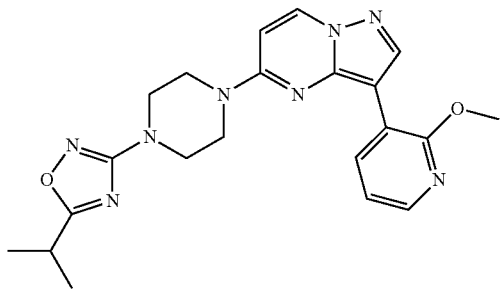 [SMILES: COc1ncccc1-c1cnn2ccc(N3CCN(c4noc(C(C)C)n4)CC3)nc12]

Part A. 4-(3-bromopyrazolo[1,5-a]pyrimidin-5-yl)piperazine-1-carbonitrile

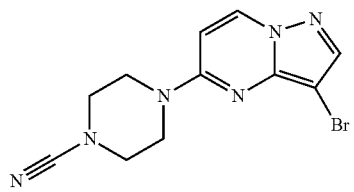 [SMILES: N#CN1CCN(c2ccn3ncc(Br)c3n2)CC1]

3-bromo-5-(piperazin-1-yl)pyrazolo[1,5-a]pyrimidine (500 mg, 1.77 mmol) taken up in 20 mL DCM and stirred at 0° C. in an ice bath. Sodium bicarbonate (744 mg, 8.86 mmol) in 6 mL water added and stirred. Cyanogen bromide (225 mg, 2.12 mmol) added and stirred at 0° C. for 30 minutes then allowed to reach room temperature and stirred overnight. Reaction diluted with DCM washed with water, DCM layer dried over magnesium sulfate reduced in vacuo for 500 mg crude product for further reaction as is. LRMS (ESI) m/z 307/309 [(M+H)]+, calc'd for C11H11BrN6: 307.15.

Part B. 3-(4-(3-bromopyrazolo[1,5-a]pyrimidin-5-yl)piperazin-1-yl)-5-isopropyl-1,2,4-oxadiazole

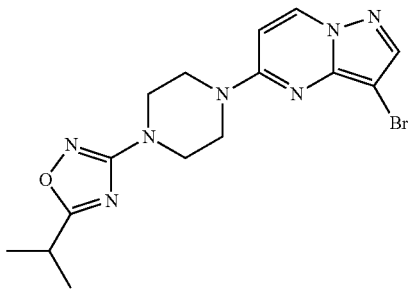 [SMILES: CC(C)c1nc(N2CCN(c3ccn4ncc(Br)c4n3)CC2)no1]

4-(3-bromopyrazolo[1,5-a]pyrimidin-5-yl)piperazine-1-carbonitrile (450 mg, 1.46 mmol) in 9 mL DMF and sodium carbonate (155 mg, 1.46 mmol) stirred room temperature 15 minutes, hydroxylamine HCl (203 mg, 2.9 mmol) added and reaction stirred 30 minutes at 80° C. Then 12 mL toluene added and pyridine (474 uL, 5.86 mmol) and isobutyricanhydride (973 uL, 5.86 mmol) added and reaction stirred at 80° C. for 1.5 hours. Reaction cooled to room temperature reduced in vacuo then taken up in ethyl acetate and washed with water, brine, water. Organic layer dried over magnesium sulfate and reduced in vacuo. For 250 mg crude product to use as is in further reactions. LRMS (ESI) m/z 392/394 [(M+H)]+, calc'd for C$_{15}$H$_{18}$BrN$_7$O: 392.26.

Part C. 5-isopropyl-3-(4-(3-(2-methoxypyridin-3-yl)pyrazolo[1,5-a]pyrimidin-5-yl)piperazin-1-yl)-1,2,4-oxadiazole 3-(4-(3-bromopyrazolo[1,5-a]pyrimidin-5-yl)piperazin-1-yl)-5-isopropyl-1,2,4-oxadiazole (200 mg, 0.51 mmol), 2-methoxypyridine-3-boronic acid (156 mg, 1.0 mmol), potassium carbonate (211 mg, 1.53 mmol), Pd(OAc)$_2$ (3 mg, 0.01 mmol), and x-Phos (10 mg, 0.02 mmol) were taken up in 2 mL dioxane and 1 mL water in a sealed tube and heated at 85° C. for 2 hours. Reaction then cooled to room temperature filtered through a celite plug with acetonitrile and DCM, reduced in vacuo. Purified on Shimadzu neutral phase prep lyophilized to get 12 mg product. $^1$H NMR (400 MHz, DMSO-d6) δ 8.83 (dd, J=1.77, 7.58 Hz, 1H), 8.77 (d, J=7.83 Hz, 1H), 8.51 (s, 1H), 7.99 (dd, J=1.89, 4.93 Hz, 1H), 7.10 (dd, J=4.80, 7.58 Hz, 1H), 6.86 (d, J=8.08 Hz, 1H), 4.00 (s, 3H), 3.84-3.90 (m, 4H), 3.48-3.53 (m, 4H), 3.15 (t, J=7.07 Hz, 1H), 1.29 (d, J=6.82 Hz, 6H). LRMS (ESI) m/z 421 [(M+H)]$^+$, calc'd for C$_{21}$H$_{24}$N$_8$O$_2$: 420.48.

5.6.25. Synthesis of (S)-2-amino-1-(4-(3-(2-methoxypyridin-3-yl)pyrazolo[1,5-a]pyrimidin-5-yl)piperazin-1-yl)-4-methylpentan-1-one

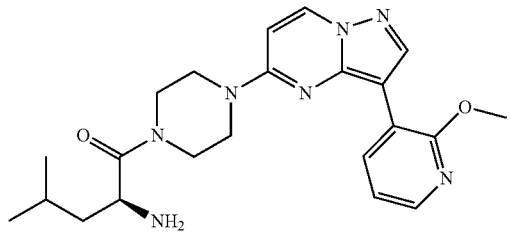 [SMILES: COc1ncccc1-c1cnn2ccc(N3CCN(C(=O)[C@@H](N)CC(C)C)CC3)nc12]

Part A. (S)-2-amino-1-(4-(3-bromopyrazolo[1,5-a]pyrimidin-5-yl)piperazin-1-yl)-4-methylpentan-1-one

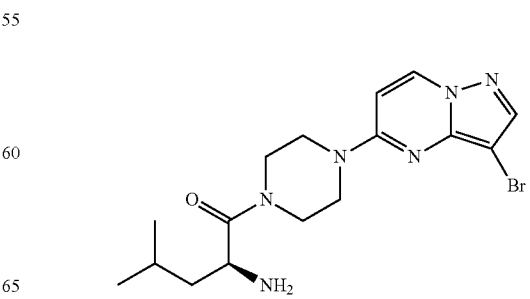

3-bromo-5-(piperazin-1-yl)pyrazolo[1,5-a]pyrimidine (200 mg, 0.71 mmol), Boc-L-Leu (196 mg, 0.85 mmol), HATU (245 mg, 1.06 mmol), and triethylamine (394 uL, 2.83 mmol) taken up in DMF and stirred at room temperature overnight. Reaction was diluted with DCM and washed with water. The organic layer was dried over magnesium sulfate, filtered and reduced in vacuo. The residue was taken up in 20 mL of a 40% TFA in DCM solution and stirred at 35° C. overnight. The mixture was concentrated in vacuo and passed through a silica plug with 10% MeOH in DCM. Solvent was removed and the residue was dried to give 600 mg crude product as TFA salt for further reactions. LRMS (ESI) m/z 395/397 [(M+H)]+, calc'd for $C_{16}H_{23}BrN_6O$: 395.31.

Part B. (S)-2-amino-1-(4-(3-(2-methoxypyridin-3-yl)pyrazolo[1,5-a]pyrimidin-5-yl)piperazin-1-yl)-4-methylpentan-1-one (S)-2-amino-1-(4-(3-bromopyrazolo[1,5-a]pyrimidin-5-yl)piperazin-1-yl)-4-methylpentan-1-one (300 mg, 0.59 mmol), 2-methoxypyridine-3-boronic acid (135 mg, 0.88 mmol), potassium carbonate (326 mg, 2.36 mmol), Pd(OAc)$_2$ (3 mg, 0.011 mmol), and x-Phos (11 mg, 0.022 mmol) were taken up in 2 mL dioxane and 1 mL water in a sealed tube and heated at 85° C. for 2 hours. Reaction then cooled to room temperature filtered through a celite plug with acetonitrile and DCM, reduced in vacuo. Purified on shimadzu neutral phase prep, lyophilized to get 28.1 mg of formic acid salt product. $^1$H NMR (400 MHz, DMSO-d6) δ 8.82 (dd, J=2.02, 7.58 Hz, 1H), 8.77 (d, J=7.83 Hz, 1H), 8.51 (s, 1H), 8.27 (s, 1H), 7.99 (dd, J=1.77, 4.80 Hz, 1H), 7.09 (dd, J=4.80, 7.58 Hz, 1H), 6.83 (d, J=8.08 Hz, 1H), 4.00 (s, 3H), 3.62-3.93 (m, 9H), 1.72-1.88 (m, 1H), 1.23-1.42 (m, 2H), 0.91 (dd, J=6.57, 10.11 Hz, 6H). LRMS (ESI) m/z 424 [(M+H)]$^+$, calc'd for $C_{22}H_{29}N_7O_2$: 423.52.

5.6.26. Synthesis of (S)-2-amino-N—((S)-1-(3-(2-methoxypyridin-3-yl)pyrazolo[1,5-a]pyrimidin-5-yl)pyrrolidin-3-yl)-N,4-dimethylpentanamide

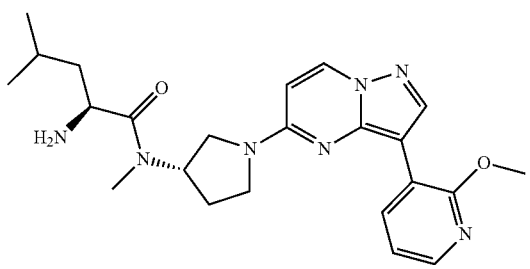 [SMILES: COc1ncccc1-c1cnn2ccc(N3CC[C@H](N(C)C(=O)[C@@H](N)CC(C)C)C3)nc12]

Part A. (S)-tert-butyl (1-(3-bromopyrazolo[1,5-a]pyrimidin-5-yl)pyrrolidin-3-yl)carbamate

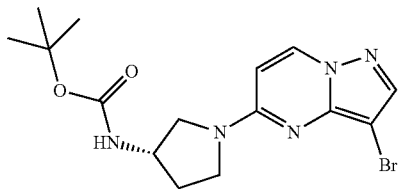 [SMILES: CC(C)(C)OC(=O)N[C@H]1CCN(c2ccn3ncc(Br)c3n2)C1]

3-bromo-5-chloropyrazolo[1,5-a]pyrimidine (2.2 g, 9.5 mmol) (S)-3-Boc-aminopyrrolidine (2.6 g, 14.2 mmol), and triethylamine (5.27 mL, 37.9 mmol) were taken up in isopropanol in a sealed tube and microwaved at 140° C. for 30 minutes. Reaction stripped down in vacuo taken up in ethyl acetate washed with water then passed through a silica plug with ethyl acetate. Solvent was removed in vacuo to give 3.6 g crude product that was carried on as is to part B. LRMS (ESI) m/z 382/384 [(M+H)]+, calc'd for C15H19BrN5O2: 382.2.

Part B. (S)-1-(3-bromopyrazolo[1,5-a]pyrimidin-5-yl)-N-methylpyrrolidin-3-amine

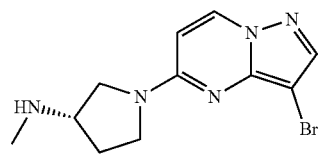 [SMILES: CN[C@H]1CCN(c2ccn3ncc(Br)c3n2)C1]

(S)-tert-butyl (1-(3-bromopyrazolo[1,5-a]pyrimidin-5-yl)pyrrolidin-3-yl)carbamate (3.6 g, 9.4 mmol) taken up in 15 mL DMF and cooled to 0° C. in an ice bath. Iodomethane (1.026 mL, 16.5 mmol) added and stirred 5 minutes. Then sodium hydride 60% in oil (754 mg, 18.8 mmol) was slowly added. Reaction stirred 5 minutes at 0° C. then removed from ice bath and stirred 30 minutes at room temperature. Reaction was quenched with ice then extracted with ethyl acetate 2×. Ethyl acetate fractions combined dried over magnesium sulfate filtered reduce in vacuo. This was then taken up in 26 mL DCM and 4 mL TFA added. Stirred 1 hour until complete by LC/MS. Reaction washed with 1N NaOH, DCM layer removed dried over magnesium sulfate filtered, reduced in vacuo to get 2.72 g crude product carried on as is to part C. LRMS (ESI) m/z 296/298 [(M+H)]$^+$, calc'd for C11H14BrN5: 296.17.

Part C. (S)-2-amino-N—((S)-1-(3-bromopyrazolo[1,5-a]pyrimidin-5-yl)pyrrolidin-3-yl)-N,4-dimethylpentanamide

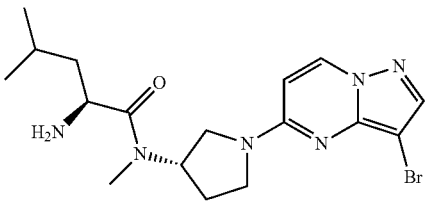 [SMILES: CC(C)C[C@H](N)C(=O)N(C)[C@H]1CCN(c2ccn3ncc(Br)c3n2)C1]

(S)-1-(3-bromopyrazolo[1,5-a]pyrimidin-5-yl)-N-methylpyrrolidin-3-amine (200 mg, 0.68 mmol) Boc-L-Leu (187 mg, 0.81 mmol), HATU (385 mg, 1.01 mmol), and triethylamine (375 uL, 2.7 mmol) Taken up in DMF and Stirred at room temp overnight. Reaction diluted with DCM, washed with water, DCM layer then dried over magnesium sulfate filtered and reduced in vacuo. This was then taken up in 26 mL DCM and 4 mL TFA added. Stirred 1 hour until complete by LC/MS. Reaction washed with 1N NaOH, DCM layer removed dried over magnesium sulfate filtered, reduced in vacuo for 226 mg crude product used as is in part D. LRMS (ESI) m/z 409/411 [(M+H)]+, calc'd for $C_{17}H_{24}BrN_6O$: 409.

Part D. (S)-2-amino-N—((S)-1-(3-(2-methoxypyridin-3-yl)pyrazolo[1,5-a]pyrimidin-5-yl)pyrrolidin-3-yl)-N,4-dimethylpentanamide (S)-2-amino-N—((S)-1-(3-bromopyrazolo[1,5-a]pyrimidin-5-yl)pyrrolidin-3-yl)-N,4-dimethylpentanamide (220 mg, 0.54 mmol), 2-methoxypyridine-3-boronic acid (164 mg, 1.1 mmol), potassium carbonate (291 mg, 2.15 mmol), Pd(OAc)$_2$ (2 mg, 0.011 mmol) and x-phos (10 mg, 0.022 mmol) were taken up in 2 mL acetonitrile and 1 mL water and heated in a sealed tube at 85° C. for 2 hours. Reaction was then filtered through celite with acetonitrile and DCM reduced in vacuo, then purified on Shimadzu neutral phase prep and product fractions lyophilized to get (S)-2-amino-N—((S)-1-(3-(2-methoxypyridin-3-yl)pyrazolo[1,5-a]pyrimidin-5-yl)pyrrolidin-3-yl)-N,4-dimethylpentanamide 41.3 mg as 0.5 eq formic salt. $^1$H NMR (400 MHz, DMSO-d6) δ 8.87-8.97 (m, 1H), 8.72 (s, 1H), 8.50 (s, 1H), 8.30 (s, 1H), 7.96 (dd, J=2.02, 4.80 Hz, 1H), 7.00-7.11 (m, 1H), 6.51 (d, J=7.83 Hz, 1H), 4.00 (s, 3H), 3.48-3.64 (m, 1H), 3.43 (br. s., 3H), 2.96 (s, 2H), 2.81 (s, 1H), 2.11-2.28 (m, 2H), 1.72-1.89 (m, 1H), 1.19-1.39 (m, 2H), 0.90 (dd, J=1.89, 6.69 Hz, 6H). (ESI) m/z 438 [(M+H)]$^+$, calc'd for $C_{23}H_{31}N_7O_2$: 437.5.

5.6.27. Synthesis of (S)-2-amino-1-(4-(3-(2-methoxypyridin-3-yl)pyrazolo[1,5-a]pyrimidin-5-yl)piperazin-1-yl)-3-methylbutan-1-one

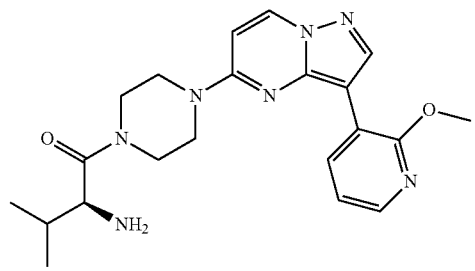 [SMILES: COc1ncccc1-c1cnn2ccc(N3CCN(C(=O)[C@@H](N)C(C)C)CC3)nc12]

Part A. (S)-2-amino-1-(4-(3-bromopyrazolo[1,5-a]pyrimidin-5-yl)piperazin-1-yl)-3-methylbutan-1-one

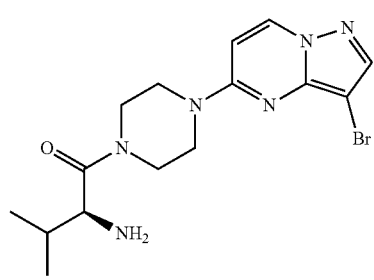 [SMILES: CC(C)[C@H](N)C(=O)N1CCN(c2ccn3ncc(Br)c3n2)CC1]

3-bromo-5-(piperazin-1-yl)pyrazolo[1,5-a]pyrimidine (400 mg, 1.42 mmol) Boc-L-Leucine (392 mg, 1.7 mmol), HATU (490 mg, 2.13 mmol), and triethylamine (788 uL, 5.7 mmol) taken up in DMF and stirred at room temperature overnight. Reaction diluted with DCM washed with water, DCM layer then dried over magnesium sulfate filtered and reduced in Vacuo. This was then taken up in 26 mL DCM and 4 mL TFA added. Stirred 1 hour until complete by LC/MS. Reaction was washed with 1N NaOH, DCM layer removed dried over magnesium sulfate filtered, reduced in vacuo to obtain 349 mg crude product for further reaction as is. LRMS (ESI) m/z 381/383 [(M+H)]+, calc'd for $C_{15}H_{21}BrN_6O$: 381.28.

Part B. (S)-2-amino-1-(4-(3-(2-methoxypyridin-3-yl)pyrazolo[1,5-a]pyrimidin-5-yl)piperazin-1-yl-3-methylbutan-1-one (S)-2-amino-1-(4-(3-bromopyrazolo[1,5-a]pyrimidin-5-yl)piperazin-1-yl)-3-methylbutan-1-one (110 m g, 0.29 mmol), (2-methoxypyridin-3-yl)boronic acid (88 mg, 0.58 mmol), potassium carbonate (120 mg, 0.87 mmol), Pd(OAc)$_2$ (1 mg, 0.0058 mmol), and x-Phos (5 mg, 0.012 mmol) were taken up in 3 mL dioxane and 1 mL water under nitrogen and stirred at 85° C. for 2 hours. Reaction then cooled to room temperature filtered through celited plug with acetonitrile and DCM. Reduced in vacuo and purified on shimadzu neutral phase prep, lypholized to get 18 mg 1.5 eq formic salt product. $^1$H NMR (400 MHz, MSO-d6) δ 8.83 (dd, J=1.77, 7.58 Hz, 1H), 8.78 (d, J=7.83 Hz, 1H), 8.52 (s, 1H), 8.35 (s, 2H), 7.99 (dd, J=1.89, 4.93 Hz, 1H), 7.09 (dd, J=4.93, 7.45 Hz, 1H), 6.85 (d, J=7.83 Hz, 1H), 4.01 (s, 3H), 3.81-3.89 (m, 1H), 3.74 (d, J=5.31 Hz, 3H), 3.68 (d, J=7.58 Hz, 3H), 1.76-1.89 (m, 1H), 0.94 (d, J=6.82 Hz, 3H), 0.86 (d, J=6.82 Hz, 3H). LRMS (ESI) m/z 410 [(M+H)]$^+$, calc'd for $C_{21}H_{27}N_7O_2$: 409.5.

5.6.28. Synthesis of (S)-2-amino-3-methoxy-1-(4-(3-(2-methoxypyridin-3-yl)pyrazolo[1,5-a]pyrimidin-5-yl)piperazin-1-yl)propan-1-one

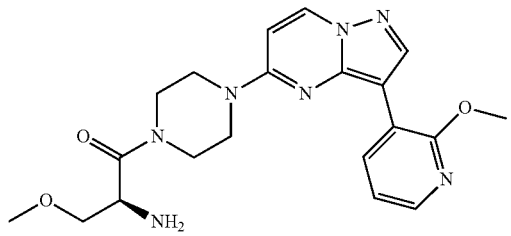

Part A. (S)-2-amino-1-(4-(3-bromoyyrazolo[1,5-a]pyrimidin-5-yl)piperazin-1-yl)-3-methoxypropan-1-one

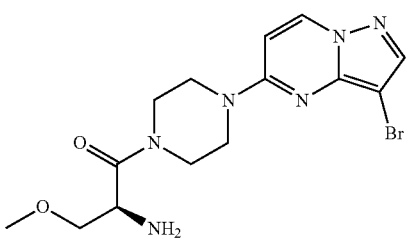 [SMILES: COC[C@H](N)C(=O)N1CCN(c2ccn3ncc(Br)c3n2)CC1]

3-Bromo-5-(piperazin-1-yl)pyrazolo[1,5-a]pyrimidine (300 mg, 1.1 mmol) taken up in 10 mL DMF. Boc-Ser(Me)-OH (280 mg, 1.3 mmol), HATU (368 mg, 1.6 mmol), and triethylamine (590 uL, 4.25 mmol) was added and stirred at room temp overnight. Reaction was diluted with DCM and washed with water. DCM layer was dried over magnesium sulfate reduced in vacuo. This was then taken up in 30% TFA in DCM solution and stirred at room temperature for 2 hours. It was then cooled to 0° C. and conc Aq NaOH added slowly until aqueous layer remains basic. DCM layer extracted dried over magnesium sulfate, reduced in vacuo for 405 mg crude product for further reaction as is. LRMS (ESI) m/z 383/385 [(M+H)]+, calc'd for C14H19BrN6O2: 383.25.

Part B. (S)-2-amino-3-methoxy-1-(4-(3-(2-methoxypyridin-3-yl)pyrazolo[1,5-a]pyrimidin-5-yl)piperazin-1-yl)propan-1-one 3(S)-2-amino-1-(4-(3-bromopyrazolo[1,5-a]pyrimidin-5-yl)piperazin-1-yl)-3-methoxypropan-1-one (400 mg, 1.04 mmol), 2-methoxypyridine-3-boronic acid (240 mg, 1.56 mmol), potassium carbonate (435 mg, 3.12 mmol), Pd(OAc)$_2$ (5 mg, 0.021 mmol), and x-Phos (14 mg, 0.042 mmol) were taken up in 2 mL dioxane and 1 mL water in a sealed tube and heated at 85° C. for 2 hours. Reaction then cooled to room temperature filtered through a celite plug with acetonitrile and DCM, reduced in vacuo. Purified on Shimadzu neutral phase prep lyophilized to get 39 mg as the formic acid salt product. $^1$H NMR (400 MHz, DMSO-d6) δ 8.82 (dd, J=1.89, 7.45 Hz, 1H), 8.76 (d, J=7.83 Hz, 1H), 8.51 (s, 1H), 8.29 (s, 1H), 7.99 (dd, J=1.89, 4.93 Hz, 1H), 7.09 (dd, J=4.93, 7.45 Hz, 1H), 6.84 (d, J=7.83 Hz, 1H), 3.98-4.02 (m, 4H), 3.61-3.85 (m, 8H), 3.31-3.45 (m, 2H) LRMS (ESI) m/z 412 [(M+H)]$^+$, calc'd for C$_{20}$H$_{25}$N$_7$O$_3$: 411.47.

5.6.29. Synthesis of (S)-2-amino-1-(4-(3-(2-methoxypyridin-3-yl)pyrazolo[1,5-a]pyrimidin-5-yl)piperazin-1-yl)-3,3-dimethylbutan-1-one

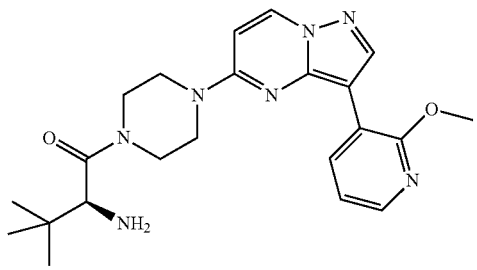 [SMILES: COc1ncccc1-c1cnn2ccc(N3CCN(C(=O)[C@@H](N)C(C)(C)C)CC3)nc12]

Part A. (S)-2-amino-1-(4-(3-bromopyrazolo[1,5-a]pyrimidin-5-yl)piperazin-1-yl)-3,3-dimethylbutan-1-one

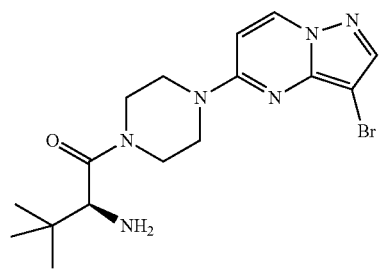 [SMILES: CC(C)(C)[C@H](N)C(=O)N1CCN(c2ccn3ncc(Br)c3n2)CC1]

3-bromo-5-(piperazin-1-yl)pyrazolo[1,5-a]pyrimidine (300 mg, 1.1 mmol) N-Boc-L-tert-Leucine (295 mg, 1.28 mmol), HATU (368 mg, 1.6 mmol), and triethylamine (590 uL, 4.26 mmol) taken up in DMF and stirred at room temperature overnight. Reaction diluted with DCM washed with water, DCM layer then dried over magnesium sulfate filtered and reduced in vacuo. This was then taken up in 26 mL DCM and 4 mL TFA added. Stirred 1 hour until complete by LC/MS. Reaction washed with 1N NaOH, DCM layer removed dried over magnesium sulfate filtered, reduced in vacuo to obtain 420 mg crude product for further reaction as is. LRMS (ESI) m/z 395/397 [(M+H)]+, calc'd for C$_{16}$H$_{23}$BrN$_6$O: 395.31.

Part B. (S)-2-amino-1-(4-(3-(2-methoxypyridin-3-yl)pyrazolo[1,5-a]pyrimidin-5-yl)piperazin-1-yl)-3,3-dimethylbutan-1-one (S)-2-amino-1-(4-(3-bromopyrazolo[1,5-a]pyrimidin-5-yl)piperazin-1-yl)-3,3-dimethylbutan-1-one (420 mg, 1.1 mmol), (2-methoxypyridin-3-yl)boronic acid (240 mg, 1.6 mmol), potassium carbonate (435 mg, 3.2 mmol), Pd(OAc)$_2$ (5 mg, 0.021 mmol), and x-Phos (14 mg, 0.043 mmol) were taken up in 4 mL dioxane and 1 mL water under nitrogen and stirred at 85° C. for 2 hours. Reaction then cooled to room temperature, filtered through celite plug with acetonitrile and DCM. Reduced in vacuo and purified on shimadzu neutral phase prep, lypholized to get 18 mg 1 eq formic salt product. $^1$H NMR (400 MHz, DMSO-d6) δ 8.81 (dd, J=1.77, 7.58 Hz, 1H), 8.75 (d, J=7.83 Hz, 1H), 8.51 (s, 1H), 8.29 (s, 1H), 7.97-8.03 (m, 1H), 7.06-7.09 (m, 1H), 6.83 (d, J=7.83 Hz, 1H), 4.00 (s, 3H), 3.69-3.78 (m, 3H), 3.80 (s, 4H), 3.84 (s, 2H), 0.94 (s, 9H) LRMS (ESI) m/z 424 [(M+H)]$^+$, calc'd for C$_{22}$H$_{29}$N$_7$O$_2$: 423.52.

5.6.30. Synthesis of (R)-Tetrahydrofuran-3-yl 4-(3-(2-methoxypyridin-3-yl)pyrazolo[1,5-a]pyrimidin-5-yl)piperazine-1-carboxylate

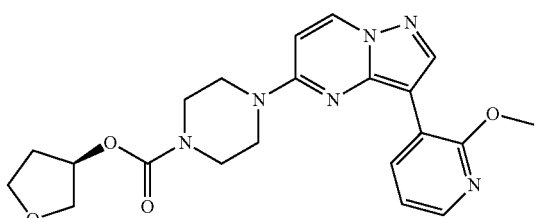

Part A. 4-(3-Bromo-pyrazolo[1,5-a]pyrimidin-5-yl)-piperazine-1-carboxylic acid 4-nitro-phenyl ester

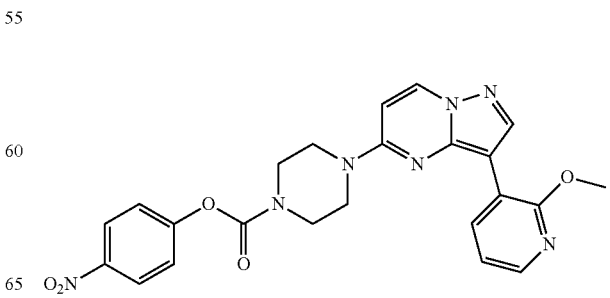

To 2.00 g (7.09 mmol) of 3-bromo-5-piperazin-1-yl-pyrazolo[1,5-a]pyrimidine dissolved in 40 mL of EtOAc at 0° C., was added 1.71 g (8.51 mmol) of 4-nitrophenyl carbonochloridate, followed by 1.97 mL (14.18 mmol) of TEA. After 5 minutes stirring at 0° C., the ice bath was removed, and stirring continued at RT for about 2 hr. It was diluted with 50 mL of 50% EtOAc/hex. The desired product was filtered out, and dried to obtain 3.17 g (100% yield) of an off-white solid.

Part B. 4-(3-Bromo-pyrazolo[1,5-a]pyrimidin-5-yl)-piperazine-1-carboxylic acid (R)-(tetrahydro-furan-3-yl)ester

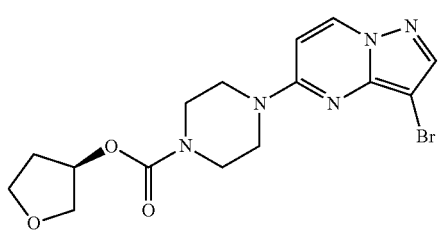 [SMILES: O=C(O[C@@H]1CCOC1)N1CCN(c2ccn3ncc(Br)c3n2)CC1]

To 112 mg (0.25 mmol) of 4-nitrophenyl 4-(3-bromopyrazolo[1,5-a]pyrimidin-5-yl)piperazine-1-carboxylate dissolved in 10 mL of THF, was added (R)-tetrahydrofuran-3-ol (44 mg, 0.5 mmol), followed by 60% NaH (40 mg, 1.0 mmol) and stirred at RT for 2 hr. After 2 hr it was diluted with 20 mL of EtOAc and slowly quench with brine. The organic layer was dried over MgSO₄ and concentrated, it was purified over 12 gram silica gel column eluting with 0-10% MeOH/DCM to obtain 71 mg (72% yield) of the desired product.

Part C. (R)-Tetrahydrofuran-3-yl 4-(3-(2-methoxypyridin-3-yl)pyrazolo[1,5-a]pyrimidin-5-yl)piperazine-1-carboxylate Suzuki coupling reaction was carried out under the same conditions as describe about for the synthesis of 6-[1-(2,2-Dimethyl-propyl)-1H-pyrazol-4-yl]-3-(2-methoxy-pyridin-3-yl)-imidazo-[1,2-]pyridazine yielding 72% of the desired product. ¹H NMR (400 MHz, CHLOROFORM-d) δ ppm 1.98-2.14 (m, 1 H) 2.23 (dtd, J=14.02, 8.17, 8.17, 6.27 Hz, 1 H) 3.66 (d, J=5.02 Hz, 4 H) 3.71-3.82 (m, 4 H) 3.83-4.02 (m, 4 H) 4.10 (s, 3 H) 5.27-5.39 (m, 1 H) 6.38 (d, J=7.78 Hz, 1 H) 7.00 (dd, J=7.53, 5.02 Hz, 1 H) 8.04 (dd, J=4.77, 1.76 Hz, 1 H) 8.37 (d, J=7.78 Hz, 1 H) 8.63 (s, 1 H) 8.73 (dd, J=7.53, 1.76 Hz, 1 H).

5.6.31. Synthesis of 1-Methoxypropan-2-yl 4-(3-(2-methoxypyridin-3-yl)pyrazolo[1,5-a]pyrimidin-5-yl)piperazine-1-carboxylate

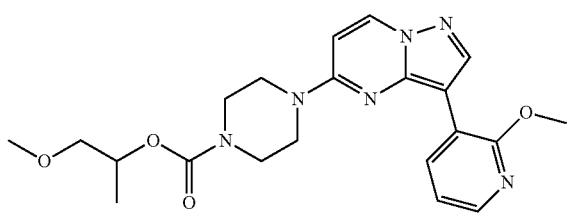

Part A. 1-methoxypropan-2-yl 4-(3-bromopyrazolo[1,5-a]pyrimidin-5-yl)piperazine-1-carboxylate

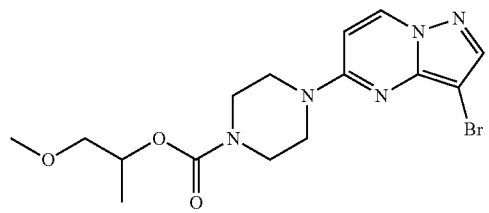 [SMILES: COCC(C)OC(=O)N1CCN(c2ccn3ncc(Br)c3n2)CC1]

This was made by using 1-methoxypropan-2-ol and following the Part B in the procedure described above for making (R)-tetrahydrofuran-3-yl 4-(3-bromopyrazolo[1,5-a]pyrimidin-5-yl)piperazine-1-carboxylate.

Part B. 1-Methoxypropan-2-yl 4-(3-(2-methoxypyridin-3-yl)pyrazolo[1,5-a]pyrimidin-5-yl)piperazine-1-carboxylate The Suzuki coupling reaction was carried out by following the procedure that was used for other examples. ¹H NMR (400 MHz, CHLOROFORM-d) δ ppm 1.29 (d, J=6.57 Hz, 3 H) 3.40 (s, 3 H) 3.42-3.56 (m, 2 H) 3.61-3.70 (m, 4 H) 3.72-3.81 (m, 4 H) 4.10 (s, 3 H) 5.06 (td, J=6.25, 4.17 Hz, 1 H) 6.37 (d, J=7.83 Hz, 1 H) 7.00 (dd, J=7.58, 5.05 Hz, 1 H) 8.03 (dd, J=4.80, 1.77 Hz, 1 H) 8.36 (d, J=7.83 Hz, 1 H) 8.63 (s, 1 H) 8.73 (dd, J=7.45, 1.89 Hz, 1 H).

5.6.32. Synthesis of Tetrahydro-2H-pyran-4-yl 4-(3-(2-methoxypyridin-3-yl)pyrazolo[1,5-a]pyrimidin-5-yl)piperazine-1-carboxylate

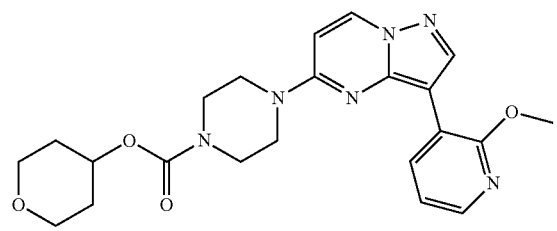 [SMILES: COc1ncccc1-c1cnn2ccc(N3CCN(C(=O)OC4CCOCC4)CC3)nc12]

Part A. Tetrahydro-2H-pyran-4-yl 4-(3-bromopyrazolo[1,5-a]pyrimidin-5-yl)piperazine-1-carboxylate

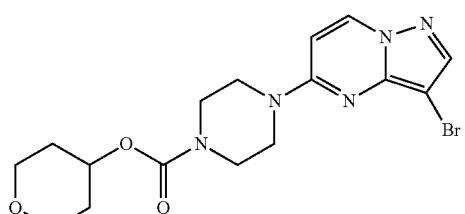

This was made by using tetrahydro-2H-pyran-4-ol and following the Part B in the procedure described above for making (R)-tetrahydrofuran-3-yl 4-(3-bromopyrazolo[1,5-a]pyrimidin-5-yl)piperazine-1-carboxylate.

Part B. Tetrahydro-2H-pyran-4-yl 4-(3-(2-methoxypyridin-3-yl)pyrazolo[1,5-a]pyrimidin-5-yl)piperazine-1-carboxylate This was synthesized by following the Suzuki procedure described above for making (R)-tetrahydrofuran-3-yl 4-(3-(2-methoxypyridin-3-yl)pyrazolo[1,5-a]pyrimidin-5-yl)piperazine-1-carboxylate. $^1$H NMR (400 MHz, CHLOROFORM-d) δ ppm 1.66-1.80 (m, 2 H) 1.95-2.02 (m, 2 H) 3.51-3.62 (m, 2 H) 3.67 (d, J=4.55 Hz, 4 H) 3.71-3.82 (m, 4 H) 3.88-4.00 (m, 2 H) 4.09 (s, 3 H) 4.94 (tt, J=8.43, 3.95 Hz, 1 H) 6.36 (d, J=7.58 Hz, 1 H) 6.99 (dd, J=7.07, 5.31 Hz, 1 H) 8.03 (d, J=4.80 Hz, 1 H) 8.35 (d, J=7.58 Hz, 1 H) 8.62 (s, 1 H) 8.72 (d, J=7.33 Hz, 1 H). LRMS (ESI) m/e 439 [(M+H)$^+$, calcd for $C_{22}H_{26}FN_6O_4$ 438].

5.6.33. Synthesis of (R)-tetrahydrofuran-3-yl-4-(3-(5-fluoro-2-methoxypyridin-3-yl)pyrazolo[1,5-a]pyrimidin-5-yl)piperazine-1-carboxylate

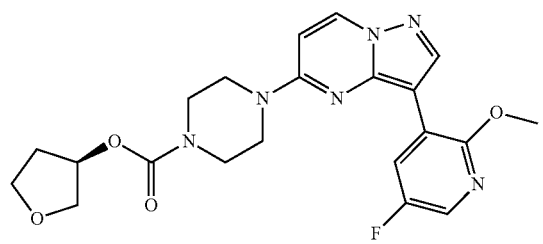 [SMILES: COc1ncc(F)cc1-c1cnn2ccc(N3CCN(C(=O)O[C@@H]4CCOC4)CC3)nc12]

(R)-tetrahydrofuran-3-yl 4-(3-bromopyrazolo[1,5-a]pyrimidin-5-yl)piperazine-1-carboxylate (100 mg, 0.25 mmol), 5-fluoro-2-methoxy-3-(4,4,5,5-tetramethyl-1,3,2-dioxaborolan-2-yl)pyridine (127 mg, 0.5 mmol), triethylamine (211 uL, 1.5 mmol), Pd(OAc)$_2$ (1 mg, 0.0025 mmol), and x-Phos (5 mg, 0.005 mmol) were taken up in 4 mL dioxane and 1 mL water under nitrogen and stirred at 85° C. for 2 hours. Reaction then cooled to room temperature, filtered through celite plug with acetonitrile and DCM. Reduced in vacuo and purified on Shimadzu neutral phase prep, lypholized to get 30 mg product. $^1$H NMR (400 MHz, DMSO-d6) δ 8.80 (d, J=7.83 Hz, 1H), 8.72 (dd, J=3.03, 10.36 Hz, 1H), 8.56 (s, 1H), 7.94 (d, J=3.03 Hz, 1H), 6.86 (d, J=7.83 Hz, 1H), 5.18 (d, J=1.77 Hz, 1H), 4.00 (s, 3H), 3.71-3.83 (m, 8H), 3.32 (s, 2H), 2.08 (s, 1H), 2.13 (s, 1H), 1.89-2.00 (m, 1H) LRMS (ESI) m/z 443 [(M+H)]$^+$, calc'd for $C_{21}H_{23}FN_6O_4$: 442.45.

5.6.34. Synthesis of (S)-tetrahydrofuran-3-yl-4-(3-(2-methoxypyridin-3-yl)pyrazolo[1,5-a]pyrimidin-5-yl)piperazine-1-carboxylate

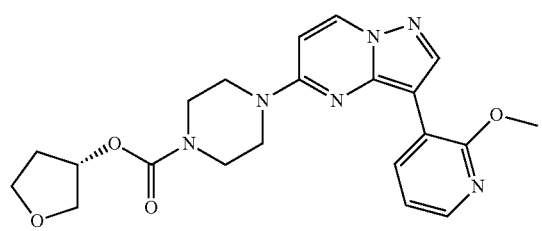 [SMILES: COc1ncccc1-c1cnn2ccc(N3CCN(C(=O)O[C@H]4CCOC4)CC3)nc12]

Part A. (S)-tetrahydrofuran-3-yl 4-(3-bromopyrazolo[1,5-a]pyrimidin-5-yl)piperazine-1-carboxylate

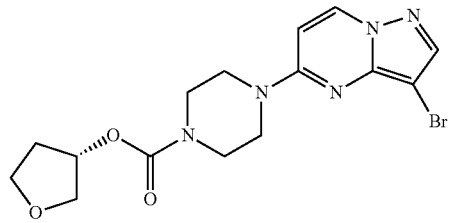 [SMILES: O=C(O[C@H]1CCOC1)N1CCN(c2ccn3ncc(Br)c3n2)CC1]

To 224 mg (0.50 mmol) of 4-nitrophenyl 4-(3-bromopyrazolo[1,5-a]pyrimidin-5-yl)piperazine-1-carboxylate dissolved in 18 mL of THF, was added (S)-tetrahydrofuran-3-ol (88 mg, 1.0 mmol), followed by 60% NaH (80 mg, 2.0 mmol) and stirred at RT for 2 hr. After 2 hr it was diluted with 30 mL of EtOAc and slowly quench with brine. The organic layer was dried over MgSO$_4$ and concentrated, it was purified using a 40 g silica gel column eluting with 0-10% MeOH/DCM to obtain 301 mg (76% yield) of the desired product. 1H NMR (400 MHz, CHLOROFORM-d) δ ppm 2.01-2.13 (m, 1 H) 2.17-2.29 (m, 1 H) 3.57-3.70 (m, 4 H) 3.74-3.84 (m, 4 H) 3.86-4.01 (m, 4 H) 5.27-5.38 (m, 1 H) 6.37 (d, J=7.83 Hz, 1 H) 7.87 (s, 1 H) 8.28 (d, J=7.83 Hz, 1 H)

Part B. (S)-tetrahydrofuran-3-yl 4-(3-(2-methoxypyridin-3-yl)pyrazolo[1,5-a]pyrimidin-5-yl)piperazine-1-carboxylate The Suzuki coupling reaction was carried out under the same conditions as described for the synthesis of LP-943795, yielding 61% of the desired product. $^1$H NMR (400 MHz, CHLOROFORM-d) δ ppm 2.02-2.14 (m, 1 H) 2.16-2.30 (m, 1 H) 3.66 (d, J=4.80 Hz, 4 H) 3.72-3.82 (m, 4 H) 3.84-4.01 (m, 4 H) 4.10 (s, 3 H) 5.33 (td, J=3.85, 1.89 Hz, 1 H) 6.38 (d, J=7.83 Hz, 1 H) 7.01 (dd, J=7.45, 4.93 Hz, 1 H) 8.04 (dd, J=5.05, 1.77 Hz, 1 H) 8.38 (d, J=7.83 Hz, 1 H) 8.64 (s, 1 H) 8.73 (dd, J=7.33, 1.77 Hz, 1 H). LRMS (ESI) m/e 425 [(M+H)$^+$, calcd for $C_{21}H_{24}N_6O_4$ 424].

5.6.35. Synthesis of (S)-1-methoxypropan-2-yl 4-(3-(2-methoxypyridin-3-yl)pyrazolo[1,5-a]pyrimidin-5-yl)piperazine-1-carboxylate

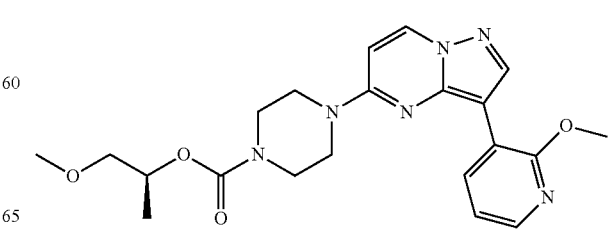

Part A. (S)-1-methoxypropan-2-yl 4-(3-bromopyrazolo[1,5-a]pyrimidin-5-yl)piperazine-1-carboxylate

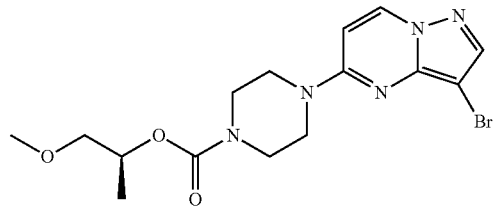 [SMILES: COC[C@H](C)OC(=O)N1CCN(c2ccn3ncc(Br)c3n2)CC1]

This was carried out under same conditions and scale as used above [(S)-tetrahydrofuran-3-yl 4-(3-bromopyrazolo[1,5-a]pyrimidin-5-yl)piperazine-1-carboxylate] to obtain 71% of the desired product. 1H NMR (400 MHz, CHLOROFORM-d) δ ppm 1.29 (d, J=6.27 Hz, 3 H) 3.30-3.41 (m, 3 H) 3.41-3.54 (m, 2 H) 3.58-3.69 (m, 4 H) 3.71-3.83 (m, 4 H) 4.98-5.12 (m, 1 H) 6.35 (d, J=8.03 Hz, 1 H) 7.86 (s, 1 H) 8.26 (d, J=7.78 Hz, 1 H).

Part B. (S)-1-methoxypropan-2-yl 4-(3-(2-methoxypyridin-3-yl)pyrazolo[1,5-a]pyrimidin-5-yl)piperazine-1-carboxylate The Suzuki coupling reaction was carried out under the typical conditions used for the synthesis of other examples, yielding 64% of the desired product. $^1$H NMR (400 MHz, CHLOROFORM-d) δ ppm 1.29 (d, J=6.32 Hz, 3 H) 3.40 (s, 3 H) 3.42-3.54 (m, 2 H) 3.61-3.70 (m, 4 H) 3.71-3.81 (m, 4 H) 4.09 (s, 3 H) 5.06 (quind, J=6.32, 6.32, 6.32, 6.32, 4.04 Hz, 1 H) 6.38 (d, J=7.83 Hz, 1 H) 7.00 (dd, J=7.45, 4.93 Hz, 1H) 8.03 (dd, J=4.93, 1.89 Hz, 1 H) 8.36 (d, J=7.83 Hz, 1 H) 8.63 (s, 1 H) 8.74 (dd, J=7.58, 2.02 Hz, 1 H). LRMS (ESI) m/e 427 [(M+H)+, calcd for $C_{21}H_{26}N_6O_4$ 426].

5.6.36. Synthesis of 2-Methoxyethyl 4-(3-(2-methoxypyridin-3-yl)pyrazolo[1,5-a]pyrimidin-5-yl)piperazine($d_8$)-1-carboxylate

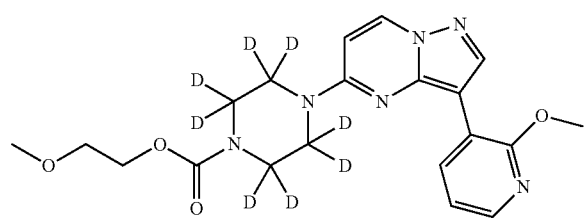

Part A. 3-Bromo-5-(piperazin-1-yl)pyrazolo[1,5-a]pyrimidine(d8

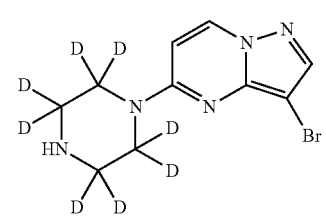 [SMILES: [2H]C1([2H])NC([2H])([2H])C([2H])([2H])N(c2ccn3ncc(Br)c3n2)C1([2H])[2H]]

A mixture of 3-bromo-5-chloropyrazolo[1,5-a]pyrimidine (930 mg, 4 mmol), piperazine-$d_8$HCl (1 g, 6 mmol) and TEA (2.23 mL, 16 mmol) in isopropanol (8 mL) was heated in a microwave oven at 140° C. for 30 min. The mixture was concentrated to give the titled compound that was used for next step without further purification.

Part B. 2-Methoxyethyl 4-(3-bromopyrazolo[1,5-a]pyrimidin-5-yl)piperazine(d8)-1-carboxylate

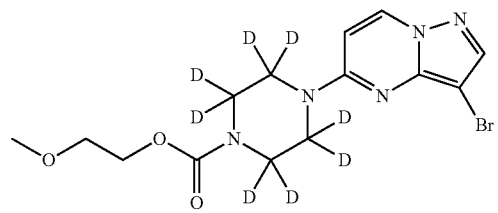 [SMILES: [2H]C1([2H])N(C(=O)OCCOC)C([2H])([2H])C([2H])([2H])N(c2ccn3ncc(Br)c3n2)C1([2H])[2H]]

To a mixture of 3-bromo-5-(piperazin-1-yl)pyrazolo[1,5-a]pyrimidine-$d_8$ (~2 mmol) and DIEA (1.74 mL, 10 mmol) in THF (20 mL) was added methoxyethyl chloroformate (279 uL, 2.4 mmol). The resulting mixture was stirred at rt for overnight. The mixture was concentrated and the residue was subjected to ISCO then prep HPLC to give the titled compound (382 mg). $^1$H NMR (400 MHz, CHLOROFORM-d) δ ppm 3.39 (s, 3 H) 3.57-3.70 (m, 2 H) 4.24-4.31 (m, 2 H) 6.32 (d, J=7.83 Hz, 1 H) 7.84 (s, 1 H) 8.24 (d, J=8.08 Hz, 1 H).

Part C. 2-Methoxyethyl 4-(3-(2-methoxypyridin-3-yl)pyrazolo[1,5-a]pyrimidin-5-yl)piperazine(d8)-1-carboxylate Under typical Suzuki coupling conditions with 2-methoxyethyl 4-(3-bromopyrazolo[1,5-a]pyrimidin-5-yl)piperazine(d8)-1-carboxylate and appropriate boronic acid to provide the titled compound. $^1$H NMR (400 MHz, CHLOROFORM-d) δ ppm 3.41 (s, 3 H) 3.58-3.70 (t, J=3.40 Hz, 2 H) 4.09 (s, 3 H) 4.27-4.32 (t, J=3.40 Hz, 2 H) 6.35 (d, J=7.83 Hz, 1 H) 6.99 (dd, J=7.58, 4.80 Hz, 1 H) 8.02 (dd, J=4.80, 1.77 Hz, 1 H) 8.35 (d, J=7.83 Hz, 1 H) 8.62 (s, 1 H) 8.72 (dd, J=7.45, 1.89 Hz, 1 H). LRMS (ESI) m/e 421.2 [(M+H)$^+$, calcd for $C_{21}H_{26}N_6O_4$ 420.5].

5.6.37. Synthesis of Part A. Isopropyl 4-(3-bromopyrazolo[1,5-a]pyrimidin-5-yl)piperazine(d8)-1-carboxylate

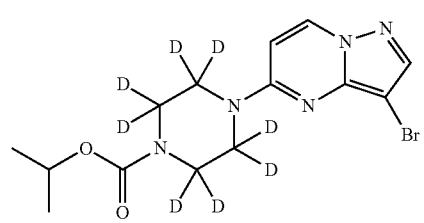 [SMILES: [2H]C1([2H])N(C(=O)OC(C)C)C([2H])([2H])C([2H])([2H])N(c2ccn3ncc(Br)c3n2)C1([2H])[2H]]

To a mixture of 3-bromo-5-(piperazin-1-yl)pyrazolo[1,5-a]pyrimidine-d$_8$ (~2 mmol) and DIEA (1.74 mL, 10 mmol) in THF (20 mL) was added isopropyl chloroformate (2 M solution, 1.2 mL, 2.4 mmol) dropwise. The resulting mixture was stirred at rt for overnight. The mixture was concentrated and the residue was subjected to ISCO to give the titled compound (449 mg). $^1$H NMR (400 MHz, CHLOROFORM-d) δ ppm 1.26 (d J=6.32 Hz, 6 H) 4.90-5.00 (m, 1 H) 6.31 (d, J=7.83 Hz, 1 H) 7.83 (s, 1 H) 8.23 (d, J=7.83 Hz, 1 H).

Part B. Isopropyl 4-(3-(2-methoxy-6-methylpyridin-3-yl)pyrazolo[1,5-a]pyrimidin-5-yl)piperazine(d8)-1-carboxylate Under typical Suzuki coupling conditions with 2-isopropyl 4-(3-bromopyrazolo[1,5-a]pyrimidin-5-yl)piperazine(d8)-1-carboxylate and appropriate boronic acid to provide the titled compound. 1H NMR (400 MHz, CHLOROFORM-d) δ ppm 1.29 (d, J=6.32 Hz, 6 H) 2.48 (s, 3 H) 4.07 (s, 3 H) 4.98 (quin, J=6.25 Hz, 1 H) 6.32 (d, J=7.83 Hz, 1 H) 6.84 (d, J=7.58 Hz, 1 H) 8.33 (d, J=7.83 Hz, 1 H) 8.56-8.60 (m, 2 H). LRMS (ESI) m/e 419.2 [(M+H)+, calcd for $C_{21}H_{26}N_6O_4$ 418.5].

5.6.38. P81 Filter Plate Assay

Compounds were serially diluted into a Labcyte LDV plate (Labcyte, cat# LP-0200) using a Mutiprobe (PerkinElmer) and Biomek FX (Beckman Coulter) so that the highest compound concentration was at 96 μM. Compounds were then pinged (75 mL per well) into a Greiner 384-well reaction plate (Greiner, #781076) using an ECHO 550 Liquid Handler (Labcyte). A total of 12 μl reaction buffer (IMAP buffer containing Tween and DTT, from Molecular Devices) was then added to each well of columns 1 and 13 for the negative controls and 12 μl of 2×AAK1 (0.2 nM full-length human protein, NCBI accession no. NP_055726.2) was added to the remaining wells. Enzyme was then pre-incubated with compound for 10 minutes at RT. Reactions were initiated upon Minitrak (PerkinElmer) addition of 12 μl substrate mix containing 2×Mu2 (0.2 μM, full length human protein), 2× cold ATP (2 μM), and 1.3 μCi of hot $^{33}$P-ATP. Reactions proceeded for one hour at RT. Meanwhile, Millipore 384-well P81 filter plates (Millipore, catalog #MZPHN0W10) were placed on a plate washer (Zoom ZW, from Titertek) and pre-wet with 50 μl 1% phosphoric acid. Kinase reactions were then stopped upon addition of 24 μl of 2% phosphoric acid to each well and the Minitrak was then used to transfer 40 μl from each well into the pre-wet Millipore 384-well P81 filter plates. Reaction mixtures were incubated for 10 minutes at RT in the P81 plates, followed by washing five times with 100 μl/well of 1% phosphoric acid using the Zoom filter washer. The bottom of each filter plate was sealed followed by addition of 20 μl Microscint 40 to each well, sealing the top of the plates with Flashplate cover, and then waiting one hour until reading on the TopCount (PerkinElmer).

5.6.39. HEK281 Cell-Based Assay

HEK293F cells were cultured in media containing DMEM (Gibco, cat. #11965), 10% FBS (SAFC Biosciences, cat. #12103C), 1×GPS (glutamine, penicillin and streptomycin). On day one, cells were plated on a 10 cm dish so that they are ~80% confluent at time of transfection. Roughly 12 million cells were in a 10 cm dish at time of transfection. On day two, each dish was transfected with 48 ug DNA and 144 ul Lipofectamine 2000 (Invitrogen, cat.#11668-019). The DNA was comprised of a mixture (per 10 cm dish) containing 3 ug AAK1/HA/pIRES (full length human, NCBI accession no. NP_055726.2), 45 μg Flag/AP2MI/pcDNA (full length human), and 1.5 ml OPTI-MEM. The Lipofectamine 2000 is made up of a mixture (per 10 cm dish) containing 144 μl Lipofectamine 2000 and 1.5 ml OPTI-MEM. Each mixture was transferred to individual 15 ml tubes and incubated at RT for 5 minutes, and then the two mixes were combined and incubated at RT for 20 minutes. Growth media was then aspirated from each 10 cm plate and replaced with 10 ml of DMEM+10% FBS (no GPS). Finally, 3 ml DNA/Lipofectamine mix was added to each 10 cm dish and mix gently followed by incubate of plate overnight at 37° C. and 5% CO$_2$.

On day three, compounds were diluted in 100% DMSO at 1000× final concentration, followed by 3-fold serial dilutions for a total of 5 concentrations tested. Four compounds were tested per 10 cm dish. One ul of each compound dilution was then pipetted into a deep-well, 96-well plate, followed by addition of 500 μl DMEM+0.5% FBS into each well for a 2× final concentration of each compound. Cells were resuspended in a 10 cm dish by simple pipetting (HEK293 cells come off the plate that easy at this point) and then transferred to a 50 ml conical tube and pelleted by centrifugation at 1000 rpm for 5 min. Cell pellets were then resuspended in 2.75 ml DMEM+0.5% FBS per 10 cm dish and 100 μl of cell suspension transferred into each well of 96-well TC plate. Finally, 100 μl of 2× compound diluted in DMEM+0.5% FBS was then added into wells containing cell suspension for a 1× final concentration. Plates were then incubated at 37° C. and 5% CO$_2$ for 3 hours followed by transferring of cell suspensions from each well into 12-tube PCR strips. The PCR strips were spun in a tip rack at 1000 rpm for 5 minutes to pellet cells and media was then removed by pipetting without disturbing the cell pellet.

To prepare for Western Blot analysis, cell pellets were resuspend in 40 ul 1×LDS-PAGE sample buffer (Invitrogen, cat.# NP0008)+2× Halt phophatase and protease inhibitor cocktail (Thermo Scientific, cat.#1861284), followed by sonicating each with microtip sonicator set at 5 for 8-10 seconds. Five ul of 10× NuPage Sample Reducing Agent (with 50 mM DTT) was to each sample followed by heat denaturing at 70 C for 10 min on PCR machine. A total of 10 μl per sample was loaded into each lane of a 4-20% Tris-Glycine Criterion 26-well gel (Biorad, cat.#345-0034) for the phospho-mu2 blot and 10 μl per lane in a 4-12% Bis-Tris (+MES buffer) NuPAGE 26-well gel (Invitrogen, cat.# WG1403BX10) for the mu2 blot. For controls, 2 ng of phospho-mu2 or 20 ng mu2/Flag proteins were loaded in the last well of each gel. After SDS-PAGE, samples on each gel were transferred to PVDF membrane using an iBlot and membranes were blocked for one hour in TBST+5% milk, followed by wash 3× for 5-10 min with TBST. Criterion gels were probed with rabbit anti-phospho-mu2 (1:5000; a rabbit polyclonal antibody produced by New England Peptide and affinity purified at Lexicon) in TBST+5% BSA, whereas, NuPAGE gels were probed with mouse anti-Flag (1:500; Sigma, cat.# F1804) in TBST+5% milk, and these primary antibodies were incubated overnight at 4° C. on a rocker.

On day four, Western blots were washed 3× for 5-10 minutes with TBST, probe with anti-rabbit-HRP (1:2000; Bio-Rad, cat.#170-6515) or anti-mouse-HRP (1:2000; Biorad, cat.#170-6516) in TBST+5% milk for 1 hour at RT, washed 3× for 10 minutes with TBST, and developed with ECL reagent (GE Healthcare, cat.# RPN2132) on a Versadoc.

Finally, the camera was set up to take a picture every 30 seconds for 10 minutes and the best image saved for each blot with no saturated signal (when the signal is saturated, the bands will be highlighted red). A volume analysis on each band was performed to obtain density values. Percent inhibition was calculated for each sample by first normalizing to total Mu2 expression levels and then comparing to 0% and 100% controls. IC$_{50}$ values were then calculated using Excel fitting software.

5.6.40. In Vitro Data

In vitro data obtained for various compounds of the invention are provided below in Table 1, wherein "MW" means molecular weight, "P81 Assay" refers to the P81 filter plate assay described above, "CBA" refers to the HEK281 cell-based assay described above, "--" means that results for the given assay were not obtained, "*" means less than or equal to 1.0 μM, "" means a value of less than or equal to 0.1 μM, and "*" means less than or equal to 0.01 μM.

TABLE 1

| Compound | MW | CBA IC$_{50}$ μM | P81 IC$_{50}$ μM |
|---|---|---|---|
| (4-(3-(2-methoxypyridin-3-yl)pyrazolo[1,5-a]pyrimidin-5-yl)piperazin-1-yl)(pyrrolidin-1-yl)methanone | 407.5 | ** | *** |
| (S)-1-(2-(((3-(2-methoxyphenyl)pyrazolo[1,5-a]pyrimidin-5-yl)amino)methyl)pyrrolidin-1-yl)butan-1-one | 393.5 | ** | *** |
| (S)-1-(2-(((3-(2-methoxyphenyl)pyrazolo[1,5-a]pyrimidin-5-yl)amino)methyl)pyrrolidin-1-yl)-3,3-dimethylbutan-1-one | 421.5 | *** | *** |
| (S)-1-(3,3-dimethylbutyl)-5-(((3-(2-ethoxyphenyl)pyrazolo[1,5-a]pyrimidin-5-yl)amino)methyl)pyrrolidin-2-one | 435.6 | ** | *** |
| (S)-1-(3,3-dimethylbutyl)-5-(((3-(2-methoxyphenyl)pyrazolo[1,5-a]pyrimidin-5-yl)amino)methyl)pyrrolidin-2-one | 421.5 | *** | *** |
| (S)-1-(3,3-dimethylbutyl)-5-(((3-(2-methoxypyridin-3-yl)pyrazolo[1,5-a]pyrimidin-5-yl)amino)methyl)pyrrolidin-2-one | 422.5 | ** | *** |
| (S)-1-(3,3-dimethylbutyl)-5-(((3-(3-methoxypyridin-4-yl)pyrazolo[1,5-a]pyrimidin-5-yl)amino)methyl)pyrrolidin-2-one | 422.5 | ** | *** |
| (S)-1-(3,3-dimethylbutyl)-5-(((3-phenylpyrazolo[1,5-a]pyrimidin-5-yl)amino)methyl)pyrrolidin-2-one | 391.5 | — | *** |
| (S)-2-(((3-bromopyrazolo[1,5-a]pyrimidin-5-yl)amino)methyl)-N-(tert-butyl)pyrrolidine-1-carboxamide | 395.3 | *** | *** |
| (S)-2-cyclopropyl-N-methyl-N-(1-(3-(pyridin-2-yl)pyrazolo[1,5-a]pyrimidin-5-yl)pyrrolidin-3-yl)acetamide | 376.5 | — | ** |
| (S)-3,3,3-trifluoro-1-(2-(((3-(2-methoxyphenyl)pyrazolo[1,5-a]pyrimidin-5-yl)amino)methyl)pyrrolidin-1-yl)propan-1-one | 433.4 | ** | *** |
| (S)-3,3,3-trifluoro-1-(2-(((3-(pyridin-4-yl)pyrazolo[1,5-a]pyrimidin-5-yl)amino)methyl)pyrrolidin-1-yl)propan-1-one | 404.4 | ** | *** |
| (S)-3,3,3-trifluoro-N-(1-(3-(2-methoxyphenyl)pyrazolo[1,5-a]pyrimidin-5-yl)pyrrolidin-3-yl)-N-methylpropanamide | 433.4 | — | ** |
| (S)-3,3,3-trifluoro-N-(1-(3-(2-methoxypyridin-3-yl)pyrazolo[1,5-a]pyrimidin-5-yl)pyrrolidin-3-yl)-N-methylpropanamide | 434.4 | *** | *** |
| (S)-3,3,3-trifluoro-N-methyl-N-(1-(3-(pyridin-2-yl)pyrazolo[1,5-a]pyrimidin-5-yl)pyrrolidin-3-yl)propanamide | 404.4 | *** | *** |
| (S)-5-(((3-bromopyrazolo[1,5-a]pyrimidin-5-yl)amino)methyl)-1-(3,3-dimethylbutyl)pyrrolidin-2-one | 394.3 | ** | *** |
| (S)-ethyl 2-(((3-(2-methoxyphenyl)pyrazolo[1,5-a]pyrimidin-5-yl)amino)methyl)pyrrolidine-1-carboxylate | 395.5 | *** | *** |
| (S)-isopropyl (1-(3-(2-methoxyphenyl)pyrazolo[1,5-a]pyrimidin-5-yl)pyrrolidin-3-yl)(methyl)carbamate | 409.5 | — | ** |
| (S)-isopropyl (1-(3-(2-methoxypyridin-3-yl)pyrazolo[1,5-a]pyrimidin-5-yl)pyrrolidin-3-yl)(methyl)carbamate | 410.5 | — | ** |
| (S)-isopropyl 2-(((3-(2-methoxyphenyl)pyrazolo[1,5-a]pyrimidin-5-yl)amino)methyl)pyrrolidine-1-carboxylate | 409.5 | *** | *** |
| (S)-isopropyl methyl(1-(3-(pyridin-2-yl)pyrazolo[1,5-a]pyrimidin-5-yl)pyrrolidin-3-yl)carbamate | 380.4 | — | * |
| (S)-isopropyl methyl(1-(3-(pyridin-4-yl)pyrazolo[1,5-a]pyrimidin-5-yl)pyrrolidin-3-yl)carbamate | 380.4 | — | ** |
| (S)-methyl 2-(((3-(2-methoxyphenyl)pyrazolo[1,5-a]pyrimidin-5-yl)amino)methyl)pyrrolidine-1-carboxylate | 381.4 | ** | *** |
| (S)-N-(1-(3-(2-methoxyphenyl)pyrazolo[1,5-a]pyrimidin-5-yl)pyrrolidin-3-yl)-N-methylbutyramide | 393.5 | * | *** |
| (S)-N-(1-(3-(2-methoxypyridin-3-yl)pyrazolo[1,5-a]pyrimidin-5-yl)pyrrolidin-3-yl)-N-methylbutyramide | 394.5 | * | *** |
| (S)-N-(1-(3-bromopyrazolo[1,5-a]pyrimidin-5-yl)pyrrolidin-3-yl)-3,3,3-trifluoro-N-methylpropanamide | 406.2 | — | ** |
| (S)-N-(1-(3-bromopyrazolo[1,5-a]pyrimidin-5-yl)pyrrolidin-3-yl)-N-methylpyrrolidine-1-carboxamide | 393.3 | — | ** |
| (S)-N-(tert-butyl)-2-(((3-(2-methoxyphenyl)pyrazolo[1,5-a]pyrimidin-5-yl)amino)methyl)pyrrolidine-1-carboxamide | 422.5 | ** | *** |

TABLE 1-continued

| Compound | MW | CBA IC$_{50}$ μM | P81 IC$_{50}$ μM |
|---|---|---|---|
| (S)-N-methyl-N-(1-(3-(pyridin-2-yl)pyrazolo[1,5-a]pyrimidin-5-yl)pyrrolidin-3-yl)butyramide | 364.4 | — | * |
| (S)-tert-butyl (1-(3-(2-methoxyphenyl)pyrazolo[1,5-a]pyrimidin-5-yl)pyrrolidin-3-yl)(methyl)carbamate | 423.5 | ** | *** |
| (S)-tert-butyl 2-(((3-(2-(methoxymethyl)phenyl)pyrazolo[1,5-a]pyrimidin-5-yl)amino)methyl)pyrrolidine-1-carboxylate | 437.5 | ** | *** |
| (S)-tert-butyl 2-(((3-(2-ethylphenyl)pyrazolo[1,5-a]pyrimidin-5-yl)amino)methyl)pyrrolidine-1-carboxylate | 421.5 | ** | *** |
| (S)-tert-butyl 2-(((3-(2-hydroxyphenyl)pyrazolo[1,5-a]pyrimidin-5-yl)amino)methyl)pyrrolidine-1-carboxylate | 409.5 | ** | *** |
| (S)-tert-butyl 2-(((3-(2-isopropoxyphenyl)pyrazolo[1,5-a]pyrimidin-5-yl)amino)methyl)pyrrolidine-1-carboxylate | 451.6 | *** | *** |
| (S)-tert-butyl 2-(((3-(2-methoxyphenyl)pyrazolo[1,5-a]pyrimidin-5-yl)amino)methyl)pyrrolidine-1-carboxylate | 423.5 | *** | — |
| (S)-tert-butyl 2-(((3-(3-methoxyphenyl)pyrazolo[1,5-a]pyrimidin-5-yl)amino)methyl)pyrrolidine-1-carboxylate | 423.5 | *** | *** |
| (S)-tert-butyl 2-(((3-(4-(aminomethyl)phenyl)pyrazolo[1,5-a]pyrimidin-5-yl)amino)methyl)pyrrolidine-1-carboxylate | 422.5 | *** | *** |
| (S)-tert-butyl 2-(((3-(4-carbamoylphenyl)pyrazolo[1,5-a]pyrimidin-5-yl)amino)methyl)pyrrolidine-1-carboxylate | 436.5 | * | *** |
| (S)-tert-butyl 2-(((3-(4-methoxyphenyl)pyrazolo[1,5-a]pyrimidin-5-yl)amino)methyl)pyrrolidine-1-carboxylate | 423.5 | *** | *** |
| (S)-tert-butyl 2-(((3-(4-methoxypyridin-3-yl)pyrazolo[1,5-a]pyrimidin-5-yl)amino)methyl)pyrrolidine-1-carboxylate | 424.5 | *** | *** |
| (S)-tert-butyl 2-(((3-(pyridin-4-yl)pyrazolo[1,5-a]pyrimidin-5-yl)amino)methyl)pyrrolidine-1-carboxylate | 394.5 | *** | — |
| (S)-tert-butyl 2-(((3-(pyridin-4-yl)pyrazolo[1,5-a]pyrimidin-5-yl)amino)methyl)pyrrolidine-1-carboxylate | 394.5 | *** | — |
| (S)-tert-butyl 2-(((3-(trifluoromethyl)pyrazolo[1,5-a]pyrimidin-5-yl)amino)methyl)pyrrolidine-1-carboxylate | 385.4 | ** | *** |
| (S)-tert-butyl 2-(((3-iodopyrazolo[1,5-a]pyrimidin-5-yl)amino)methyl)pyrrolidine-1-carboxylate | 443.3 | ** | — |
| (S)-tert-butyl 2-(((3-phenylpyrazolo[1,5-a]pyrimidin-5-yl)amino)methyl)pyrrolidine-1-carboxylate | 393.5 | ** | *** |
| (S)-tert-butyl methyl(1-(3-(2-methylpyridin-4-yl)pyrazolo[1,5-a]pyrimidin-5-yl)pyrrolidin-3-yl)carbamate | 408.5 | ** | *** |
| (S)-tert-butyl methyl(1-(3-(pyridin-2-yl)pyrazolo[1,5-a]pyrimidin-5-yl)pyrrolidin-3-yl)carbamate | 394.5 | — | * |
| 1-(4-(3-(2-methoxypyridin-3-yl)pyrazolo[1,5-a]pyrimidin-5-yl)piperazin-1-yl)-3-methylbutan-1-one | 394.5 | ** | *** |
| 2,2,2-trifluoroethyl 4-(3-(2-methoxypyridin-3-yl)pyrazolo[1,5-a]pyrimidin-5-yl)piperazine-1-carboxylate | 436.4 | *** | *** |
| 2-fluoroethyl 4-(3-(2-methoxypyridin-3-yl)pyrazolo[1,5-a]pyrimidin-5-yl)piperazine-1-carboxylate | 400.4 | *** | *** |
| 2-methoxyethyl 4-(3-(2-methoxyphenyl)pyrazolo[1,5-a]pyrimidin-5-yl)piperazine-1-carboxylate | 411.5 | — | *** |
| 2-methoxyethyl 4-(3-(2-methoxypyridin-3-yl)pyrazolo[1,5-a]pyrimidin-5-yl)piperazine-1-carboxylate | 412.4 | ** | *** |
| 3-(2-methoxypyridin-3-yl)-N-(4,4,4-trifluorobutyl)pyrazolo[1,5-a]pyrimidin-5-amine | 351.3 | ** | *** |
| 3-(3-methoxypyridin-4-yl)-N-(2-(trifluoromethoxy)phenethyl)pyrazolo[1,5-a]pyrimidin-5-amine | 429.4 | *** | — |
| 3-(4-(aminomethyl)phenyl)-N-(2-(cyclopentyloxy)ethyl)pyrazolo[1,5-a]pyrimidin-5-amine | 351.4 | ** | — |
| 3-(4-(aminomethyl)phenyl)-N-(2-(neopentyloxy)ethyl)pyrazolo[1,5-a]pyrimidin-5-amine | 353.5 | ** | — |
| 3-(4-(aminomethyl)phenyl)-N-(2-(tert-butoxy)ethyl)pyrazolo[1,5-a]pyrimidin-5-amine | 339.4 | ** | — |
| 3-(4-(aminomethyl)phenyl)-N-(2-(trifluoromethoxy)phenethyl)pyrazolo[1,5-a]pyrimidin-5-amine | 427.4 | *** | — |
| 3-(4-(aminomethyl)phenyl)-N-(2-methoxyethyl)pyrazolo[1,5-a]pyrimidin-5-amine | 297.4 | ** | — |
| 3-(4-(aminomethyl)phenyl)-N-(3-(cyclopentyloxy)propyl)pyrazolo[1,5-a]pyrimidin-5-amine | 365.5 | ** | — |
| 3-(4-(aminomethyl)phenyl)-N-butylpyrazolo[1,5-a]pyrimidin-5-amine | 295.4 | ** | — |
| 3-(4-methoxypyridin-3-yl)-N-(2-(trifluoromethoxy)phenethyl)pyrazolo[1,5-a]pyrimidin-5-amine | 429.4 | ** | — |
| 3-bromo-N-((1-(2,2,2-trifluoroethyl)pyrrolidin-2-yl)methyl)pyrazolo[1,5-a]pyrimidin-5-amine | 378.2 | ** | *** |
| 3-bromo-N-(3-(cyclopentyloxy)propyl)pyrazolo[1,5-a]pyrimidin-5-amine | 339.2 | * | — |
| 4-(5-(butylamino)pyrazolo[1,5-a]pyrimidin-3-yl)-N-(2-(methylamino)ethyl)benzamide | 366.5 | ** | — |

TABLE 1-continued

| Compound | MW | CBA IC$_{50}$ μM | P81 IC$_{50}$ μM |
|---|---|---|---|
| 5-(4-(isobutylsulfonyl)piperazin-1-yl)-3-(2-methoxypyridin-3-yl)pyrazolo[1,5-a]pyrimidine | 430.5 | | ** |
| cyclopentyl 4-(3-(2-methoxypyridin-3-yl)pyrazolo[1,5-a]pyrimidin-5-yl)piperazine-1-carboxylate | 422.5 | *** | *** |
| ethyl 4-(3-(2-ethoxypyridin-3-yl)pyrazolo[1,5-a]pyrimidin-5-yl)piperazine-1-carboxylate | 396.4 | *** | *** |
| ethyl 4-(3-(2-methoxypyridin-3-yl)pyrazolo[1,5-a]pyrimidin-5-yl)piperazine-1-carboxylate | 382.4 | ** | *** |
| ethyl 5-(4-(isopropoxycarbonyl)piperazin-1-yl)pyrazolo[1,5-a]pyrimidine-3-carboxylate | 361.4 | | ** |
| ethyl methyl(2-((3-(4-(methylcarbamoyl)phenyl)pyrazolo[1,5-a]pyrimidin-5-yl)amino)ethyl)carbamate | 396.4 | ** | — |
| isobutyl (2-((3-(4-carbamoylphenyl)pyrazolo[1,5-a]pyrimidin-5-yl)amino)ethyl)(methyl)carbamate | 410.5 | *** | — |
| isobutyl methyl(2-((3-(4-(methylcarbamoyl)phenyl)pyrazolo[1,5-a]pyrimidin-5-yl)amino)ethyl)carbamate | 424.5 | * | — |
| isopropyl (1-(3-(2-methoxypyridin-3-yl)pyrazolo[1,5-a]pyrimidin-5-yl)azetidin-3-yl)(methyl)carbamate | 396.4 | — | ** |
| isopropyl (2-((3-(3-methoxypyridin-4-yl)pyrazolo[1,5-a]pyrimidin-5-yl)amino)ethyl)(methyl)carbamate | 384.4 | *** | — |
| isopropyl (2-((3-(4-(aminomethyl)phenyl)pyrazolo[1,5-a]pyrimidin-5-yl)amino)ethyl)(methyl)carbamate | 382.5 | ** | — |
| isopropyl (2-((3-(4-carbamoylphenyl)pyrazolo[1,5-a]pyrimidin-5-yl)amino)ethyl)(methyl)carbamate | 396.4 | *** | — |
| isopropyl (2-((3-(4-methoxypyridin-3-yl)pyrazolo[1,5-a]pyrimidin-5-yl)amino)ethyl)(methyl)carbamate | 384.4 | ** | — |
| isopropyl 4-(3-(1,3,5-trimethyl-1H-pyrazol-4-yl)pyrazolo[1,5-a]pyrimidin-5-yl)piperazine-1-carboxylate | 397.5 | — | ** |
| isopropyl 4-(3-(1-isobutyl-1H-pyrazol-4-yl)pyrazolo[1,5-a]pyrimidin-5-yl)piperazine-1-carboxylate | 411.5 | — | ** |
| isopropyl 4-(3-(1-methyl-2-oxo-1,2-dihydropyridin-3-yl)pyrazolo[1,5-a]pyrimidin-5-yl)piperazine-1-carboxylate | 396.4 | ** | *** |
| isopropyl 4-(3-(2-(methoxymethyl)phenyl)pyrazolo[1,5-a]pyrimidin-5-yl)piperazine-1-carboxylate | 409.5 | — | * |
| isopropyl 4-(3-(2-(methylthio)pyridin-3-yl)pyrazolo[1,5-a]pyrimidin-5-yl)piperazine-1-carboxylate | 412.5 | — | ** |
| isopropyl 4-(3-(2,6-dimethoxypyridin-3-yl)pyrazolo[1,5-a]pyrimidin-5-yl)piperazine-1-carboxylate | 426.5 | *** | *** |
| isopropyl 4-(3-(2-aminopyridin-3-yl)pyrazolo[1,5-a]pyrimidin-5-yl)piperazine-1-carboxylate | 381.4 | — | ** |
| isopropyl 4-(3-(2-chloropyridin-3-yl)pyrazolo[1,5-a]pyrimidin-5-yl)piperazine-1-carboxylate | 400.9 | * | ** |
| isopropyl 4-(3-(2-ethoxypyridin-3-yl)pyrazolo[1,5-a]pyrimidin-5-yl)piperazine-1-carboxylate | 410.5 | ** | *** |
| isopropyl 4-(3-(2-fluoropyridin-3-yl)pyrazolo[1,5-a]pyrimidin-5-yl)piperazine-1-carboxylate | 384.4 | ** | *** |
| isopropyl 4-(3-(2-hydroxypyridin-3-yl)pyrazolo[1,5-a]pyrimidin-5-yl)piperazine-1-carboxylate | 382.4 | ** | *** |
| isopropyl 4-(3-(2-isopropoxypyridin-3-yl)pyrazolo[1,5-a]pyrimidin-5-yl)piperazine-1-carboxylate | 424.5 | ** | *** |
| isopropyl 4-(3-(2-methoxy-5-methylpyridin-3-yl)pyrazolo[1,5-a]pyrimidin-5-yl)piperazine-1-carboxylate | 410.5 | *** | *** |
| isopropyl 4-(3-(2-methoxy-6-methylpyridin-3-yl)pyrazolo[1,5-a]pyrimidin-5-yl)piperazine-1-carboxylate | 410.5 | ** | *** |
| isopropyl 4-(3-(2-methoxyphenyl)pyrazolo[1,5-a]pyrimidin-5-yl)piperazine-1-carboxylate | 395.5 | — | *** |
| isopropyl 4-(3-(2-methoxypyridin-3-yl)pyrazolo[1,5-a]pyrimidin-5-yl)piperazine-1-carboxylate | 396.4 | — | *** |
| isopropyl 4-(3-(2-methoxypyridin-3-yl)pyrazolo[1,5-a]pyrimidin-5-yl)-3-oxopiperazine-1-carboxylate | 410.4 | *** | *** |
| isopropyl 4-(3-(2-methoxypyridin-3-yl)pyrazolo[1,5-a]pyrimidin-5-yl)-2,2-dimethylpiperazine-1-carboxylate | 424.5 | — | ** |
| isopropyl 4-(3-(2-methylpyridin-3-yl)pyrazolo[1,5-a]pyrimidin-5-yl)piperazine-1-carboxylate | 380.4 | — | ** |
| isopropyl 4-(3-(3,6-dimethoxypyridazin-4-yl)pyrazolo[1,5-a]pyrimidin-5-yl)piperazine-1-carboxylate | 427.5 | *** | *** |
| isopropyl 4-(3-(3-ethoxyphenyl)pyrazolo[1,5-a]pyrimidin-5-yl)piperazine-1-carboxylate | 409.5 | — | *** |
| isopropyl 4-(3-(3-fluoro-2-methoxyphenyl)pyrazolo[1,5-a]pyrimidin-5-yl)piperazine-1-carboxylate | 413.4 | — | ** |
| isopropyl 4-(3-(3-methoxypyridin-2-yl)pyrazolo[1,5-a]pyrimidin-5-yl)piperazine-1-carboxylate | 396.4 | — | * |
| isopropyl 4-(3-(3-methoxypyridin-4-yl)pyrazolo[1,5-a]pyrimidin-5-yl)piperazine-1-carboxylate | 396.4 | ** | *** |
| isopropyl 4-(3-(4-fluoropyridin-3-yl)pyrazolo[1,5-a]pyrimidin-5-yl)piperazine-1-carboxylate | 384.4 | — | ** |

TABLE 1-continued

| Compound | MW | CBA IC$_{50}$ μM | P81 IC$_{50}$ μM |
|---|---|---|---|
| isopropyl 4-(3-(4-methoxypyridin-2-yl)pyrazolo[1,5-a]pyrimidin-5-yl)piperazine-1-carboxylate | 396.4 | — | *** |
| isopropyl 4-(3-(4-methoxypyridin-3-yl)pyrazolo[1,5-a]pyrimidin-5-yl)piperazine-1-carboxylate | 396.4 | ** | *** |
| isopropyl 4-(3-(5-fluoro-2-methoxyphenyl)pyrazolo[1,5-a]pyrimidin-5-yl)piperazine-1-carboxylate | 413.4 | *** | *** |
| isopropyl 4-(3-(5-fluoro-2-methoxypyridin-3-yl)pyrazolo[1,5-a]pyrimidin-5-yl)piperazine-1-carboxylate | 414.4 | ** | *** |
| isopropyl 4-(3-(5-fluoropyridin-3-yl)pyrazolo[1,5-a]pyrimidin-5-yl)piperazine-1-carboxylate | 384.4 | — | *** |
| isopropyl 4-(3-(5-methoxypyridin-2-yl)pyrazolo[1,5-a]pyrimidin-5-yl)piperazine-1-carboxylate | 396.4 | *** | *** |
| isopropyl 4-(3-(5-methoxypyridin-3-yl)pyrazolo[1,5-a]pyrimidin-5-yl)piperazine-1-carboxylate | 396.4 | ** | *** |
| isopropyl 4-(3-(6-fluoropyridin-3-yl)pyrazolo[1,5-a]pyrimidin-5-yl)piperazine-1-carboxylate | 384.4 | — | ** |
| isopropyl 4-(3-(6-methoxypyridin-3-yl)pyrazolo[1,5-a]pyrimidin-5-yl)piperazine-1-carboxylate | 396.4 | * | *** |
| isopropyl 4-(3-(ethylcarbamoyl)pyrazolo[1,5-a]pyrimidin-5-yl)piperazine-1-carboxylate | 360.4 | — | ** |
| isopropyl 4-(3-(isopropylcarbamoyl)pyrazolo[1,5-a]pyrimidin-5-yl)piperazine-1-carboxylate | 374.4 | — | * |
| isopropyl 4-(3-(methylcarbamoyl)pyrazolo[1,5-a]pyrimidin-5-yl)piperazine-1-carboxylate | 346.4 | — | ** |
| isopropyl 4-(3-(pyrazin-2-yl)pyrazolo[1,5-a]pyrimidin-5-yl)piperazine-1-carboxylate | 367.4 | — | ** |
| isopropyl 4-(3-(pyridin-2-yl)pyrazolo[1,5-a]pyrimidin-5-yl)piperazine-1-carboxylate | 366.4 | ** | *** |
| isopropyl 4-(3-(pyridin-3-yl)pyrazolo[1,5-a]pyrimidin-5-yl)piperazine-1-carboxylate | 366.4 | — | *** |
| isopropyl 4-(3-(pyridin-4-yl)pyrazolo[1,5-a]pyrimidin-5-yl)piperazine-1-carboxylate | 366.4 | ** | *** |
| isopropyl 4-(3-(pyrimidin-5-yl)pyrazolo[1,5-a]pyrimidin-5-yl)piperazine-1-carboxylate | 367.4 | — | ** |
| isopropyl 4-(3-isopropylpyrazolo[1,5-a]pyrimidin-5-yl)piperazine-1-carboxylate | 331.4 | — | ** |
| isopropyl 4-(pyrazolo[1,5-a]pyrimidin-5-yl)piperazine-1-carboxylate | 289.3 | — | *** |
| isopropyl methyl(2-((3-(4-((2-(methylamino)ethyl)carbamoyl)phenyl)pyrazolo[1,5-a]pyrimidin-5-yl)amino)ethyl)carbamate | 453.5 | ** | — |
| isopropyl methyl(2-((3-(4-(methylcarbamoyl)phenyl)pyrazolo[1,5-a]pyrimidin-5-yl)amino)ethyl)carbamate | 410.5 | *** | — |
| isopropyl methyl(2-((3-(4-(pyrrolidin-2-yl)phenyl)pyrazolo[1,5-a]pyrimidin-5-yl)amino)ethyl)carbamate | 422.5 | *** | — |
| methyl 4-(3-(2-methoxypyridin-3-yl)pyrazolo[1,5-a]pyrimidin-5-yl)piperazine-1-carboxylate | 368.4 | ** | ** |
| N-(2-(cyclopentyloxy)ethyl)-3-(3-methoxypyridin-4-yl)pyrazolo[1,5-a]pyrimidin-5-amine | 353.4 | ** | — |
| N-(2-(tert-butoxy)ethyl)-3-(3-methoxypyridin-4-yl)pyrazolo[1,5-a]pyrimidin-5-amine | 341.4 | ** | — |
| N-(2-aminoethyl)-4-(5-((2-methoxyethyl)amino)pyrazolo[1,5-a]pyrimidin-3-yl)benzamide | 354.4 | * | — |
| N-(2-aminoethyl)-4-(5-((3,3-dimethylbutyl)amino)pyrazolo[1,5-a]pyrimidin-3-yl)benzamide | 380.5 | * | — |
| N-(2-aminoethyl)-4-(5-(butylamino)pyrazolo[1,5-a]pyrimidin-3-yl)benzamide | 352.4 | ** | — |
| N-(2-methoxyethyl)-3-phenylpyrazolo[1,5-a]pyrimidin-5-amine | 268.3 | * | — |
| N-(3-(2-methoxypyridin-3-yl)pyrazolo[1,5-a]pyrimidin-5-yl)-N-(4,4,4-trifluorobutyl)acetamide | 393.4 | — | * |
| N-(3-(cyclopentyloxy)propyl)-3-(3-methoxypyridin-4-yl)pyrazolo[1,5-a]pyrimidin-5-amine | 367.4 | ** | — |
| N-(tert-butyl)-4-(3-(2-methoxypyridin-3-yl)pyrazolo[1,5-a]pyrimidin-5-yl)piperazine-1-carboxamide | 409.5 | ** | *** |
| N-(tert-butyl)-4-(3-(2-methoxypyridin-3-yl)pyrazolo[1,5-a]pyrimidin-5-yl)-N-methylpiperazine-1-carboxamide | 423.5 | ** | *** |
| N-isopropyl-4-(3-(2-methoxypyridin-3-yl)pyrazolo[1,5-a]pyrimidin-5-yl)piperazine-1-carboxamide | 395.5 | *** | *** |
| N-isopropyl-4-(3-(2-methoxypyridin-3-yl)pyrazolo[1,5-a]pyrimidin-5-yl)-N-methylpiperazine-1-carboxamide | 409.5 | ** | *** |
| tert-butyl (1-(3-(2-methoxypyridin-3-yl)pyrazolo[1,5-a]pyrimidin-5-yl)azetidin-3-yl)(methyl)carbamate | 410.5 | — | * |

TABLE 1-continued

| Compound | MW | CBA IC$_{50}$ μM | P81 IC$_{50}$ μM |
|---|---|---|---|
| tert-butyl (2-((3-(3-methoxypyridin-4-yl)pyrazolo[1,5-a]pyrimidin-5-yl)amino)ethyl)(methyl)carbamate | 398.5 | *** | — |
| tert-butyl (2-((3-(4-carbamoylphenyl)pyrazolo[1,5-a]pyrimidin-5-yl)amino)ethyl)(methyl)carbamate | 410.5 | *** | — |
| tert-butyl (2-(4-(5-((2-methoxyethyl)amino)pyrazolo[1,5-a]pyrimidin-3-yl)benzamido)ethyl)carbamate | 454.5 | * | — |
| tert-butyl 4-(3-(2-methoxypyridin-3-yl)pyrazolo[1,5-a]pyrimidin-5-yl)piperazine-1-carboxylate | 410.5 | *** | *** |
| tert-butyl methyl(2-((3-(4-(methylcarbamoyl)phenyl)pyrazolo[1,5-a]pyrimidin-5-yl)amino)ethyl)carbamate | 424.5 | *** | — |
| (4-(3-(2-methoxypyridin-3-yl)pyrazolo[1,5-a]pyrimidin-5-yl)piperazin-1-yl)(piperidin-1-yl)methanone | 421.5 | ** | *** |
| isopropyl 4-(3-(6-methoxypyridin-2-yl)pyrazolo[1,5-a]pyrimidin-5-yl)piperazine-1-carboxylate | 396.4 | ** | *** |
| isopropyl 4-(3-(5-fluoro-2-methoxy-4-methylphenyl)pyrazolo[1,5-a]pyrimidin-5-yl)piperazine-1-carboxylate | 427.5 | *** | *** |
| isopropyl 4-(3-(2,4-dimethoxypyrimidin-5-yl)pyrazolo[1,5-a]pyrimidin-5-yl)piperazine-1-carboxylate | 427.5 | ** | *** |
| isopropyl 4-(3-(3-fluoro-4-methylphenyl)pyrazolo[1,5-a]pyrimidin-5-yl)piperazine-1-carboxylate | 397.4 | — | ** |
| isopropyl 4-(3-iodopyrazolo[1,5-a]pyrimidin-5-yl)piperazine-1-carboxylate | 415.2 | — | ** |
| (S)-isopropyl 2-((methyl(pyrazolo[1,5-a]pyrimidin-5-yl)amino)methyl)pyrrolidine-1-carboxylate | 317.4 | — | * |
| (S)-isopropyl 2-(((3-(2-methoxypyridin-3-yl)pyrazolo[1,5-a]pyrimidin-5-yl)(methyl)amino)methyl)pyrrolidine-1-carboxylate | 424.5 | *** | *** |
| isopropyl 4-(3-(2-methoxypyridin-4-yl)pyrazolo[1,5-a]pyrimidin-5-yl)piperazine-1-carboxylate | 396.4 | — | ** |
| (E)-isopropyl 4-(3-(3-methoxyprop-1-en-1-yl)pyrazolo[1,5-a]pyrimidin-5-yl)piperazine-1-carboxylate | 359.4 | — | * |
| (E)-isopropyl 4-(3-(2-ethoxyvinyl)pyrazolo[1,5-a]pyrimidin-5-yl)piperazine-1-carboxylate | 359.4 | — | ** |
| isopropyl 4-(3-chloropyrazolo[1,5-a]pyrimidin-5-yl)piperazine-1-carboxylate | 323.8 | — | ** |
| isopropyl 4-(3-(2-d$_3$-methoxypyridin-3-yl)pyrazolo[1,5-a]pyrimidin-5-yl)piperazine-1-carboxylate | 399.4 | *** | *** |
| (S)-isopropyl 2-(((3-(2-methoxypyridin-3-yl)pyrazolo[1,5-a]pyrimidin-5-yl)amino)methyl)pyrrolidine-1-carboxylate | 410.5 | *** | *** |
| tert-butyl 4-(3-bromopyrazolo[1,5-a]pyrimidin-5-yl)-d$_8$-piperazine-1-carboxylate | 390.2 | — | ** |
| isopropyl 4-(3-(2-methoxypyridin-3-yl)pyrazolo[1,5-a]pyrimidin-5-yl)-d$_8$-piperazine-1-carboxylate | 404.4 | *** | *** |
| isopropyl 4-(3-(1,6-dimethyl-2-oxo-1,2-dihydropyridin-3-yl)pyrazolo[1,5-a]pyrimidin-5-yl)piperazine-1-carboxylate | 410.5 | — | *** |
| isopropyl 3-(3-(2-methoxypyridin-3-yl)pyrazolo[1,5-a]pyrimidin-5-yl)-2-oxoimidazolidine-1-carboxylate | 396.4 | — | * |
| isopropyl 4-(3-(1H-benzo[d]imidazol-4-yl)pyrazolo[1,5-a]pyrimidin-5-yl)piperazine-1-carboxylate | 405.5 | — | ** |
| 2-isobutyl-7-(3-(2-methoxypyridin-3-yl)pyrazolo[1,5-a]pyrimidin-5-yl)hexahydroimidazo[1,5-a]pyrazin-3(2H)-one | 421.5 | — | *** |
| (1R,5S)-tert-butyl 3-(3-(2-methoxypyridin-3-yl)pyrazolo[1,5-a]pyrimidin-5-yl)-3,6-diazabicyclo[3.1.1]heptane-6-carboxylate | 422.5 | — | ** |
| isopropyl 4-(3-(2-methoxy-4-methylphenyl)pyrazolo[1,5-a]pyrimidin-5-yl)piperazine-1-carboxylate | 409.5 | ** | *** |
| (1R,5S)-isopropyl 3-(3-(2-methoxypyridin-3-yl)pyrazolo[1,5-a]pyrimidin-5-yl)-3,6-diazabicyclo[3.1.1]heptane-6-carboxylate | 408.5 | — | ** |
| isopropyl (2-((3-(2-methoxypyridin-3-yl)pyrazolo[1,5-a]pyrimidin-5-yl)(methyl)amino)ethyl)(methyl)carbamate | 398.5 | — | ** |
| isopropyl 4-(3-(2-(2-methoxyethoxy)phenyl)pyrazolo[1,5-a]pyrimidin-5-yl)piperazine-1-carboxylate | 439.5 | — | ** |
| isopropyl 4-(3-(2-(2-methoxyethoxy)pyridin-3-yl)pyrazolo[1,5-a]pyrimidin-5-yl)piperazine-1-carboxylate | 440.5 | — | ** |
| ethyl 4-(3-(2-methoxy-5-methylpyridin-3-yl)pyrazolo[1,5-a]pyrimidin-5-yl)piperazine-1-carboxylate | 396.4 | ** | *** |
| isopropyl (2-((3-(2-methoxypyridin-3-yl)pyrazolo[1,5-a]pyrimidin-5-yl)amino)ethyl)carbamate | 370.4 | — | ** |
| isopropyl (2-((3-(2-methoxy-6-methylpyridin-3-yl)pyrazolo[1,5-a]pyrimidin-5-yl)(methyl)amino)ethyl)(methyl)carbamate | 412.5 | — | ** |
| isopropyl (2-((3-(2-methoxy-5-methylpyridin-3-yl)pyrazolo[1,5-a]pyrimidin-5-yl)(methyl)amino)ethyl)(methyl)carbamate | 412.5 | — | ** |

TABLE 1-continued

| Compound | MW | CBA IC$_{50}$ μM | P81 IC$_{50}$ μM |
|---|---|---|---|
| isopropyl (2-((3-(5-fluoro-2-methoxypyridin-3-yl)pyrazolo[1,5-a]pyrimidin-5-yl)(methyl)amino)ethyl)(methyl)carbamate | 416.4 | — | *** |
| ethyl 4-(3-(5-fluoro-2-methoxypyridin-3-yl)pyrazolo[1,5-a]pyrimidin-5-yl)piperazine-1-carboxylate | 400.4 | ** | *** |
| ethyl 4-(3-(5-fluoro-2-methoxyphenyl)pyrazolo[1,5-a]pyrimidin-5-yl)piperazine-1-carboxylate | 399.4 | — | *** |
| ethyl 4-(3-(2-methoxy-6-methylpyridin-3-yl)pyrazolo[1,5-a]pyrimidin-5-yl)piperazine-1-carboxylate | 396.4 | ** | *** |
| ethyl 4-(3-(2,6-dimethoxypyridin-3-yl)pyrazolo[1,5-a]pyrimidin-5-yl)piperazine-1-carboxylate | 412.4 | — | *** |
| isopropyl (3-((3-(2-methoxypyridin-3-yl)pyrazolo[1,5-a]pyrimidin-5-yl)(methyl)amino)propyl)(methyl)carbamate | 412.5 | ** | *** |
| isopropyl (3-((3-(2-methoxy-6-methylpyridin-3-yl)pyrazolo[1,5-a]pyrimidin-5-yl)(methyl)amino)propyl)(methyl)carbamate | 426.5 | ** | *** |
| ethyl 4-(3-(2-d$_3$-methoxypyridin-3-yl)pyrazolo[1,5-a]pyrimidin-5-yl)piperazine-1-carboxylate | 385.4 | ** | *** |
| isopropyl 4-(3-(2-(2-(dimethylamino)ethoxy)pyridin-3-yl)pyrazolo[1,5-a]pyrimidin-5-yl)piperazine-1-carboxylate | 453.5 | — | ** |
| isopropyl (3-((3-(5-fluoro-2-methoxypyridin-3-yl)pyrazolo[1,5-a]pyrimidin-5-yl)(methyl)amino)propyl)(methyl)carbamate | 430.5 | — | *** |
| N-(2-(tert-butoxy)ethyl)-3-(2-methoxypyridin-3-yl)pyrazolo[1,5-a]pyrimidin-5-amine | 341.4 | — | *** |
| N-(2-(tert-butoxy)ethyl)-3-(2-methoxy-6-methylpyridin-3-yl)pyrazolo[1,5-a]pyrimidin-5-amine | 355.4 | — | ** |
| tert-butyl (2-((3-(2-methoxypyridin-3-yl)pyrazolo[1,5-a]pyrimidin-5-yl)oxy)ethyl)(methyl)carbamate | 399.4 | — | *** |
| isopropyl (2-((3-(2-methoxypyridin-3-yl)pyrazolo[1,5-a]pyrimidin-5-yl)oxy)ethyl)(methyl)carbamate | 385.4 | — | ** |
| (S)-isopropyl (1-(3-(2,6-dimethoxypyridin-3-yl)pyrazolo[1,5-a]pyrimidin-5-yl)pyrrolidin-3-yl)(methyl)carbamate | 440.5 | — | ** |
| (S)-isopropyl (1-(3-(5-fluoro-2-methoxypyridin-3-yl)pyrazolo[1,5-a]pyrimidin-5-yl)pyrrolidin-3-yl)(methyl)carbamate | 428.5 | — | ** |
| (S)-isopropyl (1-(3-(2-methoxy-5-methylpyridin-3-yl)pyrazolo[1,5-a]pyrimidin-5-yl)pyrrolidin-3-yl)(methyl)carbamate | 424.5 | — | *** |
| (S)-isopropyl (1-(3-(1,6-dimethyl-2-oxo-1,2-dihydropyridin-3-yl)pyrazolo[1,5-a]pyrimidin-5-yl)pyrrolidin-3-yl)(methyl)carbamate | 424.5 | — | * |
| (S)-isopropyl (1-(3-(2-d$_3$-methoxy-6-methylpyridin-3-yl)pyrazolo[1,5-a]pyrimidin-5-yl)pyrrolidin-3-yl)(methyl)carbamate | 424.5 | ** | *** |
| (S)-isopropyl (1-(3-(2-methoxypyridin-3-yl)pyrazolo[1,5-a]pyrimidin-5-yl)pyrrolidin-3-yl)(methyl)carbamate | 413.4 | ** | *** |
| isopropyl 4-(3-(imidazo[1,2-a]pyridin-5-yl)pyrazolo[1,5-a]pyrimidin-5-yl)piperazine-1-carboxylate | 405.5 | — | ** |
| (S)-isopropyl (1-(3-(5-fluoro-2-methoxyphenyl)pyrazolo[1,5-a]pyrimidin-5-yl)pyrrolidin-3-yl)(methyl)carbamate | 427.5 | ** | *** |
| isopropyl 4-(3-(imidazo[1,2-a]pyridin-8-yl)pyrazolo[1,5-a]pyrimidin-5-yl)piperazine-1-carboxylate | 405.5 | — | ** |
| propyl 4-(3-(2-methoxypyridin-3-yl)pyrazolo[1,5-a]pyrimidin-5-yl)piperazine-1-carboxylate | 396.4 | ** | *** |
| propyl 4-(3-(2-methoxy-6-methylpyridin-3-yl)pyrazolo[1,5-a]pyrimidin-5-yl)piperazine-1-carboxylate | 410.5 | *** | *** |
| propyl 4-(3-(5-fluoro-2-methoxypyridin-3-yl)pyrazolo[1,5-a]pyrimidin-5-yl)piperazine-1-carboxylate | 414.4 | ** | *** |
| 3-(2-methoxypyridin-3-yl)-5-(4-(3,3,3-trifluoropropyl)piperazin-1-yl)pyrazolo[1,5-a]pyrimidine | 406.4 | — | * |
| 3-(5-fluoro-2-methoxypyridin-3-yl)-5-(4-(3,3,3-trifluoropropyl)piperazin-1-yl)pyrazolo[1,5-a]pyrimidine | 424.4 | — | * |
| 3-bromo-5-(4-(2,2,2-trifluoroethyl)piperazin-1-yl)pyrazolo[1,5-a]pyrimidine | 364.2 | — | ** |
| 3-(2-methoxypyridin-3-yl)-5-(4-(2,2,2-trifluoroethyl)piperazin-1-yl)pyrazolo[1,5-a]pyrimidine | 392.4 | — | ** |
| 3-(2-methoxy-6-methylpyridin-3-yl)-5-(4-(2,2,2-trifluoroethyl)piperazin-1-yl)pyrazolo[1,5-a]pyrimidine | 406.4 | — | ** |
| 3-(5-fluoro-2-methoxypyridin-3-yl)-5-(4-(2,2,2-trifluoroethyl)piperazin-1-yl)pyrazolo[1,5-a]pyrimidine | 410.4 | — | * |
| tert-butyl 4-(3-(2-d$_3$-methoxypyridin-3-yl)pyrazolo[1,5-a]pyrimidin-5-yl)piperazine-1-carboxylate | 413.4 | *** | *** |
| tert-butyl 4-(3-(2-methoxy-6-methylpyridin-3-yl)pyrazolo[1,5-a]pyrimidin-5-yl)piperazine-1-carboxylate | 424.5 | *** | *** |

TABLE 1-continued

| Compound | MW | CBA IC$_{50}$ μM | P81 IC$_{50}$ μM |
|---|---|---|---|
| tert-butyl 4-(3-(2-ethoxypyridin-3-yl)pyrazolo[1,5-a]pyrimidin-5-yl)piperazine-1-carboxylate | 424.5 | *** | *** |
| tert-butyl 4-(3-(5-fluoro-2-methoxypyridin-3-yl)pyrazolo[1,5-a]pyrimidin-5-yl)piperazine-1-carboxylate | 428.5 | ** | *** |
| tert-butyl 4-(3-(5-fluoro-2-methoxyphenyl)pyrazolo[1,5-a]pyrimidin-5-yl)piperazine-1-carboxylate | 427.5 | *** | *** |
| N-(3-(tert-butoxy)propyl)-3-(2-methoxypyridin-3-yl)pyrazolo[1,5-a]pyrimidin-5-amine | 355.4 | ** | *** |
| N-(3-(tert-butoxy)propyl)-3-(2-methoxy-6-methylpyridin-3-yl)pyrazolo[1,5-a]pyrimidin-5-amine | 369.5 | — | *** |
| 3-bromo-N-(3-(tert-butoxy)propyl)pyrazolo[1,5-a]pyrimidin-5-amine | 327.2 | — | * |
| isopropyl 4-(3-(trifluoromethyl)pyrazolo[1,5-a]pyrimidin-5-yl)piperazine-1-carboxylate | 357.3 | — | * |
| isopropyl 4-(3-(pyridazin-4-yl)pyrazolo[1,5-a]pyrimidin-5-yl)piperazine-1-carboxylate | 367.4 | — | * |
| N-(3-(tert-butoxy)propyl)-3-(2-methoxy-6-methylpyridin-3-yl)-N-methylpyrazolo[1,5-a]pyrimidin-5-amine | 383.5 | — | ** |
| N-(3-(tert-butoxy)propyl)-3-(2-methoxypyridin-3-yl)-N-methylpyrazolo[1,5-a]pyrimidin-5-amine | 369.5 | — | ** |
| 5-isopropyl-3-(4-(3-(2-methoxypyridin-3-yl)pyrazolo[1,5-a]pyrimidin-5-yl)piperazin-1-yl)-1,2,4-oxadiazole | 420.5 | — | ** |
| (S)-2-amino-1-(4-(3-(2-methoxypyridin-3-yl)pyrazolo[1,5-a]pyrimidin-5-yl)piperazin-1-yl)-4-methylpentan-1-one | 423.5 | *** | *** |
| isopropyl 4-(3-(4-(2-aminoethoxy)phenyl)pyrazolo[1,5-a]pyrimidin-5-yl)piperazine-1-carboxylate | 424.5 | ** | *** |
| (S)-2-amino-N-((S)-1-(3-(2-methoxypyridin-3-yl)pyrazolo[1,5-a]pyrimidin-5-yl)pyrrolidin-3-yl)-N,4-dimethylpentanamide | 437.5 | *** | *** |
| (S)-2-amino-N-(2-((3-(2-methoxypyridin-3-yl)pyrazolo[1,5-a]pyrimidin-5-yl)(methyl)amino)ethyl)-N,4-dimethylpentanamide | 425.5 | — | *** |
| (S)-2-amino-1-(4-(3-bromopyrazolo[1,5-a]pyrimidin-5-yl)piperazin-1-yl)-4-methylpentan-1-one | 395.3 | — | ** |
| isopropyl 4-(3-(4-(methoxycarbonyl)phenyl)pyrazolo[1,5-a]pyrimidin-5-yl)piperazine-1-carboxylate | 423.5 | — | ** |
| (S)-2-amino-1-(4-(3-(5-fluoro-2-methoxyphenyl)pyrazolo[1,5-a]pyrimidin-5-yl)piperazin-1-yl)-4-methylpentan-1-one | 440.5 | *** | *** |
| (S)-2-amino-4-methyl-1-(4-(3-phenylpyrazolo[1,5-a]pyrimidin-5-yl)piperazin-1-yl)pentan-1-one | 392.5 | *** | *** |
| isopropyl 4-(3-(4-(aminomethyl)phenyl)pyrazolo[1,5-a]pyrimidin-5-yl)piperazine-1-carboxylate | 394.5 | *** | *** |
| (S)-2-amino-1-(4-(3-(2-methoxypyridin-3-yl)pyrazolo[1,5-a]pyrimidin-5-yl)piperazin-1-yl)-3-methylbutan-1-one | 409.5 | *** | *** |
| (R)-2-amino-1-(4-(3-(2-methoxypyridin-3-yl)pyrazolo[1,5-a]pyrimidin-5-yl)piperazin-1-yl)-4-methylpentan-1-one | 423.5 | — | ** |
| isopropyl 4-(3-(2-fluoro-6-methoxypyridin-3-yl)pyrazolo[1,5-a]pyrimidin-5-yl)piperazine-1-carboxylate | 414.4 | — | ** |
| (S)-2-amino-1-(4-(3-(2-fluorophenyl)pyrazolo[1,5-a]pyrimidin-5-yl)piperazin-1-yl)-3-methylbutan-1-one | 396.5 | *** | *** |
| (S)-2-amino-1-(4-(3-chloropyrazolo[1,5-a]pyrimidin-5-yl)piperazin-1-yl)-4-methylpentan-1-one | 350.8 | — | ** |
| (S)-2-amino-1-(4-(3-fluoropyrazolo[1,5-a]pyrimidin-5-yl)piperazin-1-yl)-4-methylpentan-1-one | 334.4 | — | * |
| 2-methoxyethyl 4-(3-(5-fluoro-2-methoxyphenyl)pyrazolo[1,5-a]pyrimidin-5-yl)piperazine-1-carboxylate | 429.4 | *** | *** |
| 2-methoxyethyl 4-(3-(5-fluoro-2-methoxypyridin-3-yl)pyrazolo[1,5-a]pyrimidin-5-yl)piperazine-1-carboxylate | 430.4 | ** | *** |
| 2-methoxyethyl 4-(3-(2-methoxy-6-methylpyridin-3-yl)pyrazolo[1,5-a]pyrimidin-5-yl)piperazine-1-carboxylate | 426.5 | ** | *** |
| (S)-1-(4-(3-(2-methoxypyridin-3-yl)pyrazolo[1,5-a]pyrimidin-5-yl)piperazin-1-yl)-4-methyl-2-(methylamino)pentan-1-one | 437.5 | *** | *** |
| (S)-2-amino-3-methoxy-1-(4-(3-(2-methoxypyridin-3-yl)pyrazolo[1,5-a]pyrimidin-5-yl)piperazin-1-yl)propan-1-one | 411.5 | *** | *** |
| (1-aminocyclopentyl)(4-(3-(2-methoxypyridin-3-yl)pyrazolo[1,5-a]pyrimidin-5-yl)piperazin-1-yl)methanone | 421.5 | *** | *** |
| (S)-2-amino-1-(4-(3-(2-methoxypyridin-3-yl)pyrazolo[1,5-a]pyrimidin-5-yl)piperazin-1-yl)-3,3-dimethylbutan-1-one | 423.5 | *** | *** |
| 2-amino-1-(4-(3-(2-methoxypyridin-3-yl)pyrazolo[1,5-a]pyrimidin-5-yl)piperazin-1-yl)-2-methylpropan-1-one | 395.5 | — | ** |
| (S)-(4-(3-(2-methoxypyridin-3-yl)pyrazolo[1,5-a]pyrimidin-5-yl)piperazin-1-yl)(pyrrolidin-2-yl)methanone | 407.5 | ** | *** |
| 2-methoxyethyl 4-(3-(2-ethoxypyridin-3-yl)pyrazolo[1,5-a]pyrimidin-5-yl)piperazine-1-carboxylate | 426.5 | — | *** |

TABLE 1-continued

| Compound | MW | CBA IC$_{50}$ μM | P81 IC$_{50}$ μM |
|---|---|---|---|
| (S)-2-amino-1-(4-(3-(3-fluorophenyl)pyrazolo[1,5-a]pyrimidin-5-yl)piperazin-1-yl)-3-methylbutan-1-one | 396.5 | *** | *** |
| (S)-2-amino-3-methyl-1-(4-(3-phenylpyrazolo[1,5-a]pyrimidin-5-yl)piperazin-1-yl)butan-1-one | 378.5 | *** | *** |
| (S)-2-amino-1-(4-(3-(4-fluorophenyl)pyrazolo[1,5-a]pyrimidin-5-yl)piperazin-1-yl)-3-methylbutan-1-one | 396.5 | *** | *** |
| (S)-2-amino-1-(4-(3-(2,5-difluorophenyl)pyrazolo[1,5-a]pyrimidin-5-yl)piperazin-1-yl)-3-methylbutan-1-one | 414.5 | *** | *** |
| (S)-2-amino-1-(4-(3-(2-fluoro-4-methylphenyl)pyrazolo[1,5-a]pyrimidin-5-yl)piperazin-1-yl)-3-methylbutan-1-one | 410.5 | ** | *** |
| (S)-2-amino-1-(4-(3-(2-methoxyphenyl)pyrazolo[1,5-a]pyrimidin-5-yl)piperazin-1-yl)-3-methylbutan-1-one | 408.5 | *** | *** |
| 3-methoxypropyl 4-(3-(2-methoxypyridin-3-yl)pyrazolo[1,5-a]pyrimidin-5-yl)piperazine-1-carboxylate | 426.5 | — | *** |
| 2-ethoxyethyl 4-(3-(2-methoxypyridin-3-yl)pyrazolo[1,5-a]pyrimidin-5-yl)piperazine-1-carboxylate | 426.5 | — | ** |
| 2-(2-methoxyethoxy)ethyl 4-(3-(2-methoxypyridin-3-yl)pyrazolo[1,5-a]pyrimidin-5-yl)piperazine-1-carboxylate | 456.5 | — | ** |
| isopropyl 4-(3-(4-methoxypyrimidin-5-yl)pyrazolo[1,5-a]pyrimidin-5-yl)piperazine-1-carboxylate | 397.4 | — | ** |
| (S)-2-amino-3,3-dimethyl-1-(4-(3-phenylpyrazolo[1,5-a]pyrimidin-5-yl)piperazin-1-yl)butan-1-one | 392.5 | ** | *** |
| (S)-2-amino-1-(4-(3-(2-methoxyphenyl)pyrazolo[1,5-a]pyrimidin-5-yl)piperazin-1-yl)-3,3-dimethylbutan-1-one | 422.5 | *** | *** |
| (S)-2-amino-1-(4-(3-(5-fluoro-2-methoxyphenyl)pyrazolo[1,5-a]pyrimidin-5-yl)piperazin-1-yl)-3,3-dimethylbutan-1-one | 440.5 | *** | *** |
| (S)-1-(4-(3-(2-methoxypyridin-3-yl)pyrazolo[1,5-a]pyrimidin-5-yl)piperazin-1-yl)-3,3-dimethyl-2-(methylamino)butan-1-one | 437.5 | ** | *** |
| (S)-1-(4-(3-(2-methoxypyridin-3-yl)pyrazolo[1,5-a]pyrimidin-5-yl)piperazin-1-yl)-4-methylpentan-2-amine | 409.5 | — | ** |
| (S)-2-amino-1-(4-(3-(5-fluoro-2-methoxyphenyl)pyrazolo[1,5-a]pyrimidin-5-yl)piperazin-1-yl)-3-methylbutan-1-one | 426.5 | *** | *** |
| (1-(3-(2-methoxypyridin-3-yl)pyrazolo[1,5-a]pyrimidin-5-yl)-1H-imidazol-4-yl)methanol | 322.3 | — | ** |
| (R)-tetrahydrofuran-3-yl 4-(3-(2-methoxypyridin-3-yl)pyrazolo[1,5-a]pyrimidin-5-yl)piperazine-1-carboxylate | 424.5 | *** | *** |
| 1-methoxypropan-2-yl 4-(3-(2-methoxypyridin-3-yl)pyrazolo[1,5-a]pyrimidin-5-yl)piperazine-1-carboxylate | 426.5 | *** | *** |
| tetrahydro-2H-pyran-4-yl 4-(3-(2-methoxypyridin-3-yl)pyrazolo[1,5-a]pyrimidin-5-yl)piperazine-1-carboxylate | 438.5 | ** | *** |
| 1-methoxy-2-methylpropan-2-yl 4-(3-(2-methoxypyridin-3-yl)pyrazolo[1,5-a]pyrimidin-5-yl)piperazine-1-carboxylate | 440.5 | * | *** |
| 5-(4-(methoxymethyl)-1H-imidazol-1-yl)-3-(2-methoxypyridin-3-yl)pyrazolo[1,5-a]pyrimidine | 336.3 | — | ** |
| (2S,3R)-2-amino-3-methoxy-1-(4-(3-(2-methoxypyridin-3-yl)pyrazolo[1,5-a]pyrimidin-5-yl)piperazin-1-yl)butan-1-one | 425.5 | ** | *** |
| (S)-(4-(3-(2-methoxypyridin-3-yl)pyrazolo[1,5-a]pyrimidin-5-yl)piperazin-1-yl)(morpholin-3-yl)methanone | 423.5 | — | *** |
| (3-aminotetrahydrofuran-3-yl)(4-(3-(2-methoxypyridin-3-yl)pyrazolo[1,5-a]pyrimidin-5-yl)piperazin-1-yl)methanone | 423.5 | ** | *** |
| 2-(dimethylamino)ethyl 4-(3-(2-methoxypyridin-3-yl)pyrazolo[1,5-a]pyrimidin-5-yl)piperazine-1-carboxylate | 425.5 | — | ** |
| 2-(tert-butoxy)ethyl 4-(3-(2-methoxypyridin-3-yl)pyrazolo[1,5-a]pyrimidin-5-yl)piperazine-1-carboxylate | 454.5 | — | *** |
| 1,3-dimethoxypropan-2-yl 4-(3-(2-methoxypyridin-3-yl)pyrazolo[1,5-a]pyrimidin-5-yl)piperazine-1-carboxylate | 456.5 | — | ** |
| (R)-tetrahydrofuran-3-yl 4-(3-(5-fluoro-2-methoxypyridin-3-yl)pyrazolo[1,5-a]pyrimidin-5-yl)piperazine-1-carboxylate | 442.4 | *** | *** |
| (R)-tetrahydrofuran-3-yl 4-(3-(5-fluoro-2-methoxyphenyl)pyrazolo[1,5-a]pyrimidin-5-yl)piperazine-1-carboxylate | 441.5 | *** | *** |
| (R)-tetrahydrofuran-3-yl 4-(3-(2-methoxy-6-methylpyridin-3-yl)pyrazolo[1,5-a]pyrimidin-5-yl)piperazine-1-carboxylate | 438.5 | ** | *** |
| oxetan-3-yl 4-(3-(2-methoxypyridin-3-yl)pyrazolo[1,5-a]pyrimidin-5-yl)piperazine-1-carboxylate | 410.4 | *** | *** |
| (S)-tetrahydrofuran-3-yl 4-(3-(2-methoxypyridin-3-yl)pyrazolo[1,5-a]pyrimidin-5-yl)piperazine-1-carboxylate | 424.5 | *** | *** |
| (S)-1-methoxypropan-2-yl 4-(3-(2-methoxypyridin-3-yl)pyrazolo[1,5-a]pyrimidin-5-yl)piperazine-1-carboxylate | 426.5 | *** | *** |
| (R)-1-methoxypropan-2-yl 4-(3-(2-methoxypyridin-3-yl)pyrazolo[1,5-a]pyrimidin-5-yl)piperazine-1-carboxylate | 426.5 | * | *** |

TABLE 1-continued

| Compound | MW | CBA IC$_{50}$ μM | P81 IC$_{50}$ μM |
|---|---|---|---|
| 2-methoxy-2-oxoethyl 4-(3-(2-methoxypyridin-3-yl)pyrazolo[1,5-a]pyrimidin-5-yl)piperazine-1-carboxylate | 426.4 | — | ** |
| isopropyl 4-(3-bromopyrazolo[1,5-a]pyrimidin-5-yl)-d$_8$-piperazine-1-carboxylate | 376.2 | — | ** |
| 2-methoxyethyl 4-(3-(2-methoxypyridin-3-yl)pyrazolo[1,5-a]pyrimidin-5-yl)-d$_8$-piperazine-1-carboxylate | 420.4 | ** | *** |
| isopropyl 4-(3-(2-methoxy-6-methylpyridin-3-yl)pyrazolo[1,5-a]pyrimidin-5-yl)-d$_8$-piperazine-1-carboxylate | 418.4 | *** | *** |
| N-(3-(2-methoxypyridin-3-yl)pyrazolo[1,5-a]pyrimidin-5-yl)butyramide | 311.3 | — | ** |

5.6.41. Pharmacological Effects

Studies of AAK1 knockout mice showed that disruption of the AAK1 gene affects pain response as measured using the formalin paw test. See Example 5.6.1, above. The same test was used to confirm that the administration of an AAK1 inhibitor can also affect pain response.

Mice were tested for nociception with Automatic Nociception Analyzers (purchased from the Ozaki lab at University of California, San Diego). A metal band was placed around the left hind paw of each mouse with superglue 30 minutes prior to testing. After the 30-minute acclimation period, 20 μl of 5% formalin was subcutaneously injected in the dorsal surface of the left hind paw. Mice were individually housed in cylindrical chambers for 45 minutes. Fresh 5% formalin solution was prepared by diluting formaldehyde (Formalde-fresh 20%, Fisher Scientific, Fair Lawn, N.J.) with distilled water. Investigatory compounds were administered 30 minutes prior to formalin injection.

A computer software recorded flinches per minute, total flinches for Phase I (acute phase=first 8 minutes), and total flinches for Phase II (tonic phase between 20-40 minutes) through an electromagnetic field. See Yaksh T L, Ozaki G, McCumber D, Rathbun M, Svensson C, Malkmus S, Yaksh M C. An automated flinch detecting system for use in the formalin nociceptive bioassay. *J Appl Physiol.*, 2001; 90:2386-402.

Various compounds of the invention were tested at different doses. Gabapentin and pregabalin were used as positive controls. Results are shown below in Table 2, wherein "*" means an effect equal to or greater than 50 percent of that of gabapentin at 200 mpk, "**" means an effect equal to or greater than 100 percent of that of gabapentin at 200 mpk, "sc" means subcutaneous administration, and "po" means oral administration.

TABLE 2

| Compound | Dose (mpk) | Effect |
|---|---|---|
| Gabapentin | 50 sc | * |
| Gabapentin | 200 sc | ** |
| Pregabalin | 50 sc | * |
| (S)-tert-butyl 2-(((3-(2-methoxyphenyl)pyrazolo[1,5-a]pyrimidin-5-yl)amino)methyl)pyrrolidine-1-carboxylate | 10 sc | * |
| (S)-tert-butyl 2-(((3-(2-methoxyphenyl)pyrazolo[1,5-a]pyrimidin-5-yl)amino)methyl)pyrrolidine-1-carboxylate | 60 sc | * |
| (S)-tert-butyl 2-(((3-(pyridin-4-yl)pyrazolo[1,5-a]pyrimidin-5-yl)amino)methyl)pyrrolidine-1-carboxylate | 30 sc | ** |
| isopropyl 4-(3-(2-methoxyphenyl)pyrazolo[1,5-a]pyrimidin-5-yl)piperazine-1-carboxylate | 30 sc | ** |
| isopropyl 4-(3-(2-methoxypyridin-3-yl)pyrazolo[1,5-a]pyrimidin-5-yl)piperazine-1-carboxylate | 10 po | * |
| isopropyl 4-(3-(2-methoxypyridin-3-yl)pyrazolo[1,5-a]pyrimidin-5-yl)piperazine-1-carboxylate | 30 po | ** |

These results demonstrate that AAK1 inhibitors can be used to treat pain.

All publications (e.g., patents and patent applications) cited above are incorporated herein by reference in their entireties.

What is claimed is:

1. A compound of the formula:

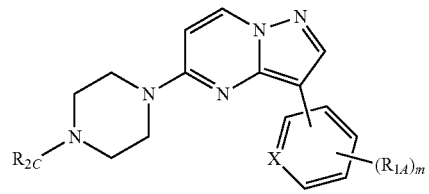

or a pharmaceutically acceptable salt thereof, wherein:
X is CH or N;
each $R_{1A}$ is independently —$OR_{1C}$, —$N(R_{1C})_2$, —C(O)$R_{1C}$, —C(O)O$R_{1C}$, —C(O)N($R_{1C}$)$_2$, —N($R_{1C}$)C(O) O$R_{1C}$, cyano, halo, or optionally substituted $C_{1-12}$ hydrocarbyl or 2-12-membered heterocarbyl, which optional substitution is with one or more $R_{1B}$;
each $R_{1B}$ is independently —$OR_{1C}$, —$N(R_{1C})_2$, —C(O)$R_{1C}$, —C(O)O$R_{1C}$, —C(O)N($R_{1C}$)$_2$, —N($R_{1C}$)C(O) O$R_{1C}$, cyano or halo;
each $R_{1C}$ is independently hydrogen or optionally substituted $C_{1-12}$ hydrocarbyl or 2-12-membered heterocarbyl, which optional substitution is with one or more of cyano, halo or hydroxyl;
each $R_{2C}$ is independently —$OR_{2D}$, —$N(R_{2D})_2$, —C(O)$R_{2D}$, —C(O)O$R_{2D}$, —C(O)N($R_{2D}$)$_2$, —N($R_{2D}$)C(O) O$R_{2D}$, cyano, halo, or optionally substituted $C_{1-12}$ hydrocarbyl or 2-12-membered heterocarbyl, which optional substitution is with one or more amino, cyano, halo, hydroxyl, or $R_{2D}$;

each $R_{2D}$ is independently hydrogen or optionally substituted $C_{1-12}$ hydrocarbyl or 2-12-membered heterocarbyl, which optional substitution is with one or more of amino, cyano, halo, hydroxyl; and m is 0-3.

2. The compound of claim 1, which is of the formula:

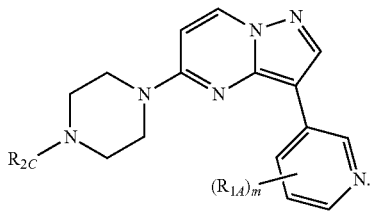

3. The compound of claim 2, which is of the formula:

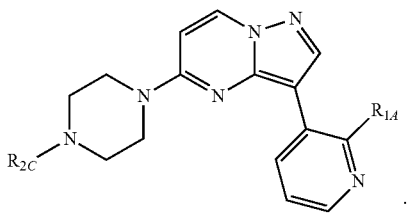

4. The compound of claim 2, which is of the formula:

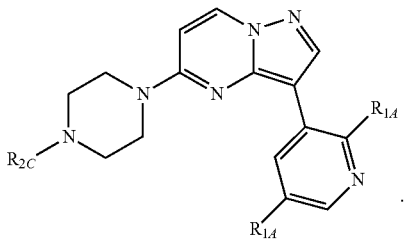

5. The compound of claim 1, wherein at least one $R_{1A}$, is halo.

6. The compound of claim 1, wherein at least one $R_{1A}$ is $-OR_{1C}$.

7. The compound of claim 6, wherein $R_{1C}$ is optionally substituted $C_{1-12}$ hydrocarbyl.

8. The compound of any of claim 1, wherein $R_{2C}$ is $-C(O)OR_{2D}$, $-C(O)N(R_{2D})_2$, or $-N(R_{2D})C(O)OR_{2D}$.

9. The compound of claim 1, wherein $R_{2C}$ is $-C(O)R_{2D}$.

10. The compound of claim 8, wherein each $R_{2D}$ is independently hydrogen or $C_{1-12}$ hydrocarbyl.

11. The compound of claim 8, wherein at least one $R_{2D}$ is optionally substituted $C_{1-12}$ hydrocarbyl, which optional substitution is with one or more of amino, cyano, halo, hydroxyl.

12. The compound of claim 8, wherein $R_{2D}$ is 2-12-membered heterocarbyl comprising at least one nitrogen atom.

13. The compound of claim 9, wherein $R_{2D}$ is independently hydrogen or $_{1-12}$ hydrocarbyl.

14. The compound of claim 9, wherein $R_{2D}$ is optionally substituted $C_{1-12}$ hydrocarbyl, which optional substitution is with one or more of amino, cyano, halo, hydroxyl.

15. The compound of claim 9, wherein $R_{2D}$ is 2-12-membered heterocarbyl comprising at least one nitrogen atom.

* * * * *